United States Patent [19]

Hogan et al.

[11] Patent Number: 6,074,826
[45] Date of Patent: Jun. 13, 2000

[54] NUCLEIC ACID AMPLIFICATION OLIGONUCLEOTIDES AND PROBES TO LYME DISEASE ASSOCIATED *BORRELIA*

[75] Inventors: James J. Hogan, Coronado; Yeasing Yang; Nick Carter, both of San Diego, all of Calif.

[73] Assignee: Gen-Probe Incorporated, San Diego, Calif.

[21] Appl. No.: 08/953,094

[22] Filed: Oct. 17, 1997

Related U.S. Application Data

[63] Continuation of application No. 08/374,863, Jan. 19, 1995, abandoned.
[51] Int. Cl.[7] .............................. C12Q 1/68; C12P 19/34; C07H 21/04
[52] U.S. Cl. .......................... 435/6; 435/91.2; 435/91.5; 536/24.32; 536/24.33
[58] Field of Search ........................... 435/6, 91.2, 91.5; 536/24.32, 24.33; 935/8, 17, 78

[56] References Cited

U.S. PATENT DOCUMENTS

| 4,851,330 | 7/1989 | Kohne et al. | 435/6 |
|---|---|---|---|
| 5,030,557 | 7/1991 | Hogan et al. | 435/6 |
| 5,185,439 | 2/1993 | Arnold, Jr. et al. | 435/6 |
| 5,283,174 | 2/1994 | Arnold, Jr. et al. | 435/6 |
| 5,466,577 | 11/1995 | Weisburg | 435/6 |

FOREIGN PATENT DOCUMENTS

| 0421725A | 2/1989 | European Pat. Off. . |
|---|---|---|
| 0 318 245 B1 | 5/1989 | European Pat. Off. . |
| 0386987A | 6/1989 | European Pat. Off. . |
| 0 421 725 B1 | 4/1991 | European Pat. Off. . |
| 8803957 | 6/1988 | WIPO . |
| 8902476 | 9/1988 | WIPO . |
| 9114002 | 3/1991 | WIPO . |
| WO 91/14002 | 9/1991 | WIPO . |
| 9207864 | 5/1992 | WIPO . |
| 9403472 | 7/1993 | WIPO . |

OTHER PUBLICATIONS

GenBank Accession No. M60968, M60969 and M88330, 1992.
Zhang, et al., "Organization of Ribosomal RNA Genes in *Borelia burgdorferi* sensu lato Isolated from *Ixodes ovatus* in Japan" *Microbiol. Immunol.* 37(11):909–913 (1993).
Rijpkema, et al., "Simultaneous Detection and Genotyping of Three Genomic Groups of *Borrelia burgdorferi* Sensu Lato in Dutch *Ixodes ricinus* Ticks by Characterization of the Amplified Intergenic Spacer Region between 5S and 23S rRNA Genes" *J. Clin. Microbiol.* 33(12):3091–3095 (1995).
Schwartz, et al., "rRNA Gene Organization in the Lyme Disease Spirochete, *Borrelia burgdorferi*" *J. Bacteriol.* 174(11):3757–3765 (1992).
Davidson, Barrie E. et al., Physical Map of the Linear Chromosome of the Bacterium *Borrelia burgdorfer* 212, a Causative Agent of Lyme Disease, and Localizatiion of rRNA Genes *Journal of Bateriology*, vol. 174, No. 11 pp. 3766–3774 (Jun. 1992).

Schwartz, Ira et al., "Diagnosis of Early Lyme Disease by Polymerase Chain Reaction Amplification and CUlture of Skin Biopsies from Erythema Migrans Lesions" *Journal of Clinical Microbiology*, vol. 30, No. 12, pp. 3082–3088 (Dec. 1992).
Marconi, Richard T. and Claude F. Guron, "Development of Polymerase Chain Reaction Primer Sets for Diagnosis of Lyme Disease and for Species–Specific Identification of Lyme Disease Isolates by 16S rRNA Signature Nucleotide Analysis" *Journal of Clinical Microbiology*, vol. 30, No. 11, pp. 2830–2834 (Nov. 1992).
Marconi, Richard T. et al., "Species–Specific Identification of and Distinction between *Borrelia burgdorferi* Genomic Groups by Using 16S rRNA–Directed Oligonucleotide Probes" *Journal of Clinical Microbiology*, vol. 30, No. 3, pp. 628–632 (Mar. 1992).
Adam, Thomas et al., "Phenotropic and Genotypic Analysis of *Borrelia burgdorferi* Isolates from Various Sources" *Infection and Immunity*, vol. 59, No. 8, pp. 2579–2585 (Aug. 1991).
Lebech, Anne–Mette et al., Comparison of In Vitro Culture and Polymerase Chain Reaction for Detection of *Borrelia burgdorferi* in Tissue from Experimentally Infected Animals *Journal of Clinical Microbiology*, vol. 29, No. 4, pp. 731–737 (Apr. 1991).
Goodman, Jesse L. et al., "Molecular Detection of Persistent *Borrelia burgdorferi* in the Urine of Patients with Active Lyme Disease" *Infectionand Immunity*, vol. 59, No. 1, pp. 269–278 (Jan. 1991).
Malloy, Diane C., et al. "Detection of *Borrelia burgdorferi* Using the Polymerase Chain Reaction" *Journal of Clinical Microbiology*, vol. 28, No. 6, pp. 1089–1093 (Jun. 1990).
Postic, D. et al., "Two Genomic Species in *Borrelia Burgdorferi*", Res. Microbial, 141, pp. 465–475 (1990).
Fukunaga, Masahito and Masako Sohnaka, "Tandem Repeat of the 23s and 5s Ribosomal RNA Genes in *Borrelia Burgdorferi*, the Etiological Agent of Lyme Disease", *Biochemical and Biophysical Research Communications*, vol. 183, No. 3, pp. 952–957 (Mar. 1992).
Rosa, et al., *J. Infect. Dis.*, 160:1018 (1989).
Barbour, Alan G. and Durland Fish, "The Biological and Social Phenomenon of Lyme Disease", *Science*, vol. 260, pp. 1610–1616 (Jun., 1993).
Golightly, Marc G., "Laboratory Considerations in the Diagnosis and Management of Lyme Borreliosis", *Clinical Pathology*, vol. 99, No. 2, pp. 168–174 (Feb. 1993).

(List continued on next page.)

*Primary Examiner*—Carla J. Myers
*Attorney, Agent, or Firm*—Charles B. Cappellari; Carols A. Fisher

[57] ABSTRACT

The present invention discloses hybridization assay probes, amplification primers, nucleic acid compositions and methods useful for detecting Borrelia nucleic acids. Hybridization assay probes and amplification primers that selectively detect Lyme disease-associated Borrelia and distinguish those Borrelia from *Borrelia hermsii* are disclosed. Other hybridization probes selectively detect *Borrelia hermsii* and not Lyme disease-associated Borrelia are also described.

111 Claims, No Drawings

OTHER PUBLICATIONS

Pfister, Hans–Walter, et al., "Lyme borreliosis: basic science and clinical aspects", *The Lancet*, vol. 343, pp. 1013–1016, (Apr. 1994).

Arnold et al. "Assay Format Involving Acridinium–Ester–Labeled DNA Probes", *Clin. Chem.* 35/8, 1588–1594 (1989).

Barone et al., "In Situ Acivation of bis–dialkylaminophosphines—a new method for synthesizing deoxyoligonucleotides on polymer supports", *Nucleic Acids Research*, vol. 12, No. 10, pp. 4051–4061 (1984).

Nelson et al., "Non–Isotopic DNA Probe Technologies", *Academic Press*, San Diego (Kricka, ed. 1992).

Barbour, Alan G. and Claude F. Garon, "Linear Plasmids of the Bacterium *Borrelia burgdorferi* Have Covalently Closed Ends" *Science*, vol. 237, No. 4813, pp. 409–411 (1987).

Steere, Alan C., "Medical Process—Lyme Disease", *The New England Journal of Medicine*, vol. 321, No. 9, pp. 586–596 (1989).

Barbour, Alan G. and Stanley F. Hayes, "Biology of Borrelia Species", *Microbiological Reviews*, vol. 50, No. 4, pp. 381–400 (1986).

Fukunaga et al., "The 23S/5S Ribosomal RNA Genes (rrl/rrf) are Separate from the 16S Ribosomal RNA Gene (rrs) in *Borrelia burgdorferi*, the Aetiological Agent of Lyme Disease", *Journal of General Microbiology*, 138:871–877 (1992).

Marconi, Richard T. and Claude F. Garon, "Identification of a Third Genomic Group of *Borrelia burgdorferi* Through Signature Nucleotide Analysis and 16S rRNA Sequence Determination", *Journal of General Microbiology*, 138:533–536 (1992).

Paster et al., "Phylogenetic Analysis of the Spirochetes", *Journal of Bacteriology* vol. 173, No. 19, pp. 6101–6109 (1991).

Marconi, Richard T. and Claude F. Garon, Phylogenetic Analysis of the Genus Borrelia: a Comparison of North American and European Isolates of *Borrelia burgdorferi Journal of Bacteriology*, vol. 174, No. 1, pp. 241–244 (1992).

Barbour, Alan G. "The Diagnosis of Lyme Disease: Rewards and Perils" *Annals od Internal Medicine*, vol. 110, No. 7, pp. 501–502 (1989).

Schwan et al., "Identification of *Borrelia burgdorferi* and *B. hermsii* Using DNA Hybridization Probes", *Journal of Clinical Microbiology*, vol. 27, No. 8, pp. 1734–1738 (1989).

*The Biochemistry of the Nucleic Acids*, (Adams et al., eds. 1992).

Schwan, Tom G. and Alan G. Barbour "Efficacy of Nucleic Acid Hybridization Probes for the Detection and Identification of *Borrelia burgdorferi*".

Anderson, John F., "Epizootiology of Borrelia in Ixodes Tick Vectors and Reservoir Hosts", *Reviews of Infectious Diseases*, vol. 11, Supplement 6, pp. S1451–S1459 (1989).

Adam et al, Medical Microbiology Letters, (1992) 1:120–126.

Compton, Nature (1991) 350:91–92.

The Stratagene Catalog (1988) p. 39.

SEQUENCE LISTING (1) GENERAL INFORMATION:

(iii) NUMBER OF SEQUENCES: 67

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 1:

GCATAGACTT ATATATCCGC C                                                  21

(2) INFORMATION FOR SEQ ID NO: 2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 2:

GGCGGATATA TAAGTCTATG C                                                  21

(2) INFORMATION FOR SEQ ID NO: 3:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (xi) SEQUENCE DESCRIPTION: SEQ ID NO: 3:

TACTCACCCT TTACGCCCAA TAATCCCG                                    28

(2) INFORMATION FOR SEQ ID NO: 4:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (xi) SEQUENCE DESCRIPTION: SEQ ID NO: 4:

CGGGATTATT GGGCGTAAAG GGTGAGTA                                    28

(2) INFORMATION FOR SEQ ID NO: 5:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 5:

CCAACATAGG TCCACAGTTG AGCTGTGGTA TTTTAT                         36

(2) INFORMATION FOR SEQ ID NO: 6:

(i) SEQUENCE CHARACTERISTICS:
       (A) LENGTH: 36 base pairs
       (B) TYPE: nucleic acid
       (C) STRANDEDNESS: single (D) TOPOLOGY:           linear (xi) SEQUENCE DESCRIPTION: SEQ ID NO: 6:

ATAAAATACC ACAGCTCAAC TGTGGACCTA TGTTGG                           36

(2) INFORMATION FOR SEQ ID NO:    7:

(i) SEQUENCE CHARACTERISTICS:
            (A) LENGTH:             29 base pairs
            (B) TYPE:               nucleic acid
            (C) STRANDEDNESS:       single
            (D) TOPOLOGY:           linear (xi) SEQUENCE DESCRIPTION: SEQ ID NO: 7:

AGCCGCGGTA ATACGTAAGG GTTTAGCGT                                   29

(2) INFORMATION FOR SEQ ID NO:    8:

(i) SEQUENCE CHARACTERISTICS:
            (A) LENGTH:             39 base pairs
            (B) TYPE:               nucleic acid
            (C) STRANDEDNESS:       single
            (D) TOPOLOGY:           linear (xi) SEQUENCE DESCRIPTION: SEQ ID NO: 8:

CTTCCTCTAT CAGACTCTAG ACATATAGTT TCCAACATA                        39

(2) INFORMATION FOR SEQ ID NO:    9:

(i) SEQUENCE CHARACTERISTICS:
            (A) LENGTH:             36 base pairs
            (B) TYPE:               nucleic acid
            (C) STRANDEDNESS:       single
            (D) TOPOLOGY:           linear (xi) SEQUENCE DESCRIPTION: SEQ ID NO: 9:

CCACCCTTAC ACCAGAAATT CTAACTTCCT CTATCA                           36

(2) INFORMATION FOR SEQ ID NO:    10:

(i) SEQUENCE CHARACTERISTICS:
            (A) LENGTH:             21 base pairs
            (B) TYPE:               nucleic acid
            (C) STRANDEDNESS:       single
            (D) TOPOLOGY:           linear (xi) SEQUENCE DESCRIPTION: SEQ ID NO: 10:

GGCGGATATG CAAGTCTATG C                                           21

(2) INFORMATION FOR SEQ ID NO:    11:

(i) SEQUENCE CHARACTERISTICS:
            (A) LENGTH:             29 base pairs
            (B) TYPE:               nucleic acid
            (C) STRANDEDNESS:       single
            (D) TOPOLOGY:           linear (xi) SEQUENCE DESCRIPTION: SEQ ID NO: 11:

AGCCGCGGTA ATACGTAAGG GGCGAGCGT                                   29

(2) INFORMATION FOR SEQ ID NO:    12:

(i) SEQUENCE CHARACTERISTICS:
            (A) LENGTH:             21 base pairs
            (B) TYPE:               nucleic acid
            (C) STRANDEDNESS:       single
            (D) TOPOLOGY:           linear (xi) SEQUENCE DESCRIPTION: SEQ ID NO: 12:

GCAUAGACUU AUAUAUCCGC C                                              21

(2) INFORMATION FOR SEQ ID NO:    13:

(i) SEQUENCE CHARACTERISTICS:
        (A) LENGTH:              21 base pairs
        (B) TYPE:                nucleic acid
        (C) STRANDEDNESS:        single
        (D) TOPOLOGY:            linear (xi) SEQUENCE DESCRIPTION: SEQ ID NO: 13:

GGCGGAUAUA UAAGUCUAUG C                                              21

(2) INFORMATION FOR SEQ ID NO:    14:

(i) SEQUENCE CHARACTERISTICS:
        (A) LENGTH:              28 base pairs
        (B) TYPE:                nucleic acid
        (C) STRANDEDNESS:        single
        (D) TOPOLOGY:            linear (xi) SEQUENCE DESCRIPTION: SEQ ID NO: 14:

UACUCACCCU UUACGCCCAA UAAUCCCG                                       28

(2) INFORMATION FOR SEQ ID NO:    15:

(i) SEQUENCE CHARACTERISTICS:
        (A) LENGTH:              28 base pairs
        (B) TYPE:                nucleic acid
        (C) STRANDEDNESS:        single
        (D) TOPOLOGY:            linear (xi) SEQUENCE DESCRIPTION: SEQ ID NO: 15:

CGGGAUUAUU GGGCGUAAAG GGUGAGUA                                       28

(2) INFORMATION FOR SEQ ID NO:    16:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 16:

CCAACAUAGG UCCACAGUUG AGCUGUGGUA UUUUAU                              36

(2) INFORMATION FOR SEQ ID NO:    17:

(i) SEQUENCE CHARACTERISTICS:
        (A) LENGTH:              36 base pairs
        (B) TYPE:                nucleic acid
        (C) STRANDEDNESS:        single
        (D) TOPOLOGY:            linear (xi) SEQUENCE DESCRIPTION: SEQ ID NO: 17:

AUAAAAUACC ACAGCUCAAC UGUGGACCUA UGUUGG                              36

(2) INFORMATION FOR SEQ ID NO:    18:

(i) SEQUENCE CHARACTERISTICS:
        (A) LENGTH:              28 base pairs
        (B) TYPE:                nucleic acid
        (C) STRANDEDNESS:        single
        (D) TOPOLOGY:            linear (xi) SEQUENCE DESCRIPTION: SEQ ID NO: 18:

CTGAAAAGTG TAGTCGATGG GAAACGGG                                28

(2) INFORMATION FOR SEQ ID NO: 19:

(i) SEQUENCE CHARACTERISTICS:
        (A) LENGTH:           24 base pairs
        (B) TYPE:             nucleic acid
        (C) STRANDEDNESS:     single
        (D) TOPOLOGY:         linear (xi) SEQUENCE DESCRIPTION: SEQ ID NO: 19:

GCACTCATCA TCACATCTTA GCTC                                    24

(2) INFORMATION FOR SEQ ID NO: 20:

(i) SEQUENCE CHARACTERISTICS:
        (A) LENGTH:           24 base pairs
        (B) TYPE:             nucleic acid
        (C) STRANDEDNESS:     single
        (D) TOPOLOGY:         linear (xi) SEQUENCE DESCRIPTION: SEQ ID NO: 20:

CGTATTTTGC AGAGTTCCTT AACG                                    24

(2) INFORMATION FOR SEQ ID NO: 21:

(i) SEQUENCE CHARACTERISTICS:
        (A) LENGTH:           26 base pairs
        (B) TYPE:             nucleic acid
        (C) STRANDEDNESS:     single
        (D) TOPOLOGY:         linear (xi) SEQUENCE DESCRIPTION: SEQ ID NO: 21:

GGTGATGATC TTGATAGGAA AATCCG                                  26

(2) INFORMATION FOR SEQ ID NO: 22:

(i) SEQUENCE CHARACTERISTICS:
        (A) LENGTH:           26 base pairs
        (B) TYPE:             nucleic acid
        (C) STRANDEDNESS:     single
        (D) TOPOLOGY:         linear (xi) SEQUENCE DESCRIPTION: SEQ ID NO: 22:

GGTGTTGATT TTAGTAGGAA AATCCG                                  26

(2) INFORMATION FOR SEQ ID NO: 23:

(i) SEQUENCE CHARACTERISTICS:
        (A) LENGTH:           27 base pairs
        (B) TYPE:             nucleic acid
        (C) STRANDEDNESS:     single
        (D) TOPOLOGY:         linear (xi) SEQUENCE DESCRIPTION: SEQ ID NO: 23:

CGATGGTTGT CCTAGTTTAA GCATTAA                                 27

(2) INFORMATION FOR SEQ ID NO: 24:

(i) SEQUENCE CHARACTERISTICS:
        (A) LENGTH:           26 base pairs
        (B) TYPE:             nucleic acid
        (C) STRANDEDNESS:     single
        (D) TOPOLOGY:         linear (xi) SEQUENCE DESCRIPTION: SEQ ID NO: 24:

```
CGGATTTTCC TATCAAGATC ATCACC                                              26

(2) INFORMATION FOR SEQ ID NO:   25:

(i) SEQUENCE CHARACTERISTICS:
        (A) LENGTH:              26 base pairs
        (B) TYPE:                nucleic acid
        (C) STRANDEDNESS:        single
        (D) TOPOLOGY:            linear (xi) SEQUENCE DESCRIPTION: SEQ ID NO: 25:

GGUGAUGAUC UUGAUAGGAA AAUCCG                                              26

(2) INFORMATION FOR SEQ ID NO:   26:

(i) SEQUENCE CHARACTERISTICS:
        (A) LENGTH:              26 base pairs
        (B) TYPE:                nucleic acid
        (C) STRANDEDNESS:        single
        (D) TOPOLOGY:            linear (xi) SEQUENCE DESCRIPTION: SEQ ID NO: 26:

CGGAUUUUCC UAUCAAGAUC AUCACC                                              26

(2) INFORMATION FOR SEQ ID NO:   27:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (xi) SEQUENCE DESCRIPTION: SEQ ID NO: 27:

TTAATGCTTA AACTAGGACA ACCATCG                                             27

(2) INFORMATION FOR SEQ ID NO:   28:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (xi) SEQUENCE DESCRIPTION: SEQ ID NO: 28:

CGAUGGUUGU CCUAGUUUAA GCAUUAA                                             27

(2) INFORMATION FOR SEQ ID NO:   29:

(i) SEQUENCE CHARACTERISTICS:
        (A) LENGTH:              27 base pairs
        (B) TYPE:                nucleic acid
        (C) STRANDEDNESS:        single
        (D) TOPOLOGY:            linear (xi) SEQUENCE DESCRIPTION: SEQ ID NO: 29:

UUAAUGCUUA AACUAGGACA ACCAUCG                                             27

(2) INFORMATION FOR SEQ ID NO:   30:

(i) SEQUENCE CHARACTERISTICS:
        (A) LENGTH:              26 base pairs
        (B) TYPE:                nucleic acid
        (C) STRANDEDNESS:        single
        (D) TOPOLOGY:            linear (xi) SEQUENCE DESCRIPTION: SEQ ID NO: 30:
```

```
CGGATTTTCC TACTAAAATC AACACC                                       26

(2) INFORMATION FOR SEQ ID NO:   31:

(i) SEQUENCE CHARACTERISTICS:
          (A) LENGTH:           26 base pairs
          (B) TYPE:             nucleic acid
          (C) STRANDEDNESS:     single
          (D) TOPOLOGY:         linear (xi) SEQUENCE DESCRIPTION: SEQ ID NO: 31:

GGUGUUGAUU UUAGUAGGAA AAUCCG                                       26

(2) INFORMATION FOR SEQ ID NO:   32:

(i) SEQUENCE CHARACTERISTICS:
          (A) LENGTH:           26 base pairs
          (B) TYPE:             nucleic acid
          (C) STRANDEDNESS:     single
          (D) TOPOLOGY:         linear (xi) SEQUENCE DESCRIPTION: SEQ ID NO: 32:

CGGAUUUUCC UACUAAAAUC AACACC                                       26

(2) INFORMATION FOR SEQ ID NO:   33:

(i) SEQUENCE CHARACTERISTICS:
          (A) LENGTH:           21 base pairs
          (B) TYPE:             nucleic acid
          (C) STRANDEDNESS:     single
          (D) TOPOLOGY:         linear (xi) SEQUENCE DESCRIPTION: SEQ ID NO: 33:

GCATAGACTT GCATATCCGC C                                            21

(2) INFORMATION FOR SEQ ID NO:   34:

(i) SEQUENCE CHARACTERISTICS:
          (A) LENGTH:           21 base pairs
          (B) TYPE:             nucleic acid
          (C) STRANDEDNESS:     single
          (D) TOPOLOGY:         linear (xi) SEQUENCE DESCRIPTION: SEQ ID NO: 34:

GGCGGAUAUG CAAGUCUAUG C                                            21

(2) INFORMATION FOR SEQ ID NO:   35:

(i) SEQUENCE CHARACTERISTICS:
          (A) LENGTH:           21 base pairs
          (B) TYPE:             nucleic acid
          (C) STRANDEDNESS:     single
          (D) TOPOLOGY:         linear (xi) SEQUENCE DESCRIPTION: SEQ ID NO: 35:

GCAUAGACUU GCAUAUCCGC C                                            21

(2) INFORMATION FOR SEQ ID NO:   36:

(i) SEQUENCE CHARACTERISTICS:
          (A) LENGTH:           29 base pairs
          (B) TYPE:             nucleic acid
          (C) STRANDEDNESS:     single
          (D) TOPOLOGY:         linear (xi) SEQUENCE DESCRIPTION: SEQ ID NO: 36:

ACGCTAAACC CTTACGTATT ACCGCGGCT                                    29
```

(2) INFORMATION FOR SEQ ID NO: 37:

(i) SEQUENCE CHARACTERISTICS:
        (A) LENGTH:         39 base pairs
        (B) TYPE:           nucleic acid
        (C) STRANDEDNESS:   single
        (D) TOPOLOGY:      linear (xi) SEQUENCE DESCRIPTION: SEQ ID NO: 37:

TATGTTGGAA ACTATATGTC TAGAGTCTGA TAGAGGAAG                     39

(2) INFORMATION FOR SEQ ID NO: 38:

(i) SEQUENCE CHARACTERISTICS:
        (A) LENGTH:         36 base pairs
        (B) TYPE:           nucleic acid
        (C) STRANDEDNESS:   single
        (D) TOPOLOGY:      linear (xi) SEQUENCE DESCRIPTION: SEQ ID NO: 38:

TGATAGAGGA AGTTAGAATT TCTGGTGTAA GGGTGG                        36

(2) INFORMATION FOR SEQ ID NO: 39:

(i) SEQUENCE CHARACTERISTICS:
        (A) LENGTH:         29 base pairs
        (B) TYPE:           nucleic acid
        (C) STRANDEDNESS:   single
        (D) TOPOLOGY:      linear (xi) SEQUENCE DESCRIPTION: SEQ ID NO: 39:

ACGCTCGCCC CTTACGTATT ACCGCGGCT                               29

(2) INFORMATION FOR SEQ ID NO: 40:

(i) SEQUENCE CHARACTERISTICS:
        (A) LENGTH:         28 base pairs
        (B) TYPE:           nucleic acid
        (C) STRANDEDNESS:   single
        (D) TOPOLOGY:      linear (xi) SEQUENCE DESCRIPTION: SEQ ID NO: 40:

CCCGTTTCCC ATCGACTACA CTTTTCAG                                28

(2) INFORMATION FOR SEQ ID NO: 41:

(i) SEQUENCE CHARACTERISTICS:
        (A) LENGTH:         24 base pairs
        (B) TYPE:           nucleic acid
        (C) STRANDEDNESS:   single
        (D) TOPOLOGY:      linear (xi) SEQUENCE DESCRIPTION: SEQ ID NO: 41:

GAGCTAAGAT GTGATGATGA GTGC                                    24

(2) INFORMATION FOR SEQ ID NO: 42:

(i) SEQUENCE CHARACTERISTICS:
        (A) LENGTH:         24 base pairs
        (B) TYPE:           nucleic acid
        (C) STRANDEDNESS:   single
        (D) TOPOLOGY:      linear (xi) SEQUENCE DESCRIPTION: SEQ ID NO: 42:

CGTTAAGGAA CTCTGCAAAA TACG                                    24

(2) INFORMATION FOR SEQ ID NO: 43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 43:

AATTTAATAC GACTCACTAT AGGGAGA                                            27

(2) INFORMATION FOR SEQ ID NO: 44:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 44:

AGCCGCGGUA AUACGUAAGG GUUUAGCGU                                        29

(2) INFORMATION FOR SEQ ID NO: 45:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 45:

CUUCCUCUAU CAGACUCUAG ACAUAUAGUU UCCAACAUA                        39

(2) INFORMATION FOR SEQ ID NO: 46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 46:

CCACCCUUAC ACCAGAAAUU CUAACUUCCU CUAUCA                              36

(2) INFORMATION FOR SEQ ID NO: 47:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 47:

AGCCGCGGUA AUACGUAAGG GGCGAGCGU                                        29

(2) INFORMATION FOR SEQ ID NO: 48:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 48:

CUGAAAAGUG UAGUCGAUGG GAAACGGG                                          28

(2) INFORMATION FOR SEQ ID NO: 49:

(i) SEQUENCE CHARACTERISTICS:
        (A) LENGTH:         24 base pairs
        (B) TYPE:           nucleic acid
        (C) STRANDEDNESS:  single
        (D) TOPOLOGY:      linear (xi) SEQUENCE DESCRIPTION: SEQ ID NO: 49:

GCACUCAUCA UCACAUCUUA GCUC                                                24

(2) INFORMATION FOR SEQ ID NO: 50:

(i) SEQUENCE CHARACTERISTICS:
        (A) LENGTH:         24 base pairs
        (B) TYPE:           nucleic acid
        (C) STRANDEDNESS:  single
        (D) TOPOLOGY:      linear (xi) SEQUENCE DESCRIPTION: SEQ ID NO: 50:

CGUAUUUUGC AGAGUUCCUU AACG                                                24

(2) INFORMATION FOR SEQ ID NO: 51:

(i) SEQUENCE CHARACTERISTICS:
        (A) LENGTH:         29 base pairs
        (B) TYPE:           nucleic acid
        (C) STRANDEDNESS:  single
        (D) TOPOLOGY:      linear (xi) SEQUENCE DESCRIPTION: SEQ ID NO: 51:

ACGCUAAACC CUUACGUAUU ACCGCGGCU                                       29

(2) INFORMATION FOR SEQ ID NO: 52:

(i) SEQUENCE CHARACTERISTICS:
        (A) LENGTH:         39 base pairs
        (B) TYPE:           nucleic acid
        (C) STRANDEDNESS:  single
        (D) TOPOLOGY:      linear (xi) SEQUENCE DESCRIPTION: SEQ ID NO: 52:

UAUGUUGGAA ACUAUAUGUC UAGAGUCUGA UAGAGGAAG                   39

(2) INFORMATION FOR SEQ ID NO: 53:

(i) SEQUENCE CHARACTERISTICS:
        (A) LENGTH:         36 base pairs
        (B) TYPE:           nucleic acid
        (C) STRANDEDNESS:  single
        (D) TOPOLOGY:      linear (xi) SEQUENCE DESCRIPTION: SEQ ID NO: 53:

UGAUAGAGGA AGUUAGAAUU UCUGGUGUAA GGGUGG                      36

(2) INFORMATION FOR SEQ ID NO: 54:

(i) SEQUENCE CHARACTERISTICS:
        (A) LENGTH:         29 base pairs
        (B) TYPE:           nucleic acid
        (C) STRANDEDNESS:  single
        (D) TOPOLOGY:      linear (xi) SEQUENCE DESCRIPTION: SEQ ID NO: 54:

ACGCUCGCCC CUUACGUAUU ACCGCGGCU                                       29

(2) INFORMATION FOR SEQ ID NO: 55:

```
        (i) SEQUENCE CHARACTERISTICS:
             (A) LENGTH:            28 base pairs
             (B) TYPE:              nucleic acid
             (C) STRANDEDNESS:      single
             (D) TOPOLOGY:          linear (xi) SEQUENCE DESCRIPTION: SEQ ID NO: 55:

CCCGUUUCCC AUCGACUACA CUUUUCAG                                              28

(2) INFORMATION FOR SEQ ID NO:  56:

(i) SEQUENCE CHARACTERISTICS:
             (A) LENGTH:            24 base pairs
             (B) TYPE:              nucleic acid
             (C) STRANDEDNESS:      single
             (D) TOPOLOGY:          linear (xi) SEQUENCE DESCRIPTION: SEQ ID NO: 56:

GAGCUAAGAU GUGAUGAUGA GUGC                                                  24

(2) INFORMATION FOR SEQ ID NO:  57:

(i) SEQUENCE CHARACTERISTICS:
             (A) LENGTH:            24 base pairs
             (B) TYPE:              nucleic acid
             (C) STRANDEDNESS:      single
             (D) TOPOLOGY:          linear (xi) SEQUENCE DESCRIPTION: SEQ ID NO: 57:

CGUUAAGGAA CUCUGCAAAA UACG                                                  24

(2) INFORMATION FOR SEQ ID NO: 58:

(i) SEQUENCE CHARACTERISTICS:
             (A) LENGTH:            35 base pairs
             (B) TYPE:              nucleic acid
             (C) STRANDEDNESS:      single
             (D) TOPOLOGY:          linear (xi) SEQUENCE DESCRIPTION: SEQ ID NO: 58:

GGAACTTACC CGACAAGGAA TTTCGCTACC TTAGG                                      35

(2) INFORMATION FOR SEQ ID NO: 59:

(i) SEQUENCE CHARACTERISTICS:
             (A) LENGTH:            36 base pairs
             (B) TYPE:              nucleic acid
             (C) STRANDEDNESS:      single
             (D) TOPOLOGY:          linear (xi) SEQUENCE DESCRIPTION: SEQ ID NO: 59:

ACCGTTATAG TTACGGCCGC CGTTTACTGG GGCTTC                                     36

(2) INFORMATION FOR SEQ ID NO: 60:

(i) SEQUENCE CHARACTERISTICS:
             (A) LENGTH:            32 base pairs
             (B) TYPE:              nucleic acid
             (C) STRANDEDNESS:      single
             (D) TOPOLOGY:          linear (xi) SEQUENCE DESCRIPTION: SEQ ID NO: 60:

GCCTGGCCAT CGTTACGCCA TTCGTGCAGG TC                                         32

(2) INFORMATION FOR SEQ ID NO: 61:
```

```
      (i) SEQUENCE CHARACTERISTICS:
          (A) LENGTH:         30 base pairs
          (B) TYPE:           nucleic acid
          (C) STRANDEDNESS:   single
          (D) TOPOLOGY:       linear (xi) SEQUENCE DESCRIPTION: SEQ ID NO: 61:

GCCCAAATCG TTACGCCTTT CGTGCGGGTC                                     30

(2) INFORMATION FOR SEQ ID NO: 62:

(i) SEQUENCE CHARACTERISTICS:
          (A) LENGTH:         30 base pairs
          (B) TYPE:           nucleic acid
          (C) STRANDEDNESS:   single
          (D) TOPOLOGY:       linear (xi) SEQUENCE DESCRIPTION: SEQ ID NO: 62:

CCCGACCGTC CCTATTAATC ATTACGATGG                                     30

(2) INFORMATION FOR SEQ ID NO: 63:

(i) SEQUENCE CHARACTERISTICS:
          (A) LENGTH:         46 base pairs
          (B) TYPE:           nucleic acid
          (C) STRANDEDNESS:   single
          (D) TOPOLOGY:       linear (xi) SEQUENCE DESCRIPTION: SEQ ID NO: 63:

CTACGACGGT ATCTGATCAT CTTCGATCCC CTAACTTTCG TTCTTG                   46

(2) INFORMATION FOR SEQ ID NO: 64:

(i) SEQUENCE CHARACTERISTICS:
          (A) LENGTH:         20 base pairs
          (B) TYPE:           nucleic acid
          (C) STRANDEDNESS:   single
          (D) TOPOLOGY:       linear (xi) SEQUENCE DESCRIPTION: SEQ ID NO: 64:

GGCGGUUUGU UAAGUCUGAU                                                20

(2) INFORMATION FOR SEQ ID NO: 65:

(i) SEQUENCE CHARACTERISTICS:
          (A) LENGTH:         21 base pairs
          (B) TYPE:           nucleic acid
          (C) STRANDEDNESS:   single
          (D) TOPOLOGY:       linear (xi) SEQUENCE DESCRIPTION: SEQ ID NO: 65:

GGCGGAUAUA UAAGUCUUAC G                                              21

(2) INFORMATION FOR SEQ ID NO: 66:

(i) SEQUENCE CHARACTERISTICS:
          (A) LENGTH:         21 base pairs
          (B) TYPE:           nucleic acid
          (C) STRANDEDNESS:   single
          (D) TOPOLOGY:       linear (xi) SEQUENCE DESCRIPTION: SEQ ID NO: 66:

GGCGGAUAUG CAAGUCUUAC G                                              21

(2) INFORMATION FOR SEQ ID NO: 67:

(i) SEQUENCE CHARACTERISTICS:
```

```
           (A) LENGTH:            23 base pairs
           (B) TYPE:              nucleic acid
           (C) STRANDEDNESS:      single
           (D) TOPOLOGY:          linear (xi) SEQUENCE DESCRIPTION: SEQ ID NO: 67:

GGCUGGUUUU CCAGGCAAAU CCG                                                      23
```

NUCLEIC ACID AMPLIFICATION OLIGONUCLEOTIDES AND PROBES TO LYME DISEASE ASSOCIATED *BORRELIA*

This application is a continuation of application Ser. No. 08/374,863, filed Jan. 19, 1995 now abandoned.

FIELD OF THE INVENTION

The inventions described and claimed herein relate to the design and use of amplification oligonucleotides and nucleic acid probes to Borrelia organisms associated with Lyme disease, which allow detection of the organism in test samples, e.g., from tissue samples and body fluids, and from cultures.

BACKGROUND OF THE INVENTION

Lyme disease is a frequently diagnosed human disease and is the most prevalent tick-borne disease in North America, Europe and other parts of the world with a moderate climate. See, A. G. Barbour & D. Fish, *Science* 260:1610–16 (1993); J. F. Anderson, *Rev. Insect Dis.* 11:51451–59 (1989); A. C. Steere, *N. Engl. J. Med.*, 331:586–96 (1989). Lyme disease or Lyme borreliosis is a multistage infection caused by Borrelia spirochetes. The Borrelia organism is transmitted to humans and animals by infected Ixodes ticks. White-tailed deer and the white-footed mouse, *Peromyscus leucopus*, serve as primary reservoirs in nature for the adult tick and larval forms, respectively.

Lyme borreliosis infection in humans and animals causes a number of different clinical manifestations depending upon the stage of the infection. Early infection of humans is usually a flu-like illness with a characteristic skin rash called erythema migrans. The erythema migrans spreads centrifugally and is usually ring-shaped. The erythema migrans usually develops within 1–5 weeks after a tick bite and spontaneously resolves in several weeks or months. See, H. W. Pfister et al., *Lancet* 343:1013 (1994).

Within a few weeks to several months after infection with Borrelia, the infection may spread to various organs including the brain, nerves, eyes, joints and heart. This spread of infection indicates stage II of the disease is underway. Neurological features of Lyme borreliosis including meningoradiculoneuritis (Bannwarth's syndrome), meningitis, cranial neuritis of the facial nerve, plexus neuritis, mononeuritis multiplex, and, rarely, encephalitis, myelitis, cerebral vasculitis, CSF lymphocyte pleocytosis.

Lyme carditis is a serious condition and commonly features transient atrioventricular block of various degrees, rhythm disturbances, myo-pericarditis and heart failure. Common symptoms of Lyme carditis include palpitations, chest discomfort, shortness of breath, dizziness on exercise and Adams-Stokes attacks.

Lyme borreliosis infection of the musculoskeletal system causes symptoms such as myalgia, arthralgia, arthritis, myositis and lymphadenopathy. Borrelia infection of the eyes produces symptoms such as conjunctivitis, iridocyclitis, choroiditis, optic neuropathy with pupilloedma, panophthalmitis. Infection of other organs may produce hepatomegaly, hepatitis, coughing and testicular swelling.

After months to years of infection, chronic organ involvement may occur indicating the lyme borreliosis has entered Stage III. Symptoms of this stage include chronic arthritis, monarticular arthritis, oligoarticular arthritis, acrodermatitis chronica atrophicans, encephalitis, myositis, keratitis, chronic polyneuropathy and dilated cardiomyopathy.

The Borrelia spirochetes known to cause Lyme borreliosis were originally designated *Borrelia burgdorferi*, but are now classified into three major genomic species. See, R. T. Marconi & C. F. Guron, *J. Clin. Microbiol.*, 30:2830–34 (1992). One group retains the species designation *B. burgdorferi*, a second has been designated *Borrelia garinii* and the third group has not yet been assigned a species name and is referred to as the VS461 group.

Another Borrelia species, *B. hermsii*, is closely related to *B. burgdorferi*, but is responsible for a different human disease, relapsing fever. *B. hermsii* has been characterized as belonging to the same species as *B. parheri* and *B. turicatae* by DNA hybridization, although each is specific for a particular arthropod vector (Barberi & Hayes, Microbiol Reviews 50:381–400, 1986). Two other Borrelia species *B. anserina* and *B. coriaceae* are closely related to *B. burgdorferi*, but are not infectious for humans.

Borrelia organisms have a wavy shape and flagella like other spirochetes. A. G. Barbour & S. F. Hayes, *Microbiol. Rev.*, 50:381–400 (1986). These organisms also have a chromosome and several extrachromosomal elements that are linear rather than circular. A. G. Barbour & C. F. Garon, *Science*, 237:409 (1987). Several surface-exposed lipoproteins, OspA and OspB have been identified and used as antigenic markers in serologic laboratory testing.

Cultivation of Borrelia organisms from body fluids is difficult, making microbiological diagnosis of lyme borreliosis by culturing unsatisfactory. Serological tests to detect *B. burgdorferi* have been developed including enzyme-linked immunosorbent assay [ELISA], indirect immunofluorescence assay (IFA) and western blotting. See, M. G. Golightly, *Am. J. Clin. Pathol.*, 99:168–74 (1993). However, poor standardization, false-positive and false-negative results do occur with these serologic tests and limit their usefulness. See, Barbour, *Ann. Intern. Med.*, 110:504 (1989). Patients with early (Stage I) or Stage II infections may not yet have developed detectable levels of antibodies and cross reactions with Treponema or other Borrelia not associated with Lyme disease may occur. Treatment with antibiotics may also prevent or delay the development of detectable antibodies in patients with Lyme borreliosis. Together these deficiencies limit the usefulness and reliability of serologic tests in diagnosis and treatment of Lyme borreliosis.

The use of oligonucleotides having specific nucleotide sequences as probes for the recognition of infectious agents is becoming an alternative to the problematic immunological detection assays. At least a portion of both genomic and plasmid DNA sequences of Borrelia have been obtained. See, Schwan et al., *J. Clin. Microbiol.*, 27:1734 (1989); Schwan et al., *Ann. N.Y. Acad. Sci.*, 539:419 (1988). Nucleic acid hybridization probes derived from the linear plasmid of *B. burgdorferi* were produced and used to identify *B. burgdorferi* from a number of Borrelia species. However, these probes are inherently limited because their nucleotide sequences are derived from plasmids that may become unstable over time or can be absent from pathogenic Borrelia isolates. Other nucleic acid hybridization probes targeted to specific Borrelia genes are also inherently limited by the degree of evolutionary stability of the targeted gene. See, e.g., Malloy et al., *J. Clin. Microbiol.*, 28:1089 (1990), Lebach et al., *J. Clin. Microbiol.*, 29:731–737 (1991); and Goodman et al., *Infect. Immun.*, 59:269–278 (1991).

Randomly cloned *B. burgdorferi* DNA sequences were used to construct nucleic acid primers and these primers have been used to amplify target DNA sequences in *B. burgdorferi*. See, Rosa et al., *J. Infect. Dis.*, 160:1018

(1989). However, not all *B. burgdorferi* isolates were detected, making these nucleic acid primers unsatisfactory for detection of all *B. burgdorferi* causing Lyme disease.

The ribosomal RNA (rRNA) genes of *B. burgdorferi* have been mapped and cloned by Fukunaga and Sohnaka, *Biochem. Biophys. Res. Comm.*, 183:952–57 (1992); and Postic et al., *Res. Microbiol.*, 141:465–475 (1990). *B. burgdorferi* is unusual in that it appears to contain two copies of the 23S RNA gene and only one copy of the gene encoding 16S rRNA per chromosome. (Fukanaga et al., *J. Gen Micobiol.* 138:871–877, 1992). The sequence of Borrelia 16S RNA has been used to design hybridization probes that could detect cultured *B. burgdorferi* organisms. See, Marconi et al., *J. Clin. Microbiol.*, 30:628–32 (1992). The usefulness of the probes to detect *B. burdorferi* in clinical samples without culturing the organisms was not proven.

To overcome these limitations, nucleic acid amplification of ribosomal RNA sequences has also been described using a broad specificity primer pair to amplify Borrelia 16S rDNA. See, Malloy et al., *J. Clin. Microbiol.*, 28:1089–93 (1990). However, the nucleic acid primers used also amplified *S. aureus* and *P. aeruginosa* and thus were not specific for *Borrelia burgdorferi*.

Four sets of primers derived from 16S rRNA sequences have been used to amplify the DNA of three different Borrelia genomic classes. See, R. T. Marconi and C. F. Baron, *J. Clin. Microbiol.*, 30:2830–34 (1992). Only one primer set, derived from positions 819–842 and 1153–1173 of the Borrelia 16S rRNA, detected all Borrelia organisms present in the various cultured Lyme disease isolates tested. Other primer sets either failed to recognize all three groups of Lyme disease Borrelia or also recognized Borrelia not associated with Lyme disease. The other primer sets failed to amplify all the various Borrelia organisms cultured from the clinical isolates.

The amplification of a 16S rRNA subsequence and of subtypes of *Borrelia burgdorferi* which vary in the V4 region of the 16S rRNA gene has been described by Adam et al., *Infec. Immun.*, 59:2579–85 (1991). PCR primers have been used to amplify a specific region of 23S rRNA of *B. burgdorferi* and to distinguish it from other species of Borrelia. See Schwartz et al., *J. Clin. Micro.* 30:3082 (1992).

Other probes complementary to Borrelia 16S rRNA sequences have been described by Weisburg, EPO Publication No. EPO 0421 725A, Application No. 90310766.2. White and Dodge, PCT US91/01574, disclose primers and probes derived from the 16S rRNA gene of *B. burgdorferi* and *B. hermsii*.

Because of the current limitations in serologically detecting and identifying Lyme disease, a need exists for a sensitive procedure to detect all geographical isolates of Borrelia associated with Lyme disease.

SUMMARY OF INVENTION

The featured invention discloses and claims novel and useful amplification oligonucleotides, helper oligonucleotides, and oligonucleotide hybridization assay probes which are designed to be complementary to specific regions of the rRNA (ribosomal RNA) or rDNA (ribosomal DNA) nucleotide sequences of Borrelia, or oligonucleotides having a nucleic acid sequence substantially corresponding to a specific portion of Borrelia rRNA or rDNA nucleotide sequence or its complement. Because these amplification oligonucleotides, helper oligonucleotides and hybridization assay probes are derived from the 16S and 23S rRNA of pathogenic Borrelia, a superior detection assay is obtained due to the higher level of RNA expressed from these rRNA genes, the slow rate of nucleic acid sequence changes and the lack of lateral transfer of the rRNA sequences between organisms.

The amplification oligonucleotides and oligonucleotide hybridization assay probes function by hybridizing to target Borrelia 16S and 23S rRNA and/or rDNA gene sequences under stringent hybridization assay conditions. In preferred embodiments, the probes and amplification oligonucleotides described herein can distinguish Lyme disease-associated Borrelia including *Borrelia burgdorferi, Borrelia garinii* and Borrelia of group VS461 from other microorganisms found in clinical samples such as blood or tissues and from other Borrelia species. Accordingly, the amplification oligonucleotides and hybridization assay probes may be used in an assay to specifically detect and/or quantitate Lyme disease-associated Borrelia. In preferred embodiments, the hybridization assay probes described herein are able to selectively hybridize to nucleic acids from Lyme disease-associated Borrelia and not to those from *Borrelia hermsii* under stringent hybridization conditions. In some embodiments of the present invention, the hybridization assay probe comprises an oligonucleotide that contains a reporter group such as an acridinium ester or a radioisotope to help identify hybridization of the probe to its target sequence. In some embodiments of the present invention, the amplification oligonucleotide optionally has a nucleic acid sequence recognized by an RNA polymerase or which enhances initiation or elongation by an RNA polymerase.

The present invention features hybridization assay probes useful for detecting the presence of nucleic acids from Lyme disease-associated Borrelia and *Borrelia hermsii*. Preferably, the hybridization assay probes are selected from the following nucleotide sequences:

SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG,
SEQ ID NO 26: CGGAUUUUCCUAUCAAGAUCAUCACC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

The present invention features hybridization assay probes useful for detecting nucleic acids from Lyme disease-associated Borrelia. These hybridization assay probes are preferably selected from the following nucleotide sequences:

SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 21: GGTGATGATCTTGATAGGAAAATCCG,
SEQ ID NO 24: CGGATTTTCCTATCAAGATCATCACC,

SEQ ID NO 25: GGUGAUGAUCUUGAUAGGAAAAUCCG, and
SEQ ID NO 26: CGGAUUUUCCUAUCAAGAUCACACC.

The present invention also features hybridization assay probes useful for detecting *Borrelia hermsii* nucleic acids. Preferably, these hybridization assay probes have a nucleotide sequence selected from one of the following nucleotide sequences:
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

Another aspect of the present invention is a probe mix comprising a hybridization assay probe of the present invention together with a helper oligonucleotide (probe). Preferably, helper oligonucleotides are used to facilitate the specific hybridization of the assay probe to its target nucleic acid; helper oligonucleotides are described by Hogan and Milliman U.S. Pat. No. 5,030,557 which is hereby incorporated by reference and enjoys common ownership with the present invention. Oligonucleotides used as helper probes in this invention include the following sequences:

SEQ ID NO 3: TACTCACCCTTTACGCCCAATAATCCCG,
SEQ ID NO 4: CGGGATTATTGGGCGTAAAGGGTGAGTA,
SEQ ID NO 5: CCAACATAGGTCCACAGTTGAGCTGTGGTATTTTAT,
SEQ ID NO 6: ATAAAATACCACAGCTCAACTGTGGACCTATGTTGG,
SEQ ID NO 14: UACUCACCCUUUACGCCCAAUAAUCCCG,
SEQ ID NO 15: CGGGAUUAUUGGGCGUAAAGGGUGAGUA,
SEQ ID NO 16: CCAACAUAGGUCCACAGUUGAGCUGUGGUAUUUUAU,
SEQ ID NO 17: AUAAAAUACCACAGCUCAACUGUGGACCUAUGUUGG,
SEQ ID NO 23: CGATGGTTGTCCTAGTTTAAGCATTAA,
SEQ ID NO 27: TTAATGCTTAAACTAGGACAACCATCG,
SEQ ID NO 28: CGAUGGUUGUCCUAGUUUAAGCAUUAA, and
SEQ ID NO 29: UUAAUGCUUAAACUAGGACAACCAUCG.

Another aspect of the present invention is compositions for detecting Lyme disease associated Borrelia that are nucleic acid hybrids formed between an oligonucleotide of the present invention and a specific region of a nucleotide polymer from a Lyme disease-associated Borrelia. Generally, the nucleotide polymer contains a nucleic acid sequence that substantially corresponds to an oligonucleotide sequence of the present invention or its complement and is derived from the rRNA or the rDNA encoding the ribosomal RNA of the Borrelia. The oligonucleotide present in these compositions may be an amplification oligonucleotide, a helper oligonucleotide, a hybridization assay probe, or a combination thereof. Thus, compositions of the present invention may contain one or more amplification oligonucleotides, one or more helper oligonucleotides, and one or more hybridization assay probes.

The compositions of the present invention containing a probe hybridized to its target sequence are useful for detecting the presence of a nucleic acid sequence. Compositions of the present invention containing a helper oligonucleotide hybridized to its target nucleic acid sequence are useful for making a particular portion of the target nucleic acid available for hybridization. compositions of the present invention containing an oligonucleotide primer hybridized to its target sequence are useful for creating an initiation site for a polymerase at the 3' end of the primer.

The present invention also contemplates methods for detecting the presence of Lyme disease associated Borrelia in which a test sample is contacted with a nucleic acid hybridization assay probe under stringent hybridization assay conditions wherein the nucleic acid hybridization assay probe is capable of hybridizing to *Borrelia burgdorferi* target nucleic acid sequences and not to the nucleic acid sequences from *Borrelia hermsii*. The present invention also contemplates oligonucleotides and the equivalents thereof used in these methods that optionally contain a reporter molecule that aids in the identification of the hybridization of the probe to its target sequence. This invention is useful for detecting the presence of Borrelia nucleic acids in test samples from humans such as blood, blood derived samples, tissues, tissue derived samples, other body fluids and body samples.

The present invention also contemplates methods for detecting the presence of Lyme disease associated Borrelia in which the nucleic acid is amplified using at least one amplification oligonucleotide of the present invention. In preferred embodiments, that amplification is then followed by a detection step in which the amplified nucleic acid is detected using an oligonucleotide hybridization assay probe of the present invention. The methods of the present invention also contemplate the use of amplification oligonucleotides which include the nucleotide sequence for an RNA promoter.

In another aspect, the invention features amplification oligonucleotides useful for detection of Lyme disease-associated spirochetes including *Borrelia burgdorferi* in an amplification assay. Such oligomers preferably substantially correspond to one of the following nucleotide sequences:

SEQ ID NO 7: AGCCGCGGTAATACGTAAGGGTTTAGCGT,
SEQ ID NO 8: CTTCCTCTATCAGACTCTAGACATATAGTTTCCAACATA,
SEQ ID NO 9: CCACCCTTACACCAGAAATTCTAACTTCCTCTATCA,
SEQ ID NO 11: AGCCGCGGTAATACGTAAGGGGCGAGCGT,
SEQ ID NO 18: CTGAAAAGTGTAGTCGATGGGAAACGGG,
SEQ ID NO 19: GCACTCATCATCACATCTTAGCTC,
SEQ ID NO 20: CGTATTTTGCAGAGTTCCTTAACG,
SEQ ID NO 44: AGCCGCGGUAAUACGUAAGGGUUUAGCGU,
SEQ ID NO 45: CUUCCUCUAUCAGACUCUAGACAUAUAGUUUCCAACAUA,
SEQ ID NO 46: CCACCCUUACACCAGAAAUUCUAACUUCCUCUAUCA,
SEQ ID NO 47: AGCCGCGGUAAUACGUAAGGGGCGAGCGU,
SEQ ID NO 48: CUGAAAAGUGUAGUCGAUGGGAAACGGG,

SEQ ID NO 49: GCACUCAUCAUCACAUCUUAGCUC, and SEQ ID NO 50: CGUAUUUUGCAGAGUUCCUUAACG, where the oligomer may be unmodified or contain a modification such as addition of a specific nucleic acid sequence to 5' terminus that is recognized by an RNA polymerase, (including but not limited to the promoter sequence for T7, T3, or SP6 RNA polymerase), and/or sequences which enhance initiation or elongation of RNA transcription by an RNA polymerase. One example of a promoter sequence includes the sequence SEQ ID NO. 43 5'-AATTTAATACGACTCACTATAGGGAGA-3'. Other examples of useful promoter sequences are contained in various commercially available vectors including, for example, pBluescript® vectors from Stratagene Cloning Systems or the pGEM™ vectors from Promega Biotec.

In another aspect of the present invention the amplification oligonucleotides bind to or cause elongation through sequences substantially corresponding to the following sequences:

SEQ ID NO 36: ACGCTAAACCCTTACGTATTACCGCGGCT,
SEQ ID NO 37: TATGTTGGAAACTATATGTCTAGAGTCTGATAGAGGAAG,
SEQ ID NO 38: TGATAGAGGAAGTTAGAATTTCTGGTGTAAGGGTGG,
SEQ ID NO 39: ACGCTCGCCCCTTACGTATTACCGCGGCT,
SEQ ID NO 40: CCCGTTTCCCATCGACTACACTTTTCAG,
SEQ ID NO 41: GAGCTAAGATGTGATGATGAGTGC,
SEQ ID NO 42: CGTTAAGGAACTCTGCAAAATACG,
SEQ ID NO 27: TTAATGCTTAAACTAGGACAACCATCG,
SEQ ID NO 51: ACGCUAAACCCUUACGUAUUACCGCGGCU,
SEQ ID NO 52: UAUGUUGGAAACUAUAUGUCUAGAGUCUGAUAGAGGAAG,
SEQ ID NO 53: UGAUAGAGGAAGUUAGAAUUUCUGGUGUAAGGGUGG,
SEQ ID NO 54: ACGCUCGCCCCUUACGUAUUACCGCGGCU,
SEQ ID NO 55: CCCGUUUCCCAUCGACUACACUUUUCAG,
SEQ ID NO 56: GAGCUAAGAUGUGAUGAUGAGUGC,
SEQ ID NO 29: UUAAUGCUUAAACUAGGACAACCAUCG, and
SEQ ID NO 57: CGUUAAGGAACUCUGCAAAAUACG.

Another aspect of the present invention includes kits that contain one or more of the oligonucleotides of the present invention including amplification oligonucleotides, helper oligonucleotides and hybridization assay probes. In preferred embodiments, a kit of the present invention includes at least one amplification oligonucleotide and one hybridization assay probe capable of distinguishing Lyme disease associated Borrelia from other microorganisms and other Borrelia species.

Background descriptions of the use of nucleic acid hybridization to detect particular nucleic acid sequences are given in Kohne, U.S. Pat. No. 4,851,330 issued Jul. 25, 1989, and by Hogan et al., International Patent Application No. PCT/US87/03009, entitled "Nucleic Acid Probes for Detection and/or Quantitation of Non-Viral Organisms", both references hereby incorporated by reference herein. Hogan et al., supra, describe methods for determining the presence of a non-viral organism or a group of non-viral organisms in a sample (e.g., sputum, urine, blood and tissue sections, food, soil and water).

DETAILED DESCRIPTION OF THE INVENTION

A. Definitions

The following terms have the indicated meanings in the specification unless expressly indicated to have a different meaning.

By "target nucleic acid" is meant a nucleic acid having a target nucleotide sequence.

By "oligonucleotide" is meant a single-stranded nucleotide polymer made of more than 2 nucleotide subunits covalently joined together. Preferably between 10 and 100 nucleotide units are present, most preferably between 12 and 50 nucleotides units are joined together. The sugar groups of the nucleotide subunits may be ribose, deoxyribose or modified derivatives thereof such as o-methyl ribose. The nucleotide subunits of an oligonucleotide may be joined by phosphodiester linkages, phosphorothioate linkages, methyl phosphonate linkages or by other rare or non-naturally-occurring linkages that do not prevent hybridization of the oligonucleotide. Furthermore, an oligonucleotide may have uncommon nucleotides or non-nucleotide moieties. An oligonucleotide as defined herein is a nucleic acid, preferably DNA, but may be RNA or have a combination of ribo- and deoxyribonucleotides covalently linked. Oligonucleotide probes and amplification oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of a probe is as a hybridization assay probe; probes may also be used as in vivo or in vitro therapeutic amplification oligomers or antisense agents to block or inhibit gene transcription, or translation in diseased, infected, or pathogenic cells.

By "target nucleic acid sequence", "target nucleotide sequence" or "target sequence" is meant a specific deoxyribonucleotide or ribonucleotide sequence comprising all or a part of the nucleotide sequence of a single-stranded nucleic acid molecule, and the deoxyribonucleotide or ribonucleotide sequence complementary thereto.

Nucleic acid hybridization is the process by which two nucleic acid strands having completely or partially complementary nucleotide sequences come together under predetermined reaction conditions to form a stable, double-stranded hybrid with specific hydrogen bonds. Either nucleic acid strand may be a deoxyribonucleic acid (DNA) or a ribonucleic acid (RNA); thus hybridization can involve RNA:RNA hybrids, DNA:DNA hybrids, or RNA:DNA hybrids.

The term "hybridization" as used in this application, refers to the ability of two completely or partly complementary single nucleic acid strands to come together in an antiparallel orientation to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G) on single nucleic acid strands, base pairing can form between bases who are not members of these "canonical" pairs. Non-canonical base pairing is well-known in the art. See e.g., *The Biochemistry of the Nucleic Acids* (Adams et al., eds., 1992).

"Stringent" hybridization assay conditions refer to conditions wherein a specific hybridization assay probe is able to hybridize with target nucleic acids (preferably rRNA or rDNA of Lyme disease-associated Borrelia) over other nucleic acids present in the test sample derived either from other microorganisms (e.g., *Borrelia hermsii*) or from humans. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

By "probe" is meant a single-stranded oligonucleotide having a sequence partly or completely complementary to a nucleic acid sequence sought to be detected, so as to hybridize thereto under stringent hybridization conditions. The term "probe" is meant to exclude naturally occurring nucleic acids. Purified oligonucleotide probes may be produced by techniques known in the art such as chemical synthesis and by in vitro or in vivo expression from recombinant nucleic acid molecules, e.g., retroviral vectors. Preferably probes are 10 to 100 nucleotides in length. Probes may or may not have regions which are not complementary to a target sequence, so long as such sequences do not substantially affect hybridization under stringent hybridization conditions. If such regions exist they may contain a 5' promoter sequence and/or a binding site for RNA transcription, a restriction endonuclease recognition site, or may contain sequences which will confer a desired secondary or tertiary structure, such as a catalytic active site or a hairpin structure on the probe, on the target nucleic acid, or both. A probe may be labeled with a reporter group moiety such as a radioisotope, a fluorescent or chemiluminescent moiety, with an enzyme or other ligand, which can be used for detection or confirmation that the probe has hybridized to the target sequence.

As used in this disclosure, the phrase "a probe (or oligonucleotide) having a nucleic acid sequence consisting essentially of a sequence selected from" a group of specific sequences means that the probe, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "substantially corresponding to a nucleic acid sequence" means that the referred to nucleic acid is sufficiently similar to the nucleic acid sequence such that the referred to nucleic acid has similar hybridization properties to a nucleic acid sequence in that it would hybridize with the same target nucleic acid sequences under stringent hybridization conditions.

One skilled in the art will understand that substantially corresponding probes and primers of the invention can vary from the referred-to sequence and still hybridize to the same target nucleic acid sequence. This variation from the nucleic acid may be stated in terms of a percentage of identical bases within the sequence or the percentage of perfectly complementary bases between the probe or primer and its target sequence. One skilled in the art will also understand that this variation could be expressed as the number of non-identical bases in a probe or primer or the number of mismatched bases of a probe that do not hybridize to a corresponding base of a target nucleic acid sequence. Probes or primers of the present invention substantially correspond to a nucleic acid sequence if these percentages are from 100% to 80% or from 0 base mismatches in a 10 nucleotide target sequence to 2 bases mismatched in a 10 nucleotide target sequence.

In preferred embodiments, the percentage is from 100% to 85%. In more preferred embodiments, this percentage can be from 90 to 100%; in other preferred embodiments, this percentage is from 95 to 100%. One skilled in the art will understand the various modifications to the hybridization conditions that might be required at various percentages of complementarity to allow hybridization to a specific target sequence without causing an unacceptable level of non-specific hybridization.

By "nucleic acid hybrid" or "hybrid" is meant a nucleic acid structure containing a double-stranded, hydrogen-bonded region, preferably of between 10 and 100 nucleotides in length, most preferably of between about 12 and 50 nucleotides in length, wherein each strand is complementary to the other and wherein the region is sufficiently stable under stringent hybridization conditions to be detected by means including but not limited to chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allow the single strands to hybridize together in a stable double-stranded hydrogen-bonded region under stringent hybridization conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "conservatively modified variants" is meant nucleic acids or oligonucleotides having a nucleotide sequence that is complementary to a nucleic acid region of another nucleic acid, such region in turn being perfectly complementary to a reference nucleic acid. Such conservatively modified variants are able to stably hybridize to a target nucleic acid region having a Borrelia nucleotide sequence under stringent hybridization conditions.

By "amplification oligonucleotide" is meant an oligonucleotide capable of hybridizing at a target nucleic acid sequence and acting as a primer for nucleic acid synthesis or a promoter template (e.g., for synthesis of a complementary strand, thereby forming a functional promoter sequence), or both, for the initiation of nucleic acid synthesis. If the amplification oligonucleotide is designed to initiate RNA synthesis, the oligonucleotide may contain nucleotide sequences which are non-complementary to the target sequence, but are recognized by an RNA polymerase (such as T7, T3 and SP6 RNA polymerase). An amplification oligonucleotide may or may not have a 3' terminus which is modified to prevent or lessen the amount of primer extension. An amplification oligonucleotide as defined herein will preferably be between 10 and 100 nucleotides in length; most preferably between about 12 and 50 nucleotides in length. While the amplification oligonucleotides of the present invention may be chemically synthesized or derived from a vector, such oligonucleotides are not naturally-occurring nucleic acids.

By "nucleic acid amplification" or "target amplification" is meant increasing the number of nucleic acid molecules having at least one target nucleic acid sequence.

By "antisense" or "negative sense" is meant having a nucleic sequence complementary to that of a reference nucleic acid sequence.

By "sense", "same-sense" or "positive sense" is meant having a nucleic acid sequence analogous to that of a reference nucleic acid sequence.

By "helper oligonucleotide" is meant a nucleic acid probe designed to hybridize with the target nucleic acid at a different locus than that of a labeled probe, thereby either increasing the rate of hybridization of the labeled probe, increasing the melting temperature ($T_m$) of the target:labeled probe hybrid, or both.

"Lyme disease-associated Borrelia" are Borrelia species that cause Lyme disease and include the Borrelia species or sub-species *Borrelia burgdorferi, Borrelia garinii* and Borrelia VS461. Typically, Lyme disease-associated Borrelia can be isolated from a mammal with Lyme disease.

"Phylogenetically closely related" means that the organisms are closely related to each other in an evolutionary sense and therefore would have significant similarities in morphology and a higher total nucleic acid sequence homology than organisms that are more distantly related. Organisms occupying adjacent and next to adjacent to positions on the phylogenetic tree are closely related. Organisms occupying positions further away than adjacent or next to adjacent positions on the phylogenetic tree will still be closely related if they have significant total nucleic acid sequence homolog.

B. Hybridization Conditions and Probe/Primer Design

Hybridization reaction conditions, most importantly the temperature of hybridization and the concentration of salt in the hybridization solution, can be selected to allow the amplification oligonucleotides or hybridization probes of the present invention to preferentially hybridize to nucleic acids having a target Borrelia nucleotide sequence, and not to other unselected nucleic acids suspected of being present in the test sample. At decreased salt concentrations and/or increased temperatures (called increased stringency) the extent of nucleic acid hybridization decreases as hydrogen bonding between paired nucleotide bases in the double-stranded hybrid molecule is disrupted; this process is called "melting".

Generally speaking, the most stable hybrids are those having the largest number of contiguous perfectly matched (i.e., hydrogen-bonded) nucleotide base pairs. Thus, such hybrids would usually be expected to be the last to melt as the stringency of the hybridization conditions increases. However, a double-stranded nucleic acid region containing one or more mismatched, "non-canonical", or imperfect base pairs (resulting in weaker or non-existent base pairing at that position in the nucleotide sequence of a nucleic acid) may still be sufficiently stable under conditions of relatively high stringency to allow the nucleic acid hybrid to be detected in a hybridization assay without cross reacting with other, non-selected nucleic acids present in the test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular amplification oligonucleotide or hybridization probe and those of the target and non-target nucleic acids on the other, one or more mismatches will not necessarily defeat the ability of the oligonucleotide to hybridize to that nucleic acid and not to non-target nucleic acids.

The hybridization assay probes of the present invention were chosen, selected, and/or designed to maximize the difference between the melting temperatures of the probe-:target hybrid ($T_m$, defined as the temperature at which half of the potentially double-stranded molecules in a given reaction mixture are in a single-stranded, denatured state) and the $T_m$ of a mismatched hybrid formed between the probe and the rRNA or rDNA of the phylogenetically most closely-related organisms expected to be present in the test sample, but not sought to be detected. While the unlabeled amplification oligonucleotides and helper oligonucleotides need not have such an extremely high degree of specificity as the labeled hybridization assay probe to be useful in the present invention, they are designed in a similar manner to preferentially hybridize to one or more target nucleic acids over other nucleic acids.

Nucleotide sequences of prokaryotic organisms contain rRNA genes encoding 5S, 16S, and 23S rRNA. The Borrelia nucleic acid sequences of the ribosomal RNA genes (rDNA) of Leptospira, Leptonema, Serpula, Spirochaeta, and Treponema 16S nucleic acid sequences were also used for comparison. The Borrelia nucleic acid sequence information was obtained from laboratory research and published sources (Marconi and Garon, *J. Gen. Microbiol.* 138:533–536 (1992); Paster et al., *J. Bacteriol.* 173:6161–6109 (1991); Marconi and Garon, *J. Bacteriol.* 174:241–244 (1992); Marconi & Garow, *J. Clin. Microbiol.* 30:2830–34 (1992); Davidson et al., *J. Bacteriol.* 174:3766–74 (1992).

To facilitate the identification of nucleic acid sequences to be used as probes and amplification oligonucleotides, the nucleotide sequences from different species of organisms were first aligned to maximize homology. Within the rRNA molecule there is a close relationship between the overall structure and function. This imposes restrictions on evolutionary changes in the primary sequence so that the secondary structure is maintained. For example, if a base is changed on one side of a helix, a compensating change is made to the other side to preserve the complementarity (this is referred to as co-variance). This allows two very different sequences to be aligned based on the conserved primary sequence and also on the conserved secondary structure elements. Potential target sequences for the hybridization probes were identified by noting variations in the homology of the aligned sequences.

The sequence evolution at each of the variable regions is mostly divergent. Because of the divergence, more distant phylogenetic relatives of Lyme disease-associated Borrelia show greater variability in the variable region than phylogenetically closer relatives. We observed sufficient variation between Lyme disease-associated Borrelia and other Borrelia species which might be found in the same sample to identify preferred target sites and design useful probes.

We have identified sequences which vary between Borrelia species which are associated with Lyme disease and other Borrelia species by comparative analysis of rRNA sequences published in the literature or determined in the laboratory. Computers and computer programs which may be used or adapted for the purposes herein disclosed are commercially available. We have seen sufficient variation between the target organisms and the closest phylogenetic relative likely to be found in the same sample to design the present probes.

Merely identifying putatively unique potential target nucleotide sequences does not guarantee that a functionally species-specific hybridization assay probe may be made to hybridize to Borrelia rRNA or rDNA comprising that sequence. Various other factors will determine the suitability of a nucleic acid locus as a target site for species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art as described in Hogan et al., the same assignee as the present application and hereby incorporated by reference herein and Hogan and Hammond, U.S. Pat. No. 5,216,143, assigned to International Patent No. PCT/US87/03009, Kohne, U.S. Pat. No. 4,851,330.

By way of example: a higher GC content of the potential target nucleotide sequence (and thus of the double-stranded probe:target hybrid) generally increases the stability and thus the $T_m$ of the hybrid. The number of nucleotides within that sequence which are identical to one or more of the "unselected" organisms also affect the stability, and thus the $T_m$, of a partially mismatched hybrid between a probe perfectly complementary to Borrelia rRNA, and a nucleic acid having rRNA nucleotide sequences of the unselected organism or organisms.

The desired temperature of hybridization and the hybridization solution composition (such as salt concentration, detergents and other solutes) also greatly affects the stability of double-stranded hybrids. Conditions such as ionic strength and the temperature at which a probe will be allowed to hybridize to target must be taken into account in constructing a group- or species-specific probe. The thermal stability of hybrid nucleic acids generally increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize with their targets under conditions of high stringency. Under such conditions only single nucleic acid strands having a high degree of complementarity will hybridize to each other; single nucleic acid strands without such a high degree of complementarity will not form hybrids. Accordingly, the stringency of the assay conditions determines the amount of complementarity which should exist between two nucleic acid strands in order to form a hybrid. Stringency is chosen to maximize the difference in stability between the hybrid formed between the probe and the target nucleic acid and potential hybrids between the probe and any non-target nucleic acids present.

Proper specificity may be achieved by minimizing the length of the probe having perfect complementarity to sequences of non-target organisms, by avoiding G and C rich regions of homology to non-target sequences, and by constructing the probe to contain as many destabilizing mismatches to nontarget sequences as possible. Whether a probe sequence is useful to detect only a specific type of organism depends largely on the thermal stability difference between probe:target hybrids versus potential probe:nontarget hybrids. In designing probes, the differences in the $T_m$ values between these hybrids should be made as large as possible (preferably about 5° C. or more). Manipulation of the $T_m$, can be accomplished by changes to probe length and probe composition (GC content vs. AT content).

In general, the optimal hybridization temperature for oligonucleotide probes of about 10–50 nucleotides in length is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs.

A preferred method to determine $T_m$ measures hybridization using a Hybridization Protection Assay (HPA) according to Arnold et al., supra entitled "Homogenous Protection Assay". $T_m$ can be measured using HPA in the following manner. A probe:target hybrid is formed in lithium succinate buffered solution (0.1 M lithium succinate buffer, pH 5.0, 2 mM ethylenediamine tetraacetic acid (EDTA), 2 mM ethylene glycol-bis(β-amino-ethyl ether) N,N,N',N'-tetraacetic acid (EGTA), 10% (w/v) lithium lauryl sulfate) using an excess amount of target. Aliquots of the hybrid are then diluted in the lithium succinate buffered solution and incubated for five minutes at various temperatures starting below that of the anticipated $T_m$ (typically 55° C.) and increasing in 2–5° C. increments. This solution is then diluted with a mild alkaline borate buffer (0.15 M sodium tetraborate, pH 7.6, 5% (v/v) TRITON® X-100) and incubated at a lower temperature (for example 50° C.) for ten minutes. Under these conditions the acridinium ester attached to a single-stranded probe is hydrolyzed while the acridinium ester attached to hybridized probe is relatively protected from hydrolysis. Thus, the amount of acridinium ester remaining is proportional to the amount of hybrid and can be measured by the chemiluminescence produced from the acridinium ester upon the addition of hydrogen peroxide followed by alkali. Chemiluminescence can be measured in a luminometer (e.g., Gen-Probe LEADER® I or LEADER® 50). The resulting data are plotted as percent of maximum signal (usually from the lowest temperature) versus temperature. The $T_m$ is defined as the temperature at which 50% of the maximum signal remains. In addition to the method above, $T_m$ may be determined by isotopic methods well known to those skilled in the art (e.g., Hogan et al., supra).

It should be noted that the $T_m$ for a given hybrid varies depending on the hybridization solution used. Factors such as the salt concentration, detergents, and other solutes can affect hybrid stability during thermal denaturation (J. Sambrook, E. F. Fritsch and T. Maniatis, *Molecular Cloning*, ch. 11 (2d ed. 1989)). Conditions such as ionic strength and incubation temperature under which a probe will be used to hybridize to target should be taken into account in constructing a probe. On the other hand, chemical reagents which disrupt hydrogen bonds such as formamide, urea, dimethylsulfoxide and alcohols, can greatly reduce the thermal stability of the hybrids.

To ensure the probe is specific for its target, it is desirable to have probes which hybridize only under conditions of high stringency. Under conditions of high stringency only highly complementary nucleic acid hybrids will form; hybrids without a sufficient degree of complementarity will not form. Accordingly, the stringency of the assay conditions determines the amount of complementarity needed between two nucleic acid strands to form a hybrid. Stringency is chosen to maximize the difference in stability between the hybrid formed with the target and other nucleic acid sequences.

Proper specificity may be achieved by minimizing the length of perfect complementarity to non-target nucleic acids, avoiding G and C rich regions of homology to non-target sequences, and by constructing the probe to contain as many destabilizing mismatches to nontarget sequences as possible. Whether a probe sequence is useful to detect only a specific type of organism depends largely on the thermal stability difference between probe:target hybrids and probe:nontarget hybrids. In designing probes, the differences in these $T_m$ values should be as large as possible (preferably about 5° C. or more).

The length of the target nucleic acid sequence and, accordingly, the length of the probe sequence can also be important. In some cases, there may be several sequences from a particular region, for example, a variable region varying in location and length, which yield probes with the desired hybridization characteristics. In other cases, one probe may be significantly better than another probe with a nucleotide sequence differing by a single base. While it is possible for nucleic acids that are not perfectly complementary to hybridize, the longest stretch of perfectly homologous base sequence will generally determine hybrid stability, with the composition of the base pairs also playing a role.

The length of the target nucleic acid sequence, and accordingly the length of the probe sequence, can also be important. In some cases, there may be several sequences from a particular "variable" region, varying in location and length, which may be used to design probes with the desired hybridization characteristics.

Oligonucleotides used as probes in the present invention are of various lengths. Preferred probes are oligonucleotides that are 10 to 100 nucleotides in length. More preferred are probes of 15 to 50 bases in length.

Regions of rRNA which form strong internal structures inhibitory to hybridization are less preferred target regions at least assay in which helper probes are not used. Likewise, probe designs which result in extensive selfcomplementarity should be avoided. As explained above, hybridization is the association of two single strands of complementary nucleic acids to form a hydrogen-bonded double-stranded hybrid. Thus, if one of the two strands is wholly or partially involved in an intramolecular or intermolecular hybrid it will be less able to participate in the formation of a new intermolecular probe:target hybrid. Ribosomal RNA molecules are known to form very stable intramolecular helices and secondary structures by hydrogen bonding. By designing a hybridization assay so that a substantial portion of the targeted sequence remains in a single-stranded state until hybridization with the probe, the rate and extent of hybridization between probe and target may be greatly increased. One way this may be accomplished is by choosing as a target nucleotide sequence a sequence that is relatively uninvolved in intramolecular hydrogen-bonding. Alternatively or additionally, the hybridization assay probe may be used in a probe mix with helper oligonucleotides which can make the target site more accessible for hybridization with the hybridization assay probe.

A DNA target occurs naturally in a double-stranded form as does the product of the polymerase chain reaction (PCR). These double-stranded targets are naturally inhibitory to hybridization with a probe and require denaturation prior to hybridization. Appropriate denaturation and hybridization conditions are known in the art (e.g., E. M. Southern, *J. Mol. Bio.* 98:503 (1975)).

A number of formulae are available which will provide an estimate of the melting temperature for perfectly matched oligonucleotides to their target nucleic acids. One such formula, $$T_m = 81.5 + 16.6(\log_{10}[Na^+]) + 0.41(\text{fraction } G+C) - (600/N)$$

(where N=the length of the oligonucleotide in number of nucleotides) provides a good estimate for the $T_m$ for oligonucleotides between 14 and 60 or 70 nucleotides in length. From such calculations, subsequent empirical verification or "fine tuning" of the $T_m$ may be made using screening techniques well known in the art. For further information on hybridization and oligonucleotide probes see e.g., Sambrook et al., Molecular Cloning: A Laboratory Manual (Cold Springs Harbor Laboratory Press 1989) hereby incorporated by reference herein (at Chapter 11). This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Preferably, the amplification oligonucleotides of the present invention are oligodeoxynucleotides and are sufficiently long to be used as a substrate for the synthesis of extension products by a nucleic acid polymerase. Optimal primer length should take into account several factors, including the temperature of reaction, the structure and base composition of the primer, and how the primer is to be used. For example, for optimal specificity the oligonucleotide primer generally should contain at least about 12 nucleotides depending on the complexity of the target nucleic acid sequence. If such specificity is not essential, shorter primers may be used; in such a case, it may be desirable to carry out reaction at cooler temperatures in order to form stable hybrid complexes with the template nucleic acid.

Useful guidelines for designing amplification oligonucleotides and probes with desired characteristics are described herein. Our best mode design sites contain two and preferably three conserved regions of Lyme disease-associated Borrelia nucleic acid greater than about 15 bases within about 350 bases and preferably within 150 contiguous nucleotides of a single nucleic acid molecule.

The degree of amplification observed with a set of primers or promoter primers depends on several factors, including the ability of the oligonucleotides to hybridize to their complementary sequences and their ability to be extended or copied enzymatically. While oligonucleotides of different lengths and base composition may be used, oligonucleotides preferred in this invention have target binding regions of 18–40 bases with a predicted $T_m$ to target of about 65° C.

Parameters which affect hybridization of a probe such as $T_m$, complementarity and secondary structure of the target sequence also affect primer hybridization and therefore performance. The degree of non-specific extension (primer-dimer or non-target copying) can also affect amplification efficiency, therefore primers are selected to have low self- or cross-complementarity, particularly at the 3' ends of the sequence. Long homopolymer tracts and high GC content are avoided to reduce spurious primer extension. Computer programs are available to aid in this aspect of the design.

A nucleic acid polymerase used in conjunction with the amplification oligonucleotides of the present invention refers to a chemical, physical or biological agent which incorporates either ribo- or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the antiparallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilus* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly-synthesized template strand may be made available for hybridization with a second primer or promoter-primer through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification oligonucleotide, or both, may be a promoter-primer. Such a promoter-primer usually contains nucleotide sequences that are not complementary to those of the target nucleic acid molecule, or primer extension product(s). These non-complementary sequences may be located 5' to the complementary sequences on the amplification oligonucleotide, and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well unless the context of the reference clearly indicates otherwise.

In some amplification systems, for example the amplification method of Dattagupta et al., supra, the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' end to prevent enzymatic digestion. Alternatively, the nucleic acid polymerase may be modified to remove the 5' exonuclease activity, such as by treatment with a protease that generates an active polymerase fragment with no such nuclease activity. In such a case the oligonucleotides need not be modified at their 5' end.

1. Preparation of Oligonucleotides

An oligonucleotide is made of nucleotide subunits covalently joined together. The sugar groups of the nucleotide subunits may be ribose, deoxyribose, or modified derivatives thereof such as O-methyl ribose. The nucleotide subunits may be joined by linkages such as phosphodiester linkages, modified linkages, or by non-nucleotide moieties that do not prevent hybridization of the oligonucleotide. Modified linkages include those linkages in which a standard phosphodiester linkage is replaced with a different linkage, such as a phosphorothioate linkage or methylphosphonate linkage. As mentioned above, when used as a hybridization assay probe the oligonucleotide preferably contains a reporter group such as an acridinium ester or a radioisotope to help identify hybridization of the probe to its target sequence.

All of the amplification oligonucleotides of the present invention can be readily prepared by methods known in the art. Preferably, the primers are synthesized using solid phase methods. For example, Carruthers, et al., describe using standard phosphoramidite solid phase chemistry to join nucleotides by phosphodiester linkages. Automated solid-phase chemical synthesis using cyanoethyl phosphoramidite precursors has been described by Barone, et al., *Nucleic Acids Research,* 12:405 (1984). (*Methods in Enzymology,* Volume 143, pg. 287 (1987)). Likewise, Bhatt describes a procedure for synthesizing oligonucleotides containing phosphorothioate linkages. (U.S. patent application Ser. No. 07/319,570, entitled "Method and Reagent for Sulphurization of Organophosphorous Compounds", which enjoys common ownership with the present invention.) Also, Klem et al., entitled "Improved Process for the Synthesis of Oligomers", PCT WO 92/07864, describe the synthesis of oligonucleotides having different linkages including methylphosphonate linkages. The latter three references are hereby incorporated by reference herein. In addition, methods for the organic synthesis of oligonucleotides are known to those of skill in the art, and are described in Sambrook, et al., supra, previously incorporated by reference herein.

Following synthesis and purification of a particular oligonucleotide, several different procedures may be utilized to determine the acceptability of the probe or primer in terms of size and purity. Suitable procedures include polyacrylamide gel electrophoresis or high pressure liquid chromatography. Both of these procedures are well known to those skilled in the art.

All of the oligonucleotides of the present invention, whether hybridization assay probes, amplification oligonucleotides, or helper oligonucleotides, may be modified with chemical groups to enhance their performance or to facilitate the characterization of amplification products. For example, backbone-modified oligonucleotides such as those having phosphorothioate or methylphosphonate groups which render the oligonucleotides resistant to the nucleolytic activity of certain polymerases may allow the use of such enzymes in an amplification or other reaction. Another example of modification involves using non-nucleotide linkers (e.g., Arnold, et al., "Non-Nucleotide Linking Reagents for Nucleotide Probes", European patent application 88308766-0, hereby incorporated by reference herein) incorporated between nucleotides in the nucleic acid chain which do not interfere with hybridization or the elongation of the primer. Amplification oligonucleotides may also contain mixtures of the desired modified and natural nucleotides.

The 3' end of an amplification oligonucleotide may be blocked to prevent initiation of DNA synthesis as described by McDonough, et al., entitled "Nucleic Acid Sequence Amplification", U.S. application Ser. No. 07/925,405 which enjoys common ownership with the present invention and is hereby incorporated by reference herein. A mixture of different 3' blocked amplification oligonucleotides, or of 3' blocked and unblocked oligonucleotides may increase the efficiency of nucleic acid amplification, as described therein.

As disclosed above, the 5' end of the oligonucleotides may be modified to be resistant to the 5'-exonuclease activity present in some nucleic acid polymerases. Such modifications can be carried out by adding a non-nucleotide group to the terminal 5' nucleotide of the primer using techniques such as those described by Arnold, et al., supra, entitled "Non-Nucleotide Linking Reagents for Nucleotide Probes", previously incorporated by reference herein.

Once synthesized, selected oligonucleotide probes may be labeled by any of several well known methods (e.g., J. Sambrook, supra). Useful labels include radioisotopes as well as non-radioactive reporting groups. Isotopic labels include $^{3}$H, $^{35}$S, $^{32}$P, $^{125}$I, $^{57}$Co and $^{14}$C. Isotopic labels can be introduced into the oligonucleotide by techniques known in the art such as nick translation, end labeling, second strand synthesis, the use of reverse transcription, and by chemical methods. When using radiolabeled probes hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as described by Arnold, et al., entitled "Non-Nucleotide Linking Reagents for Nucleotide Probes", EPO application number 88308766.0, publication number 313219, hereby incorporated by reference herein. Non-isotopic labels include fluorescent molecules, chemiluminescent molecules, enzymes, cofactors, enzyme substrates, haptens or other ligands.

Preferably, the probes are labeled with an acridinium ester. Acridinium ester labeling may be performed as described by Arnold et al., U.S. Pat. No. 5,185,439, entitled "Acridinium Ester Labeling and Purification of Nucleotide Probes" issued Feb. 9, 1993 and hereby incorporated by reference herein.

2. Amplification of Borrelia rRNA and rDNA

The amplification oligonucleotides of the present invention are directed to particular Borrelia 16S or 23S rRNA nucleotide sequences, or their rDNA counterparts. These amplification oligonucleotides may be flanking or contained within at least one of the target nucleotide sequences used as a hybridization assay probe to detect the presence of Borrelia in a nucleic acid amplification assay. The amplification oligonucleotides described and claimed herein comprise two sets of amplification oligonucleotides. Members of the set of amplification oligonucleotides are able to hybridize with a nucleic acid having or substantially corresponding to one of the following nucleotide sequences:

SEQ ID NO 36: ACGCTAAACCCTTACGTATTACCGCGGCT,
SEQ ID NO 37: TATGTTGGAAACTATATGTCTAGAGTCTGATAGAGGAAG,
SEQ ID NO 38: TGATAGAGGAAGTTAGAATTTCTGGTGTAAGGGTGG,
SEQ ID NO 39: ACGCTCGCCCCTTACGTATTACCGCGGCT,
SEQ ID NO 40: CCCGTTTCCCATCGACTACACTTTTCAG,
SEQ ID NO 41: GAGCTAAGATGTGATGATGAGTGC,
SEQ ID NO 42: CGTTAAGGAACTCTGCAAAATACG,
SEQ ID NO 51: ACGCUAAACCCUUACGUAUUACCGCGGCU,
SEQ ID NO 52: UAUGUUGGAAACUAUAUGUCUAGAGUCUGAUAGAGGAAG,
SEQ ID NO 53: UGAUAGAGGAAGUUAGAAUUUCUGGUGUAAGGGUGG,
SEQ ID NO 54: ACGCUCGCCCCUUACGUAUUACCGCGGCU,
SEQ ID NO 55: CCCGUUUCCCAUCGACUACACUUUUCAG,
SEQ ID NO 56: GAGCUAAGAUGUGAUGAUGAGUGC,
SEQ ID NO 27: TTAATGCTTAAACTAGGACAACCATCG,
SEQ ID NO 57: CGUUAAGGAACUCUGCAAAAUACG, and
SEQ ID NO 29: UUAAUGCUUAAACUAGGACAACCAUCG.

In preferred embodiments, these amplification oligonucleotides have or substantially correspond to the following sequences:

SEQ ID NO 7: AGCCGCGGTAATACGTAAGGGTTTAGCGT,
SEQ ID NO 9: CCACCCTTACACCAGAAATTCTAACTTCCTCTATCA,
SEQ ID NO 11: AGCCGCGGTAATACGTAAGGGGCGAGCGT,
SEQ ID NO 18: CTGAAAAGTGTAGTCGATGGGAAACGGG,
SEQ ID NO 19: GCACTCATCATCACATCTTAGCTC,
SEQ ID NO 20: CGTATTTTGCAGAGTTCCTTAACG,
SEQ ID NO 23: CGATGGTTGTCCTAGTTTAAGCATTAA,
SEQ ID NO 44: AGCCGCGGUAAUACGUAAGGGUUUAGCGU,
SEQ ID NO 45: CUUCCUCUAUCAGACUCUAGACAUAUAGUUUCCAACAUA,
SEQ ID NO 46: CCACCCUUACACCAGAAAUUCUAACUUCCUCUAUCA,
SEQ ID NO 47: AGCCGCGGUAAUACGUAAGGGGCGAGCGU,
SEQ ID NO 48: CUGAAAAGUGUAGUCGAUGGGAAACGGG,
SEQ ID NO 49: GCACUCAUCAUCACAUCUUAGCUC,
SEQ ID NO 50: CGUAUUUUGCAGAGUUCCUUAACG, and
SEQ ID NO 28: CGAUGGUUGUCCUAGUUUAAGCAUAA.

These oligonucleotides may also have additional, non-complementary bases at their 5' end comprising a promoter sequence able to bind an RNA polymerase and direct RNA transcription using the target nucleic acid as a template.

Preferred amplification primers directed to the 16S rRNA of Borrelia have or substantially correspond to the following nucleic acid sequences:

SEQ ID NO 7: AGCCGCGGTAATACGTAAGGGTTTAGCGT,
SEQ ID NO 9: CCACCCTTACACCAGAAATTCTAACTTCCTCTATCA,
SEQ ID NO 11: AGCCGCGGTAATACGTAAGGGGCGAGCGT,
SEQ ID NO 44: AGCCGCGGUAAUACGUAAGGGUUUAGCGU,
SEQ ID NO 46: CCACCCUUACACCAGAAAUUCUAACUUCCUCUAUCA, and
SEQ ID NO 47: AGCCGCGGUAAUACGUAAGGGGCGAGCGU.

These 16S rRNA amplification oligonucleotides can be directed to a particular Borrelia 16S rRNA nucleic acid sequence, rDNA counterparts, and overlapping partially or completely with these sequences.

Also preferred are 16S amplification oligonucleotides having a nucleotide sequence substantially corresponding to the nucleotide sequence:

SEQ ID NO 8: CTTCCTCTATCAGACTCTAGACATATAGTTTCCAACATA.

Most preferred are 16S amplification oligonucleotides having a nucleotide sequence substantially corresponding to the nucleotide sequence

SEQ ID NO 8: CTTCCTCTATCAGACTCTAGACATATAGTTTCCAACATA wherein the 19 3' most nucleotide are exactly as shown.

Preferred amplification primers directed to the 23S rRNA of Borrelia have or substantially correspond to the following nucleic acid sequences:
SEQ ID NO 18: CTGAAAAGTGTAGTCGATGGGAAACGGG,
SEQ ID NO 19: GCACTCATCATCACATCTTAGCTC,
SEQ ID NO 20: CGTATTTTGCAGAGTTCCTTAACG,
SEQ ID NO 48: CUGAAAAGUGUAGUCGAUGGGAAACGGG,
SEQ ID NO 49: GCACUCAUCAUCACAUCUUAGCUC, and
SEQ ID NO 50: CGUAUUUUGCAGAGUUCCUUAACG.

These 23S rRNA amplification oligonucleotides can be directed to a particular Borrelia 23S rRNA nucleic acid sequence, rDNA counterparts, and overlapping partially or completely with these sequences.

All of the amplification oligonucleotides of the present invention may have sequences which do not contain modifications or additions to these sequences. The amplification oligonucleotides may also or alternatively have modifications, such as blocked 3' and/or 5' termini or additions including but not limited to the addition of a specific nucleotide sequence that is recognized by an RNA polymerase, (e.g., the promoter sequence for T7, T3, or SP6 RNA polymerase), addition of sequences which enhance initiation or elongation of RNA transcription by an RNA polymerase, or sequences which may provide for intramolecular base pairing and encourage the formation of secondary or tertiary nucleic acid structures.

Amplification oligonucleotides are used in a nucleic acid amplification procedure, such as the polymerase chain reaction or an amplification reaction using RNA polymerase, DNA polymerase and RNAse H or its equivalent, as described by Kacian and Fultz supra, Dattagupta et al., supra, and by Sninsky et al., U.S. Pat. No. 5,079,351; both hereby incorporated by reference herein, the first two of which enjoy common ownership with the present invention.

A wide variety of methods are available to detect an amplified target sequence. For example, the nucleotide substrates or the primers can include a detectable label which is incorporated into newly synthesized DNA. The resulting labeled amplification product is then separated from the unused labeled nucleotides or primers and the label is detected in the separated product fraction.

Substances which can serve as useful detectable labels are well known in the art and include radioactive isotopes, fluorescent compounds, chemiluminescent compounds, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled nucleic acid probe and measuring the resulting hybrids in any conventional manner. In particular, the product can be assayed by hybridizing a chemiluminescent acridinium ester-labeled nucleic acid probe to the target sequence, selectively hydrolyzing the acridinium ester present on unhybridized probe, and measuring the chemiluminescence produced from the remaining acridinium ester in a luminometer. (see, e.g., Arnold, et al., supra, PCT Application No. US88/02746, and Nelson, et al., "Non-Isotopic DNA Probe Technologies", Academic Press, San Diego (Kricka, ed. 1992) both references hereby incorporated by reference herein.)

D. Oligonucleotide Hybridization Assay Probes to Borrelia rRNA and rDNA

The oligonucleotide hybridization assay probes disclosed and claimed herein are able to preferentially hybridize to target nucleic acids containing Lyme disease-associated Borrelia rRNA or rDNA nucleotide sequences over nucleic acids of phylogenetically closely related bacterial species. These hybridization assay probes were designed, selected and/or chosen based upon a comparison of the nucleotide sequences of corresponding regions of the ribosomal RNA of Lyme disease-associated Borrelia and said phylogenetically closely-related species. In preferred embodiments these probes selectively hybridize to the nucleic acids of Lyme disease-associated Borrelia over the nucleic acids of *Borrelia hermsii*.

The present invention contemplates oligonucleotide hybridization probes that selectively hybridize to the nucleic acids of Borrelia species including Lyme disease-associated Borrelia or *Borrelia hermsii* and not to the nucleic acids of closely related microorganisms and include nucleic acid sequences having or substantially corresponding to the following nucleic acid sequences:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG,
SEQ ID NO 26: CGGAUUUUCCUAUCAAGAUCAUCACC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

The hybridization assay probes of the present invention that selectively hybridize to the nucleic acid of Lyme disease-associated Borrelia have or substantially correspond to the following nucleotide sequences:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG, and
SEQ ID NO 26: CGGAUUUUCCUAUCAAGAUCAUCACC.

Currently, preferred embodiments of these oligonucleotide hybridization assay probes that are directed to 16S rRNA of Lyme disease-associated Borrelia have or substantially correspond to the nucleotide sequences:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC, and
SEQ ID NO 13: GGCGGAUAUAUAAGUCUAUGC.

Preferred embodiments of these oligonucleotide hybridization assay probes that are directed to 23S rRNA of Lyme disease-associated Borrelia have or substantially correspond to the nucleotide sequence:
SEQ ID NO 21: GGTGATGATCTTGATAGGAAAATCCG, SEQ ID NO 24: CGGATTTTCCTATCAAGATCATCACC,
SEQ ID NO 25: GGUGAUGAUCUUGAUAGGAAAAUCCG, and
SEQ ID NO 26: CGGAUUUUCCUAUCAAGAUCAUCACC.

A number of oligonucleotide hybridization assay probes of the present invention preferably hybridize to target nucleic acids containing *Borrelia hermsii* rRNA or rDNA nucleotide sequences over nucleic acids of other phylogenetically closely related bacterial species. In preferred embodiments, these hybridization assay probes can distinguish *Borrelia hermsii* nucleic acids from other Borrelia nucleic acids.

The hybridization probes of the present invention that selectively hybridize to nucleic acids derived from *Borrelia hermsii* have or substantially correspond to the following nucleotide sequences:

SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

Preferred embodiments of these oligonucleotide hybridization assay probes that are directed to 16S rRNA of *Borrelia hermsii* have or substantially correspond to the nucleotide sequences:

SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC, and
SEQ ID NO 35: GCAUAGACUUGCAUAUCCGCC.

Preferred embodiments of these oligonucleotide hybridization assay probes that are directed to 23S rRNA of *Borrelia hermsii* have or substantially correspond to the nucleotide sequences:

SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

The oligonucleotide hybridization assay probes of the present invention are preferably labeled with a reporter group moiety such as a radioisotope, a fluorescent or chemiluminescent moiety, with an enzyme or other ligand, which can be used for detection or confirmation that the probe has hybridized to the target sequence. The Applicant most prefers the use of chemiluminescent acridinium esters as labels. See Arnold et al., U.S. Pat. No. 5,185,439, which enjoys common ownership with the present application and is incorporated by reference herein. The assay probe is mixed with a sample suspected of containing a nucleic acid having the target sequence under hybridization conditions suitable for allowing annealing of the two strands by hydrogen bonding in the region of complementarity. The probe may also be combined with one or more unlabeled helper oligonucleotides to facilitate binding to the nucleic acid having the target Borrelia nucleotide sequence. The probe then hybridizes to the target nucleic acid present in the sample; the resulting hybrid duplex may be separated and detected by various techniques well known in the art, such as hydroxyapatite adsorption and radioactive monitoring. Also included among these techniques are those that involve selectively degrading the label present on unhybridized probe and then measuring the amount of label associated with the remaining hybridized probe, as disclosed in Arnold et al., U.S. Pat. No. 5,283,174, which enjoys common ownership with the present application and is incorporated by reference herein. This latter technique is presently preferred by the Applicants.

E. Helper Oligonucleotides Used in the Detection of Borrelia

Specific helper oligonucleotides were used to facilitate the hybridization of the hybridization assay probes to the target nucleic acid. Helper oligonucleotides are described in Hogan and Milliman, U.S. Pat. No. 5,030,557 entitled *Means and Method for Enhancing Nucleic Acid Hybridization*, which enjoys common ownership with the present application and is hereby incorporated by reference herein.

Helper probes are selected to hybridize to nucleic acid sequences located near the region targeted by the hybridization assay probe. Hybridization of the helper probe alters the secondary and tertiary structure of the target nucleic acid, facilitating the hybridization of the probe to the target nucleic acid.

Specific helper oligonucleotides for facilitating the specific detection of Borrelia nucleic acids have or substantially correspond to one of these nucleotide sequences:

SEQ ID NO 4: CGGGATTATTGGGCGTAAAGGGTGAGTA,
SEQ ID NO 6: ATAAAATACCACAGCTCAACTGTGGACCTATGTTGG,
SEQ ID NO 15: CGGGAUUAUUGGGCGUAAAGGGUGAGUA,
SEQ ID NO 17: AUAAAAUACCACAGCUCAACUGUGGACCUAUGUUGG,
SEQ ID NO 23: CGATGGTTGTCCTAGTTTAAGCATTAA, and
SEQ ID NO 28: CGAUGGUUGUCCUAGUUUAAGCAUUAA.

In other embodiments specific helper oligonucleotides for facilitating the specific detection of Borrelia nucleic acid have or substantially correspond to one of the following nucleotide sequences:

SEQ ID NO 3: TACTCACCCTTTACGCCCAATAATCCCG,
SEQ ID NO 5: CCAACATAGGTCCACAGTTGAGCTGTGGTATTTTAT,
SEQ ID NO 14: UACUCACCCUUUACGCCCAAUAAUCCCG,
SEQ ID NO 16: CCAACAUAGGUCCACAGUUGAGCUGUGGUAUUUUAU,
SEQ ID NO 27: TTAATGCTTAAACTAGGACAACCATCG, and
SEQ ID NO 29: UUAAUGCUUAAACUAGGACAACCAUCG.

In preferred embodiments, a hybridization assay probe directed to Lyme disease-associated Borrelia 16S ribosomal nucleic acids is used in a probe mixture together with a helper oligonucleotide having or substantially corresponding to a nucleotide sequence of:

SEQ ID NO 3: TACTCACCCTTTACGCCCAATAATCCCG,
SEQ ID NO 4: CGGGATTATTGGGCGTAAAGGGTGAGTA,
SEQ ID NO 5: CCAACATAGGTCCACAGTTGAGCTGTGGTATTTTAT,
SEQ ID NO 6: ATAAAATACCACAGCTCAACTGTGGACCTATGTTGG,

SEQ ID NO 14: UACUCACCCUUUACGCCCAAUAAUCCCG,
SEQ ID NO 15: CGGGAUUAUUGGGCGUAAAGGGUGAGUA,
SEQ ID NO 16: CCAACAUAGGUCCACAGUUGAGCUGUGGUAUUUUAU, and
SEQ ID NO 17: AUAAAAUACCACAGCUCAACUGUGGACCUAUGUUGG.

In the most preferred embodiment, the hybridization probe directed to Lyme disease-associated Borrelia 16S substantially corresponding to
SEQ ID NO 2: GGCGGATATATAAGTCTATGC
ribosomal nucleic acids is used in a probe mixture together with a helper oligonucleotide having or substantially corresponding to the nucleotide sequence of:
SEQ ID NO 4: CGGGATTATTGGGCGTAAAGGGTGAGTA,
SEQ ID NO 6: ATAAAATACCACAGCTCAACTGTGGACCTATGTTGG
SEQ ID NO 15: CGGGAUUAUUGGGCGUAAAGGGUGAGUA, and
SEQ ID NO 17: AUAAAAUACCACAGCUCAACUGUGGACCUAUGUUGG.

In the most preferred embodiment, the hybridization probe directed to Lyme disease-associated Borrelia 16S ribosomal nucleic acids substantially correspond to
SEQ ID NO 1: GCATAGACTTATATATCCGCC
is used in a probe mixture together with a helper oligonucleotide having or substantially corresponding to the nucleotide sequence of:
SEQ ID NO 3: TACTCACCCTTTACGCCCAATAATCCCG,
SEQ ID NO 5: CCAACATAGGTCCACAGTTGAGCTGTGGTATTTTAT,
SEQ ID NO 14: UACUCACCCUUUACGCCCAAUAAUCCCG, and
SEQ ID NO 16: CCAACAUAGGUCCACAGUUGAGCUGUGGUAUUUUAU.

In preferred embodiments, a hybridization assay probe directed to Lyme disease-associated Borrelia 23S nucleic acids is used in a probe mixture together with a helper oligonucleotide having or substantially corresponding to a nucleotide sequence of:
SEQ ID NO 23: CGATGGTTGTCCTAGTTTAAGCATTAA,
SEQ ID NO 27: TTAATGCTTAAACTAGGACAACCATCG,
SEQ ID NO 28: CGAUGGUUGUCCUAGUUUAAGCAUUAA, and
SEQ ID NO 29: UUAAUGCUUAAACUAGGACAACCAUCG.

In the most preferred embodiment, a hybridization probe directed to Lyme disease-associated Borrelia 23S ribosomal nucleic acid substantially corresponding to
SEQ ID NO 21: GGTGATGATCTTGATAGGAAAATCCG
is used in a mixture together with a helper oligonucleotide having or substantially corresponding to the nucleotide sequence of:
SEQ ID NO 23: CGATGGTTGTCCTAGTTTAAGCATTAA, and
SEQ ID NO 28: CGAUGGUUGUCCUAGUUUAAGCAUUAA.

In preferred embodiments, a hybridization probe directed to *Borrelia hermsii* 16S ribosomal nucleic acids substantially corresponding to SEQ ID No. 10 or SEQ ID No. 33 is used in a probe mixture together with a helper oligonucleotide having or substantially corresponding to a nucleotide sequence of:
SEQ ID NO 5: CCAACATAGGTCCACAGTTGAGCTGTGGTATTTTAT,
SEQ ID NO 6: ATAAAATACCACAGCTCAACTGTGGACCTATGTTGG,
SEQ ID NO 16: CCAACAUAGGUCCACAGUUGAGCUGUGGUAUUUUAU, and
SEQ ID NO 17: AUAAAAUACCACAGCUCAACUGUGGACCUAUGUUGG.

In preferred embodiments, a hybridization probe directed to *Borrelia hermsii* 16S ribosomal nucleic acids substantially corresponding to
SEQ ID NO 10: GGCGGATATGCAAGTCTATGC
is used in a probe mixture together with a helper oligonucleotide having or substantially corresponding to a nucleotide sequence of:
SEQ ID NO 6: ATAAAATACCACAGCTCAACTGTGGACCTATGTTGG, and
SEQ ID NO 17: AUAAAAUACCACAGCUCAACUGUGGACCUAUGUUGG.

In preferred embodiments, a hybridization probe directed to *Borrelia hermsii* 23S ribosomal nucleic acids is used in a probe mixture together with a helper oligonucleotide having or substantially corresponding to a nucleotide sequence of:
SEQ ID NO 23: CGATGGTTGTCCTAGTTTAAGCATTAA,
SEQ ID NO 27: TTAATGCTTAAACTAGGACAACCATCG,
SEQ ID NO 28: CGAUGGUUGUCCUAGUUUAAGCAUUAA, and
SEQ ID NO 29: UUAAUGCUUAAACUAGGACAACCAUCG.

In preferred embodiments, a hybridization probe directed to *Borrelia hermsii* 23S ribosomal nucleic acids substantially corresponding to
SEQ ID NO 22: GGTGTTGATTTTAGTAGGAAAATCCG
is used in a probe mixture together with a helper oligonucleotide having or substantially corresponding to a nucleotide sequence of:
SEQ ID NO 23: CGATGGTTGTCCTAGTTTAAGCATTAA, and
SEQ ID NO 28: CGAUGGUUGUCCUAGUUUAAGCAUUAA Helper oligonucleotides generally may be used under stringent hybridization conditions, but are not necessarily species specific in the selectivity; i.e., the target nucleotide sequences for the helper oligonucleotides are not necessarily unique to the species Borrelia.

F. Nucleic Acid Compositions

In another related aspect, the invention features compositions comprising a nucleic acid hybrid between a hybridization assay probe and a nucleic acid sequence substantially complementary thereto (probe:target). One use of the hybrid formed between probe and target is to detect the presence of a target sequence. For example, acridinium ester ("AE") present in hybrids is resistant to hydrolysis in alkali solution whereas AE present in single-stranded nucleic acid is hydrolyzed in alkali solution (Arnold et al., entitled "Homogenous Protection Assay," EPO application number 88308767.8, publication number 309230, and by U.S. Pat. No. 5,238,174 hereby incorporated by reference). Thus, presence of target nucleic acids can be detected, after hydrolysis of the unbound AE-labeled probe, by measuring chemiluminescence of acridinium ester remaining associated with the nucleic acid hybrid.

The present invention also contemplates compositions comprising a nucleic acid hybrid between an amplification oligonucleotide and a nucleic acid sequence substantially complementary thereto (primer:target). One use the nucleic acid hybrid formed between primer and target is to provide an initiation site for a polymerase at the 3' end of the amplification oligonucleotide. For example, hybrids may form an initiation site for reverse transcriptase, DNA polymerases such as Taq polymerase or T4 DNA polymerase and RNA polymerases such as, T7 polymerase, SP6 polymerase, T3 polymerases and the like.

The present invention also features compositions comprising nucleic acid hybrids between a helper oligonucleotide and a nucleic acid sequence substantially complementary thereto (helper oligonucleotide:target). One use of the hybrid between the helper oligonucleotide and target is to make available a particular nucleic acid sequence for hybridization. For example, a hybrid between a helper oligonucleotide and its target may make a nucleic acid sequence capable of hybridizing to the target sequence available for hybridization with a hybridization probe. A full description of the use of helper oligonucleotides is provided in Hogan and Milliman, U.S. Pat. No. 5,030,557.

Compositions of the present invention include compositions for detecting Borrelia nucleic acid comprising a nucleic acid hybrid formed between a Borrelia nucleic acid and an oligonucleotide having a nucleic acid sequence substantially corresponding to at least one of the nucleic acid sequences that follows:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG,
SEQ ID NO 26: CGGAUUUUCCUAUCAAGAUCAUCACC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG,
SEQ ID NO 32: CGGAUUUUCCUACUAAAAUCAACACC,
SEQ ID NO 7: AGCCGCGGTAATACGTAAGGGTTTAGCGT,
SEQ ID NO 8: CTTCCTCTATCAGACTCTAGACATATAGTTTCCAACATA,
SEQ ID NO 9: CCACCCTTACACCAGAAATTCTAACTTCCTCTATCA,
SEQ ID NO 11: AGCCGCGGTAATACGTAAGGGGCGAGCGT,
SEQ ID NO 18: CTGAAAAGTGTAGTCGATGGGAAACGGG,
SEQ ID NO 19: GCACTCATCATCACATCTTAGCTC,
SEQ ID NO 20: CGTATTTTGCAGAGTTCCTTAACG,
SEQ ID NO 44: AGCCGCGGUAAUACGUAAGGGUUUAGCGU,
SEQ ID NO 45: CUUCCUCUAUCAGACUCUAGACAUAUAGUUUCCAACAUA,
SEQ ID NO 46: CCACCCUUACACCAGAAAUUCUAACUUCCUCUAUCA,
SEQ ID NO 47: AGCCGCGGUAAUACGUAAGGGGCGAGCGU,
SEQ ID NO 48: CUGAAAAGUGUAGUCGAUGGGAAACGGG,
SEQ ID NO 49: GCACUCAUCAUCACAUCUUAGCUC, and
SEQ ID NO 50: CGUAUUUUGCAGAGUUCCUUAACG.

Preferred compositions of the present invention include compositions for detecting Lyme disease-associated Borrelia comprising a nucleic acid hybrid formed between a Borrelia nucleic acid and an oligonucleotide having a nucleic acid sequence substantially corresponding to at least one of the nucleic acid sequences that follows:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG,
SEQ ID NO 26: CGGAUUUUCCUAUCAAGAUCAUCACC,
SEQ ID NO 7: AGCCGCGGTAATACGTAAGGGTTTAGCGT,
SEQ ID NO 8: CTTCCTCTATCAGACTCTAGACATATAGTTTCCAACATA,
SEQ ID NO 9: CCACCCTTACACCAGAAATTCTAACTTCCTCTATCA,
SEQ ID NO 18: CTGAAAAGTGTAGTCGATGGGAAACGGG,
SEQ ID NO 19: GCACTCATCATCACATCTTAGCTC,
SEQ ID NO 20: CGTATTTTGCAGAGTTCCTTAACG,
SEQ ID NO 44: AGCCGCGGUAAUACGUAAGGGUUUAGCGU,
SEQ ID NO 45: CUUCCUCUAUCAGACUCUAGACAUAUAGUUUCCAACAUA,
SEQ ID NO 46: CCACCCUUACACCAGAAAUUCUAACUUCCUCUAUCA,
SEQ ID NO 48: CUGAAAAGUGUAGUCGAUGGGAAACGGG,
SEQ ID NO 49: GCACUCAUCAUCACAUCUUAGCUC, and
SEQ ID NO 50: CGUAUUUUGCAGAGUUCCUUAACG.

Preferred compositions of the present invention include compositions for detecting Lyme disease-associated Borrelia comprising a nucleic acid hybrid formed between a Borrelia nucleic acid and an oligonucleotide having a nucleic acid sequence substantially corresponding to at least one of the nucleic acid sequences that follows:
SEQ ID NO 1: GCATAGACTTATATATCCGCC,
SEQ ID NO 2: GGCGGATATATAAGTCTATGC,
SEQ ID NO 21: GGTGATGATCTTGATAGGAAAATCCG,
SEQ ID NO 7: AGCCGCGGTAATACGTAAGGGTTTAGCGT,
SEQ ID NO 9: CCACCCTTACACCAGAAATTCTAACTTCCTCTATCA, SEQ ID NO 18: CTGAAAAGTGTAGTCGATGGGAAACGGG,
SEQ ID NO 19: GCACTCATCATCACATCTTAGCTC, and
SEQ ID NO 20: CGTATTTTGCAGAGTTCCTTAACG.

The present invention also contemplates compositions for detecting Lyme disease-associated Borrelia comprising a nucleic acid hybrid formed between a Borrelia nucleic acid and an oligonucleotide having a nucleic acid sequence substantially corresponding to
SEQ ID NO 7: AGCCGCGGTAATACGTAAGGGTTAGCGT
and which also has an oligonucleotide having a nucleic acid sequence substantially corresponding to at least one nucleic acid sequence that follows:
SEQ ID NO 8: CTTCCTCTATCAGACTCTAGACATATAGTTTCCAACATA, and
SEQ ID NO 9: CCACCCTTACACCAGAAATTCTAACTCCTCTATCA.

The present invention also contemplates compositions for detecting Lyme disease-associated Borrelia having a nucleic acid hybrid formed between a Borrelia nucleic acid and an oligonucleotide having a nucleic acid sequence substantially corresponding to:
SEQ ID NO 44: AGCCGCGGUAAUACGUAAGGGUUUAGCGU,
and which also has an oligonucleotide having a nucleic acid sequence substantially corresponding to at least one nucleic acid sequence
SEQ ID NO 45: CUUCCUCUAUCAGACUCUAGACAUAUAGUUUCCAACAUA, or
SEQ ID NO 46: CCACCCUUACACCAGAAAUUCUAACUUCCUCUAUCA.

Preferred compositions of the present invention include compositions for detecting Borrelia hermsii comprising a nucleic acid hybrid formed between a Borrelia hermsii nucleic acid and an oligonucleotide having a nucleic acid sequence substantially corresponding to at least one of the nucleic acid sequences that follow:
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 7: AGCCGCGGTAATACGTAAGGGTTTAGCGT,
SEQ ID NO 11: AGCCGCGGTAATACGTAAGGGGCGAGCGT,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG,
SEQ ID NO 32: CGGAUUUCCUACUAAAAUCAACACC,
SEQ ID NO 18: CTGAAAAGTGTAGTCGATGGGAAACGGG,
SEQ ID NO 19: GCACTCATCATCACATCTTAGCTC,
SEQ ID NO 48: CUGAAAAGUGUAGUCGAUGGGAAACGGG, and
SEQ ID NO 49: GCACUCAUCAUCACAUCUUAGCUC.

More preferred compositions of the present invention include compositions for detecting Borrelia hermsii comprising a nucleic acid hybrid formed between a Borrelia hermsii nucleic acid and an oligonucleotide having a nucleic acid sequence substantially corresponding to at least one of the nucleic acid sequences that follow:
SEQ ID NO 10: GGCGGATATGCAAGTCTATGC,
SEQ ID NO 22: GGTGTTGATTTTAGTAGGAAAATCCG,
SEQ ID NO 7: AGCCGCGGTAATACGTAAGGGTTTAGCGT,
SEQ ID NO 11: AGCCGCGGTAATACGTAAGGGGCGAGCGT,
SEQ ID NO 18: CTGAAAAGTGTAGTCGATGGGAAACGGG, and
SEQ ID NO 19: GCACTCATCATCACATCTTAGCTC.

The present invention also contemplates compositions for detecting Borrelia hermsii having a nucleic acid hybrid formed between a Borrelia hermsii nucleic acid and an oligonucleotide having a nucleic acid sequence substantially corresponding to
SEQ ID NO 8: CTTCCTCTATCAGACTCTAGACATATAGTTTCCAACATA
and which also has an oligonucleotide having nucleic acid sequence substantially corresponding to at least one nucleic acid sequence that follows:
SEQ ID NO 7: AGCCGCGGTAATACGTAAGGGTTTAGCGT
SEQ ID NO 11: AGCCGCGGTAATACGTAAGGGGCGAGCGT The present invention also contemplates compositions for detecting Borrelia hermsii having a nucleic acid hybrid formed between a Borrelia hermsii nucleic acid and an oligonucleotide having a nucleic acid sequence substantially corresponding to
SEQ ID NO 45: CUUCCUCUAUCAGACUCUAGACAUAUAGUUUCCAACAUA
and which also has an oligonucleotide having a nucleic acid sequence substantially corresponding to at least one nucleic acid sequence that follows:
SEQ ID NO 44: AGCCGCGGUAAUACGUAAGGGUUUAGCGU
SEQ ID NO 47: AGCCGCGGUAAUACGUAAGGGGCGAGCGU The present invention also contemplates nucleic acid hybrids comprising probes of the present invention and also at least one helper oligonucleotide that has a nucleic acid sequence substantially corresponding to at least one of the nucleic acid sequences that follows:
SEQ ID NO 3: TACTCACCCTTTACGCCCAATAATCCCG,
SEQ ID NO 4: CGGGATTATTGGGCGTAAAGGGTGAGTA,
SEQ ID NO 5: CCAACATAGGTCCACAGTTGAGCTGTGGTATTTTAT,
SEQ ID NO 6: ATAAAATACCACAGCTCAACTGTGGACCTATGTTGG,
SEQ ID NO 14: UACUCACCCUUUACGCCCAAUAAUCCCG,
SEQ ID NO 15: CGGGAUUAUUGGGCGUAAAGGGUGAGUA,
SEQ ID NO 16: CCAACAUAGGUCCACAGUUGAGCUGUGGUAUUUAU,
SEQ ID NO 17: AUAAAAUACCACAGCUCAACUGUGGACCUAUGUUGG,
SEQ ID NO 23: CGATGGTTGTCCTAGTTTAAGCATTAA,
SEQ ID NO 27: TTAATGCTTAAACTAGGACAACCATCG,
SEQ ID NO 28: CGAUGGUUGUCCUAGUUUAAGCAUUAA, and
SEQ ID NO 29: UUAAUGCUUAAACUAGGACAACCAUCG.

The present invention also contemplates compositions for detecting Lyme disease-associated Borrelia comprising a nucleic acid hybrid formed between a Borrelia nucleic acid and an oligonucleotide having nucleic acid sequences substantially corresponding to:
SEQ ID NO 7: AGCCGCGGTAATACGTAAGGGTTTAGCGT, and
SEQ ID NO 44: AGCCGCGGUAAUACGUAAGGGUUUAGCGU
and which also has an oligonucleotide having a nucleic acid sequence substantially corresponding to at least one nucleic acid sequence that follows:
SEQ ID NO 8: CTTCCTCTATCAGACTCTAGACATATAGTTTCCAACATA,
SEQ ID NO 45: CUUCCUCUAUCAGACUCUAGACAUAUAGUUUCCAACAUA,
SEQ ID NO 9: CCACCCTTACACCAGAAATTCTAACTTCCTCTATCA, and
SEQ ID NO 46: CCACCCUUACACCAGAAAUUCUAACUUCCUCUAUCA,
and optionally contains one or more oligonucleotides having a sequence substantially corresponding to one of the following sequences:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 4: CGGGATTATTGGGCGTAAAGGGTGAGTA,
SEQ ID NO 6: ATAAAATACCACAGCTCAACTGTGGACCTATGTTGG,
SEQ ID NO 15: CGGGAUUAUUGGGCGUAAAGGGUGAGUA,
SEQ ID NO 17: AUAAAAUACCACAGCUCAACUGUGGACCUAUGUUGG,
SEQ ID NO 3: TACTCACCCTTTACGCCCAATAATCCCG,
SEQ ID NO 5: CCAACATAGGTCCACAGTTGAGCTGTGGTATTTTAT,
SEQ ID NO 14: UACUCACCCUUUACGCCCAAUAAUCCCG, and
SEQ ID NO 16: CCAACAUAGGUCCACAGUUGAGCUGUGGUAUUUUAU.

The present invention also contemplates compositions for detecting Lyme disease-associated Borrelia comprising a nucleic acid hybrid formed between a Borrelia nucleic acid and an oligonucleotide having a nucleic acid sequence substantially corresponding to
SEQ ID NO 18: CTGAAAAGTGTAGTCGATGGGAAACGGG, and
SEQ ID NO 48: CUGAAAAGUGUAGUCGAUGGGAAACGGG
and which also has an oligonucleotide having a nucleic acid sequence substantially corresponding to at least one nucleic acid sequence that follows:
SEQ ID NO 19: GCACTCATCATCACATCTTAGCTC,
SEQ ID NO 49: GCACUCAUCAUCACAUCUUAGCUC,
SEQ ID NO 20: CGTATTTTGCAGAGTTCCTTAACG, and
SEQ ID NO 50: CGUAUUUUGCAGAGUUCCUUAACG
and optionally contains one or more oligonucleotides having a sequence substantially corresponding to one of the following sequences:
SEQ ID NO 21: GGTGATGATCTTGATAGGAAAATCCG,
SEQ ID NO 25: GGUGAUGAUCUUGAUAGGAAAAUCCG,
SEQ ID NO 24: CGGATTTTCCTATCAAGATCATCACC,
SEQ ID NO 26: CGGAUUUUCCUAUCAAGAUCAUCACC,
SEQ ID NO 23: CGATGGTTGTCCTAGTTTAAGCATTAA,
SEQ ID NO 27: TTAATGCTTAAACTAGGACAACCATCG,
SEQ ID NO 28: CGAUGGUUGUCCUAGUUUAAGCAUUAA, and
SEQ ID NO 29: UUAAUGCUUAAACUAGGACAACCAUCG.

The present invention also contemplates compositions for detecting Borrelia hermsii having a nucleic acid hybrid formed between a Borrelia hermsii nucleic acid and an oligonucleotide having a nucleic acid sequence substantially corresponding to
SEQ ID NO 8: CTTCCTCTATCAGACTCTAGACATATAGTTTCCAACATA, and
SEQ ID NO 45: CUUCCUCUAUCAGACUCUAGACAUAUAGUUUCCAACAUA
and which also has an oligonucleotide having a nucleic acid sequence substantially corresponding to at least one nucleic acid sequence that follows:
SEQ ID NO 7: AGCCGCGGTAATACGTAAGGGTTTAGCGT,
SEQ ID NO 44: AGCCGCGGUAAUACGUAAGGGUUUAGCGU,
SEQ ID NO 11: AGCCGCGGTAATACGTAAGGGGCGAGCGT, and
SEQ ID NO 47: AGCCGCGGUAAUACGUAAGGGGCGAGCGU,
and optionally contains one or more oligonucleotides having a sequence substantially corresponding to one of the following sequences:
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 5: CCAACATAGGTCCACAGTTGAGCTGTGGTATTTTAT,
SEQ ID NO 6: ATAAAATACCACAGCTCAACTGTGGACCTATGTGG,
SEQ ID NO 16: CCAACAUAGGUCCACAGUUGAGCUGUGGUAUUUUAU, and
SEQ ID NO 17: AUAAAAUACCACAGCUCAACUGUGGACCUAUGUUGG.

The present invention also contemplates compositions for detecting Borrelia hermsii having a nucleic acid hybrid formed between a Borrelia hermsii nucleic acid and an oligonucleotide having a nucleic acid sequence substantially corresponding to
SEQ ID NO 18: CTGAAAAGTGTAGTCGATGGGAAACGGG, and
SEQ ID NO 48: CUGAAAAGUGUAGUCGAUGGGAAACGGG
and which also has an oligonucleotide having nucleic acid sequence substantially corresponding to at least one nucleic acid sequence that follows:
SEQ ID NO 19: GCACTCATCATCACATCTTAGCTC,
SEQ ID NO 49: GCACUCAUCAUCACAUCUUAGCUC,
SEQ ID NO 20: CGTATTTTGCAGAGTTCCTTAACG, and
SEQ ID NO 50: CGUAUUUUGCAGAGUUCCUUAACG
and optionally contains one or more oligonucleotides having a sequence substantially corresponding to one of the following sequences:

SEQ ID NO 22: GGTGTTGATTTTAGTAGGAAAATCCG,
SEQ ID NO 31: GGUGUUGAUUUUAGUAGGAAAAUCCG,
SEQ ID NO 30: CGGATTTTCCTACTAAAATCAACACC,
SEQ ID NO 32: CGGAUUUUCCUACUAAAAUCAACACC,
SEQ ID NO 23: CGATGGTTGTCCTAGTTTAAGCATTAA,
SEQ ID NO 27: TTAATGCTTAAACTAGGACAACCATCG,
SEQ ID NO 28: CGAUGGUUGUCCUAGUUUAAGCAUUAA, and
SEQ ID NO 29: UUAAUGCUUAAACUAGGACAACCAUCG.

In preferred embodiments, the present invention also contemplates nucleic acid hybrids comprising probes of the present invention and also having at least one helper oligonucleotide that has a nucleic acid sequence substantially corresponding to at least one of the nucleic acid sequences that follows:
SEQ ID NO 4: CGGGATTATTGGGCGTAAAGGGTGAGTA
SEQ ID NO 6: ATAAAATACCACAGCTCAACTGTGGACCTATGTTGG
SEQ ID NO 23: CGATGGTTGTCCTAGTTTAAGCATTAA The present invention also contemplates compositions for detecting Lyme disease-associated Borrelia comprising a nucleic acid hybrid formed between a Borrelia nucleic acid and an oligonucleotide having nucleic acid sequences substantially corresponding to
SEQ ID NO 8: CTTCCTCTATCAGACTCTAGACATATAGTTTCCAACATA, or
SEQ ID NO 45: CUUCCUCUAUCAGACUCUAGACAUAUAGUUUCCAACAUA
wherein the 19 3' most nucleotides are exactly as shown.

G. ASSAY METHODS

The present invention contemplates various methods for assaying for the presence of Borrelia nucleic acid within a sample. One skilled in the art will understand that the exact assay conditions, probes or primers used will vary depending on the particular assay format used and the source of the sample.

Generally, the present invention contemplates methods for detecting the presence of Borrelia microorganisms by contacting a test sample under stringent hybridization conditions with a nucleic acid hybridization assay probe capable of hybridizing under stringent hybridization assay conditions to a Borrelia target nucleic acid and not to nucleic acids from closely related microorganisms, said target nucleic acid having a nucleic acid sequence substantially corresponding to a sequence selected from the group consisting of:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC,
SEQ ID NO 35: GCAUAGACUUGCAUAUCCGCC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG,
SEQ ID NO 26: CGGAUUUUCCUAUCAAGAUCAUCACC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

Preferred methods for detecting the presence of Lyme disease-associated Borrelia include the step of contacting a test sample under stringent hybridization conditions with a nucleic acid hybridization assay probe capable of hybridizing under stringent hybridization assay conditions to a Lyme disease-associated Borrelia target nucleic acid sequence and not to nucleic acid sequences of closely related bacteria such as *Borrelia hermsii*, said target nucleic acid sequence substantially corresponding to a sequence selected from the group consisting of:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG, and
SEQ ID NO 26: CGGAUUUUCCUAUCAAGAUCAUCACC.

More preferred methods for detecting the presence of disease-associated Borrelia include the step of contacting a test sample under stringent hybridization conditions with a nucleic acid hybridization assay probe capable of hybridizing under stringent hybridization assay conditions to a Lyme disease-associated Borrelia target nucleic acid sequence and not to a nucleic acid sequence of closely related bacteria such as *Borrelia hermsii*, said target nucleic acid sequence substantially corresponding to a sequence selected from the group consisting of:
SEQ ID NO 1: GCATAGACTTATATATCCGCC,
SEQ ID NO 2: GGCGGATATATAAGTCTATGC,
SEQ ID NO 21: GGTGATGATCTTGATAGGAAAATCCG, and
SEQ ID NO 24: CGGATTTTCCTATCAAGATCATCACC.

The present invention also contemplates methods for detecting the presence of Borrelia microorganisms by contacting a test sample under stringent hybridization conditions with a nucleic acid hybridization assay probe capable of hybridizing under stringent hybridization assay conditions to a Borrelia 16S ribosomal nucleic acid sequence and not to nucleic acid sequences from closely related microorganisms, said target nucleic acid sequences substantially corresponding to a sequence selected form the group consisting of:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC, and
SEQ ID NO 35: GCAUAGACUUGCAUAUCCGCC.

Generally, the present invention contemplates methods for detecting the presence of Borrelia microorganisms by contacting a test sample under stringent hybridization conditions with a nucleic acid hybridization assay probe capable of hybridizing under stringent hybridization assay conditions to Borrelia 23S ribosomal nucleic acid and not to nucleic acid sequences from closely related microorganisms, said target nucleic acid sequence substantially corresponding to a sequence selected from the group consisting of:
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG,
SEQ ID NO 26: CGGAUUUUCCUAUCAAGAUCAUCACC,
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

The present invention contemplates methods for detecting the presence of *Borrelia hermsii* microorganisms by contacting a test sample under stringent hybridization conditions with a nucleic acid hybridization assay probe capable of hybridizing under stringent hybridization assay conditions to a Borrelia 16S ribosomal nucleic acid sequence and not to nucleic acid from closely related microorganisms, such as *Borrelia burgdorferi* and other Lyme disease-associated Borrelia, said target nucleic acid having a nucleotide sequence substantially corresponding to a sequence selected form the group consisting of:
SEQ ID NO 10: GGCGGATATGCAAGTCTATGC,
SEQ ID NO 33: GCATAGACTTGCATATCCGCC,
SEQ ID NO 34: GGCGGAUAUGCAAGUCUAUGC, and
SEQ ID NO 35: GCAUAGACUUGCAUAUCCGCC.

The present invention contemplates methods for detecting the presence of *Borrelia hermsii* microorganisms by contacting a test sample under stringent hybridization conditions with a nucleic acid hybridization assay probe capable of hybridizing under stringent hybridization assay conditions to a Borrelia 23S ribosomal nucleic acid sequence and not to nucleic acid sequences from closely related microorganisms, such as *Borrelia burgdorferi* and other Lyme disease-associated Borrelia, said target nucleic acid sequence substantially corresponding to a sequence selected from the group consisting of:
SEQ ID NO 22: GGTGTTGATTTTAGTAGGAAAATCCG,
SEQ ID NO 30: CGGATTTTCCTACTAAAATCAACACC,
SEQ ID NO 31: GGUGUUGAUUUUAGUAGGAAAAUCCG, and
SEQ ID NO 32: CGGAUUUUCCUACUAAAAUCAACACC.

The present invention contemplates methods for detecting the presence of Lyme disease-associated Borrelia microorganisms by contacting a test sample under stringent hybridization conditions with a nucleic acid hybridization assay probe capable of hybridization under stringent hybridization assay conditions to a Lyme disease-associated Borrelia 16S ribosomal nucleic acid sequence and not to nucleic acid sequences from closely related microorganisms, said target nucleic acid sequence substantially corresponding to a sequence selected from the group consisting of:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC, and
SEQ ID NO 13: GGCGGAUAUAUAAGUCUAUGC.

Most preferred are methods for detecting the presence of Lyme disease-associated Borrelia microorganisms by contacting a test sample under stringent hybridization conditions with a nucleic acid hybridization assay probe capable of hybridization under stringent hybridization assay conditions to a Lyme disease-associated Borrelia 16S ribosomal nucleic acid sequence and not to nucleic acid sequences from closely related microorganisms, said target nucleic acid sequence substantially corresponding to a sequence selected from the group consisting of:
SEQ ID NO 1: GCATAGACTTATATATCCGCC
SEQ ID NO 2: GGCGGATATATAAGTCTATGC The present invention contemplates methods for detecting the presence of Lyme disease-associated Borrelia microorganisms by contacting a test sample under stringent hybridization conditions with a nucleic acid hybridization assay probe capable of hybridizing under stringent hybridization assay conditions to a Lyme disease-associated Borrelia 23S ribosomal nucleic acid sequence and not to nucleic acid sequences from closely related microorganisms, said target nucleic acid sequence substantially corresponding to a sequence selected from the group consisting of:
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG, and
SEQ ID NO 26: CGGAUUUUCCUAUCAAGAUCAUCACC.

Most preferred are methods for detecting the presence of Lyme disease-associated Borrelia microorganisms by contacting a test sample under stringent hybridization conditions with a nucleic acid hybridization assay probe capable of hybridizing under stringent hybridization assay conditions to a Lyme disease-associated Borrelia 23S ribosomal nucleic acid sequence and not to nucleic acid sequences from closely related microorganisms, said target nucleic acid sequence substantially corresponds to the nucleotide sequence:
SEQ ID NO 21: GGTGATGATCTTGATAGGAAAATCCG.

The present invention also contemplates methods of detecting Borrelia microorganisms by first amplifying a portion of the Borrelia nucleic acid and then optionally using a hybridization assay probe of the present invention to assay for a specific Borrelia nucleic acid amplified by the primers of the present invention. The amplified nucleic acid can be detected by a number of methods including gel electrophoresis.

In preferred embodiments, the present invention contemplates methods of detecting Borrelia nucleic acid by first amplifying said nucleic acid with at least one amplification oligonucleotide that will bind to or cause elongation through one or more of the following sequences:
SEQ ID NO 7: AGCCGCGGTAATACGTAAGGGTTTAGCGT,
SEQ ID NO 8: CTTCCTCTATCAGACTCTAGACATATAGTTTCCAACATA,
SEQ ID NO 9: CCACCCTTACACCAGAAATTCTAACTTCCTCTATCA,
SEQ ID NO 11: AGCCGCGGTAATACGTAAGGGGCGAGCGT,
SEQ ID NO 18: CTGAAAAGTGTAGTCGATGGGAAACGGG,
SEQ ID NO 19: GCACTCATCATCACATCTTAGCTC,
SEQ ID NO 20: CGTATTTTGCAGAGTTCCTTAACG,
wherein said amplification oligonucleotide optionally has a nucleic acid sequence recognized by an RNA polymerase or which enhances initiation of elongation by an RNA polymerase.

This first method step is then optionally followed by detecting the amplified nucleic acid produced in the amplification step with an oligonucleotide hybridization assay probe able to specifically hybridize to Borrelia nucleic acids under stringent hybridization conditions.

The amplification oligonucleotide used in the methods of the present invention may optionally have a nucleic acid sequence recognized by an RNA polymerase or which enhances initiation or elongation by an RNA polymerase.

H. DIAGNOSTIC SYSTEMS

The present invention also contemplates diagnostic systems in kit form. A diagnostic system of the present invention may include a kit which contains, in an amount sufficient for at least one assay, amplification primers and/or hybridization assay probes of the present invention in a packaging material. Typically, the kits would also include instructions for use of the packaged primers and/or probes.

The various components of the diagnostic system may be provided in various forms. For example, the required enzymes, the nucleotide triphosphates, the primers and probes may be provided as a lyophilized reagent. These lyophilized reagents may be premixed before lyophilization so that when reconstituted form a complete mixture with the proper ratio of each of the components ready for use in the assay. In addition, the diagnostic systems of the present invention may contain a reconstitution reagent for reconstituting the lyophilized reagents of the kit. In preferred kits, the enzymes, nucleotides, triphosphates and required cofactors for the enzymes are provided as a single lyophilized reagent that when reconstituted forms a proper reagent for use in the present methods. In these preferred kits, a lyophilized primer agent may also be provided. In other preferred kits, lyophilized probe reagents are provided.

Typical packaging materials would include solid matrices such as glass, plastic, paper, foil and the like, capable of holding within fixed limits hybridization assay probe or amplification primer of the present invention. Thus, for example, a package made from packaging materials can be a glass vial used to contain microgram to milligram quantities of a contemplated primer or hybridization assay probe or it could be a microtiter plate well to which the probes and/or primers of the present invention have been operatively affixed, i.e., linked so as to be capable of participating in a detection method of the present invention.

Instructions for use typically include a tangible expression describing the various reagents and/or concentrations of reagents and at least one assay method parameter which, for example, would be the relative amounts of reagents to use per amount of sample. In addition, such specifics as maintenance, time periods, temperature and buffer conditions may also be included.

The present invention contemplates diagnostic systems or kits containing the oligonucleotides of a composition of the present invention. The present invention also contemplates diagnostic systems or kits containing the oligonucleotides required to perform a method of the present invention.

The present invention contemplates diagnostic systems or kits containing at least one oligonucleotide having a nucleic acid sequence substantially corresponding to a nucleic acid sequence selected from the group consisting of:
SEQ ID NO 1: GCATAGACTTATATATCCGCC,
SEQ ID NO 2: GGCGGATATATAAGTCTATGC,
SEQ ID NO 12: GCAUAGACUUAUAUAUCCGCC,
SEQ ID NO 13: GGCGGAUAUAUAAGUCUAUGC,
SEQ ID NO 21: GGTGATGATCTTGATAGGAAAATCCG,
SEQ ID NO 24: CGGATTTTCCTATCAAGATCATCACC,
SEQ ID NO 25: GGUGAUGAUCUUGAUAGGAAAAUCCG, and
SEQ ID NO 26: CGGAUUUUCCUAUCAAGAUCAUCACC.

The present invention contemplates diagnostic systems or kits optionally having at least one helper probe having a nucleic acid sequence substantially corresponding to the sequence selected from the group consisting of:
SEQ ID NO 3: TACTCACCCTTTACGCCCAATAATCCCG,
SEQ ID NO 5: CCAACATAGGTCCACAGTTGAGCTGTGGTATTTAT,
SEQ ID NO 14: UACUCACCCUUUACGCCCAAUAAUCCCG,
SEQ ID NO 16: CCAACAUAGGUCCACAGUUGAGCUGUGGUAUUUAU,
when said oligonucleotide is:
SEQ ID NO 1: GCATAGACTTATATATCCGCC, or
SEQ ID NO 12: GCAUAGACUUAUAUAUCCGCC;
or
SEQ ID NO 4: CGGGATTATTGGGCGTAAAGGGTGAGTA,
SEQ ID NO 6: ATAAAATACCACAGCTCAACTGTGGACCTATGTGG,
SEQ ID NO 15: CGGGAUUAUUGGGCGUAAAGGGUGAGUA,
SEQ ID NO 17: AUAAAAUACCACAGCUCAACUGUGGACCUAUGUUGG;
when said oligonucleotide is:
SEQ ID NO 2: GGCGGATATATAAGTCTATGC, or
SEQ ID NO 13: GGCGGAUAUAUAAGUCUAUGC;
or
SEQ ID NO 23: CGATGGTTGTCCTAGTTTAAGCATTAA,
SEQ ID NO 28: CGAUGGUUGUCCUAGUUUAAGCAUUAA,
when said oligonucleotide is:
SEQ ID NO 21: GGTGATGATCTTGATAGGAAAATCCG.

The present invention contemplates diagnostic systems or kits containing at least one oligonucleotide having a nucleic acid sequence substantially corresponding to a nucleic acid sequence selected from the group consisting of:
SEQ ID NO. 7: AGCCGCGGTAATACGTAAGGGTTTAGCGT,
SEQ ID NO. 8: CTTCCTCTATCAGACTCTAGACATATAGTTTCCAACATA,
SEQ ID NO. 9: CCACCCTTACACCAGAAATTCTAACTTCCTCTATCA,
SEQ ID NO. 11: AGCCGCGGTAATACGTAAGGGGCGAGCGT,
SEQ ID NO. 18: CTGAAAAGTGTAGTCGATGGGAAACGGG,
SEQ ID NO. 19: GCACTCATCATCACATCTTAGCTC, and
SEQ ID NO. 20: CGTATTTTGCAGAGTTCCTTAACG.
optionally having a 5' sequence recognized by an RNA polymerase or which enhances initiation or elongation by an RNA polymerase.

The present invention contemplates diagnostic systems or kits optionally having at least one oligonucleotide having a nucleic acid sequence substantially corresponding to a nucleic acid sequence selected from the group consisting of:
SEQ ID NO. 1: GCATAGACTTATATATCCGCC, and
SEQ ID NO. 2: GGCGGATATATAAGTCTATGC,
when said two oligonucleotides are selected from the group of:
SEQ ID NO. 7: AGCCGCGGTAATACGTAAGGGTTTAGCGT,
SEQ ID NO. 8: CTTCCTCTATCAGACTCTAGACATATAGTTTCCAACATA, SEQ ID NO. 9: CCACCCTTACACCAGAAATTCTAACTTCCTCTATCA, and

SEQ ID NO. 11: AGCCGCGGTAATACGTAAGGGGCGAGCGT;

or

SEQ ID NO. 10: GGCGGATATGCAAGTCTATGC,

SEQ ID NO. 21: GGTGATGATCTTGATAGGAAAATCCG, and

SEQ ID NO. 22: GGTGTTGATTTTAGTAGGAAAATCCG, when said oligonucleotides are selected from the group of:

SEQ ID NO. 18: CTGAAAAGTGTAGTCGATGGGAAACGGG,

SEQ ID NO. 19: GCACTCATCATCACATCTTAGCTC, and

SEQ ID NO. 20: CGTATTTTGCAGAGTTCCTTAACG.

The present invention contemplates diagnostic systems or kits containing oligonucleotides having a nucleic acid sequence substantially corresponding to the following sequences:

SEQ ID NO. 7: AGCCGCGGTAATACGTAAGGGTTTAGCGT,

SEQ ID NO. 8: CTTCCTCTATCAGACTCTAGACATATAGTTTCCAACATA, and

SEQ ID NO. 1: GCATAGACTTATATATCCGCC or

SEQ ID NO. 2: GGCGGATATATAAGTCTATGC.

The present invention contemplates diagnostic systems or kits containing oligonucleotides having a nucleic acid sequence substantially corresponding to the following sequences:

SEQ ID NO. 7: AGCCGCGGTAATACGTAAGGGTTTAGCGT,

SEQ ID NO. 9: CCACCCTTACACCAGAAATTCTAACTTCCTCTATCA, and

SEQ ID NO. 1: GCATAGACTTATATATCCGCC or

SEQ ID NO. 2: GGCGGATATATAAGTCTATGC.

The present invention contemplates diagnostic systems or kits containing oligonucleotides having a nucleic acid sequence substantially corresponding to the following sequences:

SEQ ID NO 11: AGCCGCGGTAATACGTAAGGGGCGAGCGT,

SEQ ID NO 8: CTTCCTCTATCAGACTCTAGACATATAGTTTCCAACATA, and

SEQ ID NO 10: GGCGGATATGCAAGTCTATGC or

SEQ ID NO 33: GCATAGACTTGCATATCCGCC.

The present invention contemplates diagnostic systems or kits containing oligonucleotides having a nucleic acid sequence substantially corresponding to the following sequences:

SEQ ID NO 18: CTGAAAAGTGTAGTCGATGGGAAACGGG,

SEQ ID NO 19: GCACTCATCATCACATCTTAGCTC,

SEQ ID NO 21: GGTGATGATCTTGATAGGAAAATCCG, or

SEQ ID NO 24: CGGATTTTCCTATCAAGATCATCACC.

The present invention contemplates diagnostic systems or kits containing oligonucleotides having a nucleic acid sequence substantially corresponding to the following sequences;

SEQ ID NO 18: CTGAAAAGTGTAGTCGATGGGAAACGGG,

SEQ ID NO 20: CGTATTTTGCAGAGTTCCTTAACG,

SEQ ID NO 21: GGTGATGATCTTGATAGGAAAATCCG, or

SEQ ID NO 24: CGGATTTTCCTATCAAGATCATCACC.

EXAMPLES

Examples are provided below to illustrate different aspects and embodiments of the present invention. These examples are not intended in any way to limit the disclosed invention.

Probes specific for Lyme disease-associated Borrelia including *Borrelia burgdorferi* were identified from published and determined 16S and 23S rRNA sequences. The nucleic acid sequence from phylogenetically near neighbors *B. hermsii, B. turicatae, B. anserina* and *B. coriaceae* were used as comparisons with the nucleic acid sequence of *B. burgdorferi* to identify variable regions.

The following hybridization assay probe sequences are featured in the examples described below: SEQ ID NO. 1, SEQ ID NO. 2 and SEQ ID NO. 21, directed to *B. burgdorferi* sequences, and SEQ ID NOS. 10 and 22, directed to *B. hermsii* sequences.

The probes were synthesized with a non-nucleotide linker as described by Arnold et al., supra, "Non-Nucleotide Linking Reagents For Nucleotide Probes", then labeled with a chemiluminescent acridinium ester as described by Arnold et al., supra, U.S. Pat. No. 5,185,439. The reactivity and specificity of the probes for Lyme disease-associated Borrelia were demonstrated using a homogeneous assay format as described by Arnold et al., supra, "Homogenous Protection Assay" and Arnold et al., *Clin. Chem.* 35:1588 (1989) (hereby incorporated by reference herein). Results are given in relative light units (RLU), a measure of photons detected by the luminometer. Probes were hybridized to the nucleic acid of a cell lysate or products of target amplification reactions. The following examples describe hybridization assay probes and amplification oligonucleotides targeted to Lyme disease-associated Borrelia, including *Borrelia burgdorferi*, and their use in hybridization and amplification/hybridization assays.

Example 1

Detection of Lyme Disease-Associated Borrelia Using a Probe Targeted to 16S rRNA This example illustrates the ability of a probe targeted to Lyme disease-associated Borrelia 16S rRNA to directly detect the Lyme disease-associated Borrelia nucleic acid from *B. burgdorferi*, but not *B. hermsii* nucleic acid. The probe solution contained an acridinium ester labeled probe synthesized with the sequence SEQ ID NO. 1 and corresponding unlabeled helper oligonucleotides having sequences SEQ ID NO. 3 and SEQ. ID. NO. 5. The target sequence for the probe consisting of SEQ ID NO. 1 was selected to be identical in strains representing the Lyme disease-associated Borrelia groups, thus this probe is expected to detect all three of the subspecies or species associated with Lyme disease (VS461, *B. burgdorferi* sensu strictu and *B. garinii*).

Alignment of a region of *B. burgdorferi*, *B. hermsii* and *E. coli* 16S sequences are shown below where dots indicate similarities in the sequence:
*E. coli* 16S

```
5'-GGCGGUUUGUUAAGUCUG-AU-   (SEQ ID no:64)
3'

..... . ........
Bbu  GGCGGAUAUAUAAGUCUUACG- (SEQ ID no:65)
3'

Bhe  .........GC...... .... (SEQ IF no:66)
```

In the following experiment, nucleic acid released from lysed cells was assayed directly. An example of a method for preparing a lysate is provided by Murphy et al., EPO Publication Number 288618, hereby incorporated by reference herein. Fifty μl of each cell lysate and 50 probe solution containing 100 mM lithium succinate pH 5, 2% (w/v) lithium lauryl sulfate, 1.2 M lithium chloride, 20 mM ethylene-diaminetetraacetic acid (EDTA), and 20 mM ethylene glycol bis (beta-amino ethyl ether) N,N,N',N' tetraacetic acid (EGTA), were mixed and incubated at 60° C. for 20 minutes, followed by addition of 0.3 ml of 0.15 M sodium tetraborate pH 8.5, 1% Triton X-100, and incubation at 60° C. for 15 minutes. The reactions were cooled and the chemiluminescence remaining, from the hybridized acridinium ester labeled probe, was measured in a luminometer after automatic injection of 0.1% hydrogen peroxide in 1 mM nitric acid, followed by injection of a 1 N sodium hydroxide solution. Results were given in relative light units or RLU. An all-bacteria/yeast probe mixture with helper oligonucleotides containing SEQ ID NOS. 58–63 was used as a control to demonstrate the presence of bacterial nucleic acid. Hogan et al., supra, entitled "Nucleic Acid Probes for Detection and/or Quantitation of Non-Viral organisms", gives examples of suitable all-bacteria/yeast probe mixtures. The data show that the probe hybridizes to Lyme disease associated Borrelia species *Borrelia burgdorferi* and distinguishes it from its close phylogenetic relative, *Borrelia hermsii*.

TABLE 1

HYBRIDIZATION OF PROBE SEQ ID NO. 1 TO rRNA OF
*BORRELIA BURGDORFERI* AND *BORRELIA HERMSII*.

| Probe: | RLU | |
|---|---|---|
| | SEQ ID NO. 1 | All bacterial |
| Organism: | | |
| *B. burgdorferi* | 811,712 | 1,187,345 |
| | 795,818 | 1,183,434 |
| *B. hermsii* | 1,033 | 2,067,782 |
| | 959 | 2,085,881 |
| No target | 907 | 2,074 |
| | 902 | 2,071 |

Example 2

Detection of Borrelia Organisms Using Amplification Followed by Hybridization With an Oligonucleotide Probe Detection of small numbers of Borrelia organisms can be enhanced by amplification of the rRNA or rDNA prior to assay by hybridization. In this experiment, purified *B. burgdorferi* DNA from approximately 30,000 organisms was amplified with a oligonucleotides complementary or homologous to *B. burgdorferi* rRNA sequences. One amplification oligonucleotide consisted of a promoter-primer synthesized with sequence SEQ. ID. NO. 7 at the 3' end and a T7 promoter sequence SEQ ID NO. 43 at the 5' end (herein-after promoter-primers will be identified by the SEQ ID No. of its target binding region), and the second oligonucleotide consisted of a primer of sequence SEQ. ID. NO. 8 or 9. The amplification mixture contained 50 mM Tris HCl, pH 8.5, 40 mM potassium acetate, 6 mM GTP, 6 mM ATP, 2.5 mM UTP, 2.5 mM CTP, 0.2 mM dATP, 0.2 mM dTTP, 0.2 mM dCTP, 0.2 mM dGTP, 17.5 mM MgCl$_2$, 10 mM dithiothreitol, 10% (v/v) glycerol, 2 mM spermidine, 30 pmol of promoter-primer SEQ. ID. NO. 7 and 30 pmol of primer SEQ. ID. NO. 8 or 9 in a final volume of 100 μl. The mixture was heated to 95° C. for 8 minutes, cooled to 42° C. and 900 units of MMLV reverse transcriptase (RT) and 400 units of T7 RNA polymerase were added. After a two hour incubation at 42° C., twenty μl of the amplification reaction was assayed by hybridization with acridinium ester labeled probe of sequence SEQ. ID. NO. 1 with unlabeled helpers SEQ. ID. NO. 3 and 5. The results of duplicate reactions are reported.

TABLE 2

Amplification of *Borrelia burgdorferi* rDNA
and Selection With Probe SEQ ID NO. 1.

| Primer SEQ ID NOs. | 7/8 | 7/9 |
|---|---|---|
| RLU | 128,140 | 888,579 |
| | 72,397 | 388,515 |

These data show that a probe, of SEQ ID No. 1, complementary to Borrelia RNA may be used to detect rRNA sequences directly or to detect the products of amplification reactions. These results demonstrate that primer sets having SEQ ID NOS 7 (plus SEQ ID NO 43 at the 5' end) and either of SEQ ID NOS. 8 or 9 are capable of amplifying *B. burgdorferi* nucleic acid. It also appears that SEQ ID NO. 9 is the more effective negative sense primer.

Example 3

Amplification of Borrelia Nucleic Acid Using Primers Hybridizing to 16S rRNA Sequences In this example, nucleic acid from Borrelia was amplified with primers complementary or homologous to 16S ribosomal RNA sequences. Lysate from *B. burgdorferi* or *B. hermsii* cells was quantitated by hybridization with a probe directed to a conserved region of the RNA. The RNA was diluted and added to a reaction mixture containing 30 pmol of promoter-primer of SEQ. ID. NO. 8 with the sequence SEQ ID NO. 43 at the 5' end and 30 pmol of primer SEQ ID NO. 7. Final reaction conditions were 100 mM Tris HCl, pH 8.5, 35 mM potassium chloride, 4 mM GTP, 4 mM ATP, 4 mM UTP, 4 mM CTP, 0.2 mM dATP, 0.2 mM dTTP, 0.2 mM dCTP, 0.2 mM dGTP, 20 mM MgCl$_2$, 10 mM dithiothreitol, 10% glycerol, 2 mM spermidine. The mixture was heated to 95° C. for 5 min, cooled to 42° C., and 800 U MMLV RT and 400 U T7 RNA polymerase were added. Following a two hour incubation at 42° C., ten μl of the reaction was assayed by hybridization as described in Example 1 in the presence of 15 mM aldrithiol using a probe synthesized with the sequence, SEQ ID NO. 2, and unlabeled helper probes of sequence SEQ ID NO. 4 and 6. The results show that the primers successfully amplified *Borrelia burgdorferi* nucleic acid, and allowed detection of small amounts of Borrelia rRNA. No significant cross reaction was seen even in the presence of a vast excess of *B. hermsii* nucleic acids. The results of triplicate reactions are reported.

TABLE 3

Amplification of *Borrelia burgdorferi* and *Borrelia hermsii* Nucleic Acid With Primers With SEQ ID NOS. 7/8 and Detection With Probe SEQ ID NO. 2.

|  | B. burgdorferi rRNA ($2 \times 10^{-21}$ moles) | B. hermsii rRNA ($3 \times 10^{-9}$ moles) | (0 moles) |
|---|---|---|---|
| RLU | 194,434 | 548 | 514 |
|  | 217,828 | 626 | 610 |
|  | 319,662 | 646 |  |

Example 4

Amplification and Detection of Borrelia Using Hybridization Assay Probes Nos. 2 and 10

In this example, amplification was performed as in Example 3 except a promoter-primer of SEQ ID NO. 8 (with a 5' promoter sequence of SEQ ID NO. 43) and primer of sequence SEQ ID NO. 11 were used and a probe of SEQ ID NO 10 was used. The acridinium ester labeled probes and unlabeled helper probes used in this example are shown in the table. These results show that these primers are able to amplify both *B. burgdorferi* and *B. hermsii* rRNA sequences and that the probes distinguish between the two organisms in the disclosed assay system.

TABLE 4

AMPLIFICATION OF *BORRELIA BURGDORFERI* AND *BORRELIA HERMSII* NUCLEIC ACID AND DETECTION WITH PROBE SEQ ID NO. 2 AND 10

| Probe<br>Helpers | SEQ ID NO. 2 (RLU)<br>SEQ ID NOs 4 and 6 | SEQ ID NO. 10 (RLU)<br>SEQ ID NO. 6 |
|---|---|---|
| $2 \times 10^{-20}$ moles | 899,521 | 1,963 |
| B. burgdorferi | 912,706 | 1,800 |
| rRNA | 919,681 | 1,809 |
| $3 \times 10^{-18}$ moles | 2,783 | 1,335,183 |
| B. hermsii rRNA | 2,322 | 1,328,290 |
|  | 2,125 | 1,368,581 |
| 0 moles rRNA | 1,619 | 1,137 |
|  | 1,596 | 1,347 |
|  | 1,373 | 1,174 |

Example 5

Detection of Borrelia Using a Probe Directed to the 23S Ribosomal RNA

The 23S rRNA sequence of *B. burgdorferi* has been published, *J. Clin. Microbiol* 30:3082 (1992) and *J. Bacteriol.* 174: 3766–3774 (1992). To design specific primers and probes directed to Borrelia 23S rRNA sequences, the sequences of closely related organisms were required. *Borrelia hermsii, Borrelia coriaceae*, and *Borrelia turicatae* were grown in BSK H broth (Sigma) for several days, pelleted and resuspended in 50 mM Tris HCl pH 8.0. DNA was prepared following lysis in phenol equilibrated with Tris HCl [pH 8.0]. The final product was isolated by ethanol precipitation. 5' and 3' portions of 23S rDNA sequence were amplified with primers directed to conserved regions of Borrelia species or to *B. burgdorferi* specific sequence using the polymerase chain reaction and AmpliTaq polymerase (Perkin-Elmer). Purified amplicons were sequenced using commercially available kits from Promega (fmol kit) or New England Biolabs, (Circumvent kit), using $^{35}$S-dNTP incorporation. The sequence obtained was compared with the published *Borrelia burgdorferi* sequence (Gen-Bank accession numbers M88330, *J. Clin. Microbiol.* 3:3082 (1992) and M93664 *J. Bacteriol.*, 174: 3766–74 (1992).

A specific sequence in which *B. burgdorferi* varied from *B. hermsii* and *B. turicatae* was chosen for 23S probe design. This region corresponds to bases 1478–1500 of *E. coli, B. hermsii* and *B. turicatae* had identical nucleotide sequences in this region, which varied from *B. burgdorferi* RNA by four bases. A probe was designed to *B. burgdorferi* (SEQ ID NO. 21) and a second probe was designed to *B. hermsii/B. turicatae* (SEQ ID NO. 22). The rRNA sequences are shown below:

```
E.coli
     GGC---UGGUUUUCCAGGCAAAUCCG    (SEQ ID no:67)

..         ..    ...  ........
Bbu  GGUGAUGAUCUUGAUAGGAAAAUCCG    (SEQ ID No. 25)

....  ....  ..  ............
Bhe  GGUGUUGAUUUUAGUAGGAAAAUCCG    (SEQ ID No. 31)
```

To demonstrate amplification efficiency and probe specificity, the following experiment was performed. Lysates were prepared from cultures of *B. burgdorferi*, strain N40, and *B. turicatae* by resuspending the cells from 7 ml of culture in 0.75 ml of a solution containing 10 mM N-acetyl-L-cysteine, 2 mM EDTA, 40 mM Tris HCl pH 8 and heating to 60° C. for five min. To quantitate the amount of nucleic acid in each sample, hybridizations were performed with different amounts of the sample and a probe directed to a conserved region of Borrelia 23S rRNA as described in Example 1. The values obtained were compared to results with a known standard.

Known amounts of nucleic acid in either a *B. burgdorferi* or a *B. turicatae* lysate were amplified in a 100 µl reaction containing 30 pmol of a promoter-primer synthesized with a 5' promoter sequence (SEQ ID NO. 43) and a 3' target hybridizing region of either SEQ ID NO. 19 or SEQ ID NO. 20, and a primer having SEQ ID NO. 18. The lysates were diluted in water to the appropriate concentration and added to a solution containing the primer and promoter-primer, heated to 95° C. for 15 minutes, cooled to 42° C. for 5 minutes. Moloney Murine Leukemia Virus reverse transcriptase (MMLV RT), 900 units, and 400 units of T7 RNA polymerase were added. The final amplification mixture contained 50 mM Tris HCl, pH 8.5, 35 mM potassium chloride, 4 mM GTP, 4 mM ATP, 4 mM UTP, 4 mM CTP, 1 mM dATP, 1 mM dTTP, 1 mM dCTP, 1 mM dGTP, 20 mM MgCl$_2$, 20 mM N-acetyl-L-cysteine, and 5% glycerol. After a two hour incubation at 42° C., the entire one hundred Ml amplification reaction was assayed by hybridization with an acridinium ester labeled probe of SEQ ID NO. 21.

Hybridization was performed in 200 µl of a solution containing 0.05 M lithium succinate pH 5, 0.6 M LiCl, 1% (w/v) lithium lauryl sulfate, 10 mM EDTA, 10 mM EGTA, at 60° C. for 10 minutes, followed by addition of 300 µl of 0.15 M sodium tetraborate pH 8.5, 1% TRITON® X-100. This mixture was incubated at 60° C. for 10 minutes, and cooled to room temperature. The remaining chemiluminescence in each tube was assayed in a Gen-Probe LEADER® I luminometer equipped with automatic injection of 1 mM nitric acid and 0.1% hydrogen peroxide followed by injection of a solution containing 1 N sodium hydroxide. Results are given in RLU.

TABLE 5

Amplification of *Borrelia burgdorferi* nucleic acid with amplification oligonucleotides comprising SEQ ID NO. 19 and 18 or 20 and 18, followed by detection with a probe comprising SEQ ID NO. 21.

| Target | Primers SEQ ID NOs. 18/19 | Primers SEQ ID NOs. 18/20 |
| --- | --- | --- |
| $3 \times 10^{-20}$ moles *B. burgdorferi* rRNA | 33,366 | 211,867 |
| $6 \times 10^{-21}$ moles *B. burgdorferi* rRNA | 15,115 | 57,029 |
| $3 \times 10^{-20}$ moles *B. turicatae* rRNA | 3,676 | 2,260 |
| $3 \times 10^{-21}$ moles *B. turicatae* rRNA | 2,215 | 2,297 |
| 0 moles rRNA | 2,408 | 2,324 |

In other experiments an oligonucleotide having a sequence, SEQ ID NO. 19 was used as a primer. Primers with SEQ ID NOS. 18 and 19 and SEQ ID NOS. 23 and 19 were shown to amplify rRNA sequences of both *B. burgdorferi* strains B31 and BN40 (data not shown).

Example 6

Specific Detection of *Borrelia hermsii* Using a Hybridization Assay Probe Directed to 23S rRNA In this example, specificity of a probe to *B. hermsii* was demonstrated. *B. burgdorferi*, *B. hermsii* and *B. turicatae* are very closely related at the 23S rRNA nucleic acid sequence level. A probe was designed to detect both *B. hermsii* and *B. turicatae* in the same region of 23S rRNA as the *B. burgdorferi* 23S rRNA probe. Two synthetic targets containing either *B. burgdorferi* or *B. hermsii*/*B. turicatae* sequence were synthesized and each target hybridized with probe of SEQ ID NO. 22 under the conditions described except that the hybridization was performed at 55° C. for 15 minutes. After three hundred μl of a solution containing 0.15 M sodium tetraborate pH 8.5, 1% TRITON® X-100 was added, the reactions were incubated for 5 minutes at 55° C. The samples were read in a luminometer as described above. The results show that the probe can distinguish *B. hermsii* sequences from *B. burgdorferi* sequences.

TABLE 6

Hybridization of *B. hermsii*/*B. turicatae* probe with *B. hermsii* and *B. burgdorferi* synthetic DNA targets.

| Target sequence | Amount of Synthetic DNA target | RLU with Probe SEQ ID No. 22 |
| --- | --- | --- |
| *B. hermsii* | $10^{-11}$ moles | 890,609 |
| *B. hermsii* | $10^{-12}$ moles | 852,419 |
| *B. hermsii* | $10^{-13}$ moles | 885,979 |
| *B. hermsii* | $10^{-14}$ moles | 511,419 |
| *B. burgdorferi* | $10^{-11}$ moles | 2,684 |
| *B. burgdorferi* | $10^{-12}$ moles | 1,911 |
| *B. burgdorferi* | $10^{-13}$ moles | 808 |

Example 7

Amplification and Detection of Borrelia Using a 23S rRNA Hybridization Assay Probe Next, amplification and detection of *B. turicatae* nucleic acid was demonstrated. *B. turicatae* cell lysate was amplified with 30 pmole of a primer synthesized with sequence SEQ ID NO. 18 and 30 pmol of a promoter-primer with a 5' sequence SEQ ID NO. 43 and a 3' target hybridizing region SEQ ID NO. 19. The entire amplification reaction was hybridized with a probe of SEQ ID NO. 22 in the presence of 2.5 pmol of an unlabeled helper probe SEQ ID NO. 23 at 55° C. for 15 minutes, and then incubated at 55° C. for 5 minutes following addition of 0.15 M sodium tetraborate pH 8.5, 1% TRITON®X-100 and read in a luminometer. Identical signals are anticipated with *B. hermsii*, because the sequences of the two organisms are identical in this region of the 23S rRNA.

TABLE 7

Amplification of *B. turicatae* rRNA sequences.

| Target | Amount of rRNA target | RLU with Probe SEQ ID No. 22 |
| --- | --- | --- |
| *B. turicatae* | $1.2 \times 10^{-19}$ moles | 240,607 |
| *B. turicatae* | $6 \times 10^{-20}$ moles | 133,812 |
| *B. turicatae* | $3 \times 10^{-20}$ moles | 20,345 |
| *B. turicatae* | $6 \times 10^{-21}$ moles | 14,968 |
| No target added | 0 moles | 751 |

Example 8

Specific Amplification and Specific Detection of Borrelia in the Presence of Microorganisms Found in Blood The primer SEQ ID NO. 18 and promoter-primer with SEQ ID NO. 20 at the 3' end were used to amplify cell lysates prepared from a panel of organisms which might be expected to be found in blood isolates. At least $3 \times 10^{-19}$ moles of rRNA from each cell lysate was tested with a probe synthesized with nucleotide sequence SEQ ID No. 21 (Table 8) or SEQ ID NO. 22 (data not shown). No cross reaction was observed to non-Borrelia species with either probe. The probe of sequence SEQ ID NO. 22 gave a strong signal (>2,000,000 RLU) with the *B. turicatae* culture confirming the presence of *B. turicatae* cells. The results of detection with SEQ ID NO 21 are shown in the following table.

TABLE 8

Amplification of sequences of microorganisms isolated in blood specimens.

| Organism | Probe: ATCC NO. | RLU SEQ ID NO. 21 |
| --- | --- | --- |
| *Bacteroides fragilis* | 23745 | 3,406 |
| | | 3,525 |
| *B. burgdorferi* | | 1,529,040 |
| | | 1,335,897 |
| *B. turicatae* | 35209 | 3,573 |
| | | 3,524 |
| *B. coriaceae* | 43381 | 3,457 |
| | | 4,100 |
| *Escherichia coli* | 25922 | 5,091 |
| | | 4,504 |

TABLE 8-continued

Amplification of sequences of microorganisms isolated in blood specimens.

| Organism | Probe: ATCC NO. | RLU SEQ ID NO. 21 |
|---|---|---|
| Haemophilus influenzae | 19418 | 4,737 |
| | | 3,531 |
| Klebsiella pneumoniae | 23357 | 4,510 |
| | | 3,853 |
| Proteus mirabilis | 25933 | 3,893 |
| | | 4,170 |
| Pseudomonas aeruginosa | 25330 | 4,281 |
| | | 4,335 |
| Staphylococcus aureus | 25923 | 3,088 |
| | | 3,646 |
| Staphylococcus epidermidis | 12228 | 4,722 |
| | | 3,141 |
| Streptococcus mitis | 9811 | 3,059 |
| | | 3,171 |
| Streptococcus pneumoniae | 6306 | 3,081 |
| | | 3,038 |

The above data confirm that the novel amplification oligonucleotides and probes herein disclosed and claimed are capable of amplifying Borrelia rRNA sequences and are capable of distinguishing the Lyme disease associated Borrelia, *Borrelia burgdorferi*, from other bacteria and members of the Borrelia genus.

Example 9

Amplification and Specific Detection of Borrelia Using a 16S Ribosomal Probe

The hybridization assay probe Sequence I.D. No. 1, specific for 16S ribosomal nucleic acid was used to detect the presence of Borrelia and to determine that this hybridization assay probe does not cross-react with other organisms commonly found in blood. The hybridization probe was hybridized to Borrelia nucleic acid in cell lysates in the presence of helper oligonucleotides Sequence ID Nos. 3 and 5. The assay was performed using a direct hybridization format as described above in Example 1. The presence of ribosomal RNA was verified in each sample by hybridizing the sample with the all-bacterial probe and helper oligonucleotides SEQ ID NOS. 58, 59, 60 and 61, or a fungal probe and helper probes SEQ ID NOS. 62 and 63. In this assay a value of greater than 30,000 relative light units (RLU) is considered positive. The results from this assay are shown below in Table 9.

TABLE 9

Specific Detection of Borrelia Using a 16S Ribosomal RNA Probe (SEQ ID No. 1)

| | | RLU | | |
|---|---|---|---|---|
| Organism | ATCC NO. | All-bacterial probe | Fungal probe | Borrelia probe SEQ ID NO. 1 |
| Bacteroides fragilis | 23745 | 3,187,827 | ND | 2,930 |
| Borrelia garinii | | ND | ND | 677,715 |
| Candida albicans | 18804 | 4,600 | 653,049 | 709 |
| Escherichia coli | 25922 | 2,939,817 | ND | 5,593 |

TABLE 9-continued

Specific Detection of Borrelia Using a 16S Ribosomal RNA Probe (SEQ ID No. 1)

| | | RLU | | |
|---|---|---|---|---|
| Organism | ATCC NO. | All-bacterial probe | Fungal probe | Borrelia probe SEQ ID NO. 1 |
| Haemophilua influenzae | 19418 | 3,390,520 | ND | 2,141 |
| Klebsiella pneumoniae | 23357 | 2,990,461 | ND | 5,587 |
| Proteus mirabilis | 25933 | 2,690,623 | ND | 14,167 |
| Pseudomonas aeruginosa | 25330 | 3,294,884 | ND | 4,853 |
| Staphylococcus aureus | 25923 | 2,074,506 | ND | 15,565 |
| Staphylococcus epidermidis | 12228 | 966,143 | ND | 1,210 |
| Streptococcus mitis | 9811 | 3,501,310 | ND | 482 |
| Streptococcus pneumoniae | 6306 | 3,573,357 | ND | 481 |

Example 10

Amplification and Detection of Lyme Disease-Associated Borrelia from Three Different Phylogentic Groups The published sequences indicate conservation of the rRNA sequence among different Lyme disease-associated Borrelia at the site targeted by probe SEQ ID NO. 2. The following data demonstrate that the primers and probes of this invention are useful for amplification and detection of isolates from more than one geographical location, representing the three phylogenetic groupings of Borrelia associated with Lyme disease. Lysates were prepared from cultures of *B. burgdorferi*, strain N40 (group I), *B. garinii* strain IP-90 (a Russian isolate) and strain 014A (NBS16) (group II), and *B. afzelii* strain IP-3 (a Russian isolate) and strain 09A (ACA1, a Swedish isolate), by resuspending the cells from approximately 15 ml of culture in 0.1 ml of a solution containing 30 mM sodium phosphate ph 6.8, 1 mM EDTA, 1 mM EGTA, and 3% (w/v) lithium lauryl sulfate. To quantitate the amount of nucleic acid in each lysate, hybridizations were performed with different amounts of the lysate and a probe directed to a conserved region of the 23S rRNA. The values obtained were compared to results with a known standard. Known amounts of *B. burgdorferi*, *B. garinii*, and *B. afzelli* lysate (representing approximately=$3 \times 10^{-19}$ moles of rRNA) were amplified in the polymerase chain reaction containing 50 pmol of a primer having a 3' target hybridizing region of SEQ ID NO. 8, which is complementary to *B. burgdorferi* 16S rRNA, and a primer of the same sense as the rRNA of sequence SEQ ID NO. 11 and 50 mM Tris HCl pH8, 25 mM KCl, 2 mM MgCl$_2$, 2.5 U AmpliTaq polymerase (Perkin-Elmer). Reactions were heated to 95° C. for 2 minutes, and then cycled 35 times through the temperatures of 55° C. 1 minutes, 72° C. 1 minute, 95° C. 0.5 min, followed by cooling to 4° C. until assay. Agarose gel analysis showed that nucleic acid from all three of the phylogenetic groups produced a 175 base pair fragment detectable by ethidium bromide staining. Hybridization of the samples containing *B. afzelii* strain 09A nucleic acids to acridinium ester labeled probe SEQ ID NO. 2 at 56° C. revealed a positive signal (at least 19 times background) with this probe. Samples containing *B. burgdorferi*, *B.*

*garinii*, strain IP-90 or 014A, or *B. afzelii* IP-3 nucleic acids gave signal at least 178 times background even when hybridized at 60° C. The *B. afzelii* 098 strain gave a lower hybridization signal than the other isolates but was still clearly detected over background.

Example 11

Specific Amplification and Detection of Lyme Disease-Associated Borrelia at 56° C.

In this example, a 100 μl reaction containing 30 pmol of the promoter primer synthesized with sequence SEQ ID NO. 8 and a primer of sequence SEQ ID NO. 11 were used. The lysates were diluted in water to the appropriate concentration and added to a solution containing the primer and promoter primer, heated to 95° C. for 15 minutes, and cooled to 42° C. for 5 minutes. Moloney Murine Leukemia Virus reverse transcriptase (MMLV RT), 900 units, and 400 units of T7 RNA polymerase were added. The final amplification mixture contained 50 mM Tris HCl, pH8.5, 35 mM potassium chloride, 4 mM GTP, 4 mM ATP, 4 mM UTP, 4 mM CTP, 1 mM dATP, 1 mM dTTP, 1 mM GTP, 1 mM dGTP, 20 mM $MgCl_2$, 20 mM N-Acetyl-L-Cysteine, and 5% glycerol. After a two hour incubation at 42° C., the entire one hundred μl amplification reaction was assayed by hybridization with an acridinium ester labeled probe of sequence SEQ ID NO. 2 and unlabeled helper probes of SEQ ID NOs. 4 and 6 or SEQ ID NO. 10 with unlabeled helpers SEQ ID NOs. 4 and 6. Hybridization was performed in 200 μl of a solution containing 0.05 M lithium succinate pH 5, 0.6 M LiCl, 1% (w/v) lithium lauryl sulfate, 10 mM EDTA, 10 mM EGTA, at 56° C. for 15 minutes, followed by addition of 300 μl of 0.15 M sodium tetraborate pH 8.5, 1% Triton®X-100. This mixture was incubated at 56° C. for 15 minutes, and cooled to room temperature. The remaining chemiluminescence in each tube was assayed in a Gen-Probe LEADERS 1 luminometer equipped with automatic injection of 1 mM nitric acid and 0.1% hydrogen peroxide followed by injection of a solution containing 1 N sodium hydroxide. Results are given in RLU.

These data show hybridization of probe SEQ ID NO. 2 at 56° C. temperature still allowed clear discrimination between *B. burgdorferi* and *B. hermsii*.

TABLE 10

Specific Amplification and Detection of Lyme Disease-Associated Borrelia at 56° C.

| | RLU | |
| --- | --- | --- |
| Target | Probe: SEQ ID NO. 2 Helper Probes: SEQ ID NOs. 4 & 6 | Probe: SEQ ID NO. 10 Helper Probes: SEQ ID NOs. 4 & 6 |
| *B. burg-dorferi* | 1,283,440 | 7,226 |
| | 1,250,367 | 4,876 |
| | 1,237,904 | 6,194 |
| *B. hermsii* | 4,932 | 3,091,864 |
| | 6,121 | 3,135,657 |
| | 4,805 | 3,149,342 |

Example 12

Amplification of Borrelia Nucleic Acid Using Amplification Primers Containing a Promoter Sequence The amplification oligos and probes may also be used in a format using only a promoter-primer and no primer. This format is described by PCT publication number WO 93/22461. Two promoter primers were synthesized, each containing a T7 RNA polymerase promoter sequence SEQ ID No. 43, 5'-AATTTAATACGACTCACTATAGGGAGA-3' at the 5' end covalently attached to a target complementary sequence (SEQ ID NO. 8) at the 3' end. One promoter primer was synthesized with a free 3' OH group, and was used at four pmol per 100 μl reaction. The second promoter primer was synthesized with an alkane diol at the 3' end and was used at 26 pmol per 100 μl reaction. The Borrelia lysates were diluted in water to the appropriate concentration and added to a solution containing the promoter primer, heated to 95° C. for 5 minutes, and cooled to 42° C. for 15 minutes. Moloney Murine Leukemia Virus reverse transcriptase (MMLV RT), 900 units, and 400 units of T7 RNA polymerase were added. The final amplification mixture contained 50 mM Tris HCl, pH8.5, 35 mM potassium chloride, 4 mM GTP, 4 mM ATP, 4 mM UTP, 4 mM CTP, 1 mM dATP, 1 mM dTTP, 1 mM dCTP, 1 mM dGTP, 20 mM UTP, 4 mM CTP, 1 mM dATP, 1 mM dTTP, 1 mM dCTP, 1 mM dGTP, 20 mM $MgCl_2$ 20 mM N-Acetyl-L-Cysteine, and 5% glycerol. After a 3.5 hour incubation at 42° C., 30 μl of the amplification reaction was assayed by hybridization with a acridinium ester labeled probe of sequence SEQ ID NO. 2 and unlabeled helper probes of SEQ ID NOs. 4 and 6. Hybridization was performed in 200 μl of a solution containing 0.05 M lithium succinate pH 5, 0.6 M LiCl, 1% (w/v) lithium lauryl sulfate, 10 mM EDTA, 10 mM EGTA, at 60° C. for 15 minutes, followed by addition of 300 μl of 0.15 M sodium at 60° C. for 15 minutes, and cooled to room temperature. The remaining chemiluminescence in each tube was assayed in a Gen-Probe LEADER® I luminometer. The table also shows data generated under the same conditions using a pair of promoter-primers containing the same promoter sequence SEQ ID No. 43, 5'-AATTTAATACGACTCACTATAGGGAGA-3' and a 3' target complementary region SEQ ID NO. 9. Four pmol of the promoter-primer having a free 3' OH group and 26 pmol of the same promoter primer synthesized with a 3' alkane diol group was used per 100 μl reaction.

TABLE 11

Amplification of Borrelia Nucleic Acids using Amplification Primers Containing a Promoter Sequence

| | Promoter-prim-er | RLU | |
| --- | --- | --- | --- |
| mole rRNA | | SEQ ID NO. 8 | SEQ ID NO. 9 |
| $7 \times 10^{-20}$ | | 127,047 | 1,391,860 |
| | | 1,685,890 | 1,199,380 |
| | | 1,631,427 | 905,384 |
| $3 \times 10^{-20}$ | | 1,561,824 | 1,606,256 |
| | | 1,329,922 | 1,502,425 |
| | | 702,994 | 1,518,290 |
| $2 \times 10^{-20}$ | | 693,532 | 1,557,769 |
| | | 262,589 | 327,939 |
| | | 476,310 | 1,370,173 |
| 0 | | 4,115 | 4,279 |
| | | 5,241 | 2,642 |

Other embodiments are within the following claims.

We claim:

1. A hybridization assay probe for detecting Lyme disease-associated Borrelia, said probe having a nucleotide base sequence selected from:
   a first group of nucleotide base sequences consisting of the sequences of SEQ ID NO: 1, SEQ ID NO: 2, SEQ ID NO: 12 and SEQ ID NO: 13, and
   a second group of nucleotide base sequences substantially corresponding to the sequences of SEQ ID NO: 21, SEQ ID NO: 24, SEQ ID NO: 25 or SEQ ID NO: 26, wherein the nucleotide base sequences of said second group will hybridize to a target nucleic acid sequence present in nucleic acid from Lyme disease-associated Borrelia and not to nucleic acid from *Borrelia hermsii* under stringent hybridization conditions.

2. The probe of claim 1, wherein said nucleotide base sequence consists of SEQ ID NO: 1.

3. The probe of claim 1, wherein said nucleotide base sequence consists of SEQ ID NO: 2.

4. The probe of claim 1, wherein said nucleotide base sequence consists of SEQ ID NO: 12.

5. The probe of claim 1, wherein said nucleotide base sequence consists of SEQ ID NO: 13.

6. The probe of claim 1, wherein said nucleotide base sequence consists of SEQ ID NO: 21.

7. The probe of claim 1, wherein said nucleotide base sequence consists of SEQ ID NO: 24.

8. The probe of claim 1, wherein said nucleotide base sequence consists of SEQ ID NO: 25.

9. The probe of claim 1, wherein said nucleotide base sequence consists of SEQ ID NO: 26.

10. A probe mix comprising the probe of claim 1, and at least one helper oligonucleotide which hybridizes to a Borrelia nucleic acid sequence under stringent hybridization conditions.

11. The probe mix of claim 10, wherein said helper probe has a nucleotide base sequence substantially corresponding to the sequence of SEQ ID NO: 3, SEQ ID NO: 4, SEQ ID NO: 5, SEQ ID NO: 6, SEQ ID NO: 14, SEQ ID NO: 15, SEQ ID NO: 16, SEQ ID NO: 17, SEQ ID NO: 23 or SEQ ID NO: 28.

12. The probe mix of claim 10, wherein:
    said probe has a nucleotide base sequence consisting of the sequence of SEQ ID NO: 2 or SEQ ID NO: 13; and
    said helper oligonucleotide has a nucleotide base sequence substantially corresponding to the sequence of SEQ ID NO: 4, SEQ ID NO: 6, SEQ ID NO: 15 or SEQ ID NO: 17.

13. The probe mix of claim 10, wherein:
    said probe has a nucleotide base sequence consisting of the sequence of SEQ ID NO: 2; and
    said helper oligonucleotide has a nucleotide base sequence substantially corresponding to the sequence of SEQ ID NO: 4 or SEQ ID NO: 6.

14. The probe mix of claim 10, wherein:
    said probe has a nucleotide base sequence consisting of the sequence of SEQ ID NO: 1 or SEQ ID NO: 12; and
    said helper oligonucleotide has a nucleotide base sequence substantially corresponding to the sequence of SEQ ID NO: 3, SEQ ID NO: 5, SEQ ID NO: 14 or SEQ ID NO: 16.

15. The probe mix of claim 10, wherein:
    said probe has a nucleotide base sequence consisting of the sequence of SEQ ID NO: 1; and
    said helper oligonucleotide has a nucleotide base sequence substantially corresponding to the sequence of SEQ ID NO: 3 or SEQ ID NO: 5.

16. The probe mix of claim 10, wherein:
    said probe has a nucleotide base sequence consisting of the sequence of SEQ ID NO: 21 or SEQ ID NO: 25; and
    said helper oligonucleotide has a nucleotide base sequence substantially corresponding to the sequence of SEQ ID NO: 23 or SEQ ID NO: 28.

17. The probe mix of claim 10, wherein:
    said probe has a nucleotide base sequence consisting of the sequence of SEQ ID NO: 21; and
    said helper oligonucleotide has a nucleotide base sequence substantially corresponding to the sequence of SEQ ID NO: 23.

18. A hybridization assay probe for detecting *Borrelia hermsii*, said probe having a nucleotide base sequence selected from:
    a first group of nucleotide base sequences consisting of the sequences of SEQ ID NO: 10, SEQ ID NO: 33, SEQ ID NO: 34 and SEQ ID NO: 35, and
    a second group of nucleotide base sequences substantially corresponding to the sequences of SEQ ID NO: 22, SEQ ID NO: 30, SEQ ID NO: 31 and SEQ ID NO: 32, wherein the nucleotide base sequences of said second group will hybridize to a target nucleic acid sequence present in nucleic acid from *Borrelia hermsii* and not to nucleic acid from any other Borrelia species under stringent hybridization conditions.

19. The probe of claim 18, wherein said nucleotide base sequence consists of SEQ ID NO: 10.

20. The probe of claim 18, wherein said nucleotide base sequence consists of SEQ ID NO: 33.

21. The probe of claim 18, wherein said nucleotide base sequence consists of SEQ ID NO: 34.

22. The probe of claim 18, wherein said nucleotide base sequence consists of SEQ ID NO: 35.

23. The probe of claim 18, wherein said nucleotide base sequence consists of SEQ ID NO: 22.

24. The probe of claim 18, wherein said nucleotide base sequence consists of SEQ ID NO: 30.

25. The probe of claim 18, wherein said nucleotide base sequence consists of SEQ ID NO: 31.

26. The probe of claim 18, wherein said nucleotide base sequence consists of SEQ ID NO: 32.

27. A probe mix comprising the probe of claim 18, and at least one helper oligonucleotide, wherein said helper oligonucleotide hybridizes to a *Borrelia hermsii* nucleic acid sequence under stringent hybridization conditions.

28. The probe mix of claim 27, wherein said helper oligonucleotide has a nucleotide base sequence substantially corresponding to the sequence of SEQ ID NO: 5, SEQ ID NO: 6, SEQ ID NO: 16, SEQ ID NO: 17, SEQ ID NO: 23, SEQ ID NO: 27, SEQ ID NO: 28 or SEQ ID NO: 29.

29. The probe mix of claim 27, wherein:
said probe has a nucleotide base sequence consisting of the sequence of SEQ ID NO: 10 or SEQ ID NO: 33; and
said helper oligonucleotide has a nucleotide base sequence substantially corresponding to the sequence of SEQ ID NO: 5, SEQ ID NO: 6, SEQ ID NO: 16 or SEQ ID NO: 17.

30. The probe mix of claim 27, wherein:
said probe has a nucleotide base sequence consisting of the sequence of SEQ ID NO: 10; and
said helper oligonucleotide has a nucleotide base sequence substantially corresponding to the sequence of SEQ ID NO: 6 or SEQ ID NO: 17.

31. The probe mix of claim 27, wherein:
said probe has a nucleotide base sequence consisting of the sequence of SEQ ID NO: 10; and
said helper oligonucleotide has a nucleotide base sequence substantially corresponding to the sequence of SEQ ID NO: 6.

32. The probe mix of claim 27, wherein said helper oligonucleotide has a nucleotide base sequence substantially corresponding to the sequence of SEQ ID NO: 23, SEQ ID NO: 27, SEQ ID NO: 28 or SEQ ID NO: 29.

33. The probe mix of claim 27, wherein:
said probe has a nucleotide base sequence consisting of the sequence of SEQ ID NO: 22; and
said helper oligonucleotide has a nucleotide base sequence substantially corresponding to the sequence of SEQ ID NO: 23 or SEQ ID NO: 28.

34. The probe mix of claim 28, wherein:
said probe has a nucleotide base sequence consisting of the sequence of SEQ ID NO: 22; and
said helper oligonucleotide has a nucleotide base sequence substantially corresponding to the sequence of SEQ ID NO: 23.

35. A method for detecting the presence of Lyme disease-associated Borrelia in a sample, said method comprising:
a) contacting said sample with a nucleic acid hybridization assay probe having a nucleotide base sequence selected from:
a first group of nucleotide base sequences consisting of the sequences of SEQ ID NO: 1, SEQ ID NO: 2, SEQ ID NO: 12 and SEQ ID NO: 13, and
a second group of nucleotide base sequences substantially corresponding to the sequences of SEQ ID NO: 21, SEQ ID NO: 24, SEQ ID NO: 25 and SEQ ID NO: 26;
b) incubating said sample under conditions such that said probe hybridizes to a target nucleic acid sequence present in nucleic acid from a Lyme disease-associated Borrelia and not to nucleic acid from *Borrelia hermsii*; and
b) detecting the hybridization of said probe to said target sequence as an indication of the presence of Lyme disease-associated Borrelia in said sample.

36. The method of claim 35, wherein said nucleotide base sequence consists of SEQ ID NO: 1.

37. The method of claim 35, wherein said nucleotide base sequence consists of SEQ ID NO: 2.

38. The method of claim 35, wherein said nucleotide base sequence consists of SEQ ID NO: 12.

39. The method of claim 35, wherein said nucleotide base sequence consists of SEQ ID NO: 13.

40. The method of claim 35, wherein said nucleotide base sequence consists of SEQ ID NO: 21.

41. The method of claim 35, wherein said nucleotide base sequence consists of SEQ ID NO: 24.

42. The method of claim 35, wherein said nucleotide base sequence consists of SEQ ID NO: 25.

43. The method of claim 35, wherein said nucleotide base sequence consists of SEQ ID NO: 26.

44. An amplification oligonucleotide having a nucleotide base sequence selected from:
a first group of nucleotide base sequences consisting of the sequences of SEQ ID NO: 9 and SEQ ID NO: 11, and
a second group of nucleotide base sequences substantially corresponding to the sequences of SEQ ID NO: 7, SEQ ID NO: 18, SEQ ID NO: 19, SEQ ID NO: 20, SEQ ID NO: 23, SEQ ID NO: 28, SEQ ID NO: 44, SEQ ID NO: 46, SEQ ID NO: 47, SEQ ID NO: 48, SEQ ID NO: 49 and SEQ ID NO: 50,
wherein said amplification oligonucleotide optionally has a 5' sequence recognized by an RNA polymerase or which enhances initiation or elongation by an RNA polymerase.

45. The amplification oligonucleotide of claim 44, wherein said nucleotide base sequence consists of SEQ ID NO: 7.

46. The amplification oligonucleotide of claim 44, wherein said nucleotide base sequence consists of SEQ ID NO: 9.

47. The amplification oligonucleotide of claim 44, wherein said nucleotide base sequence consists of SEQ ID NO: 11.

48. The amplification oligonucleotide of claim 44, wherein said nucleotide base sequence consists of SEQ ID NO: 18.

49. The amplification oligonucleotide of claim 44, wherein said nucleotide base sequence consists of SEQ ID NO: 19.

50. The amplification oligonucleotide of claim 44, wherein said nucleotide base sequence consists of SEQ ID NO: 20.

51. The amplification oligonucleotide of claim 44, wherein said nucleotide base sequence consists of SEQ ID NO: 23.

52. The amplification oligonucleotide of claim 44, wherein said nucleotide base sequence consists of SEQ ID NO: 28.

53. The amplification oligonucleotide of claim 44, wherein said nucleotide base sequence consists of SEQ ID NO: 44.

54. The amplification oligonucleotide of claim 44, wherein said nucleotide base sequence consists of SEQ ID NO: 46.

55. The amplification oligonucleotide of claim 44, wherein said nucleotide base sequence consists of SEQ ID NO: 47.

56. The amplification oligonucleotide of claim 44, wherein said nucleotide base sequence consists of SEQ ID NO: 48.

57. The amplification oligonucleotide of claim 44, wherein said nucleotide base sequence consists of SEQ ID NO: 49.

58. The amplification oligonucleotide of claim 44, wherein said nucleotide base sequence consists of SEQ ID NO: 50.

59. An amplification oligonucleotide having a nucleotide base sequence which has at least 90% base identity with the sequence of SEQ ID NO: 8 or SEQ ID NO: 45, wherein said amplification oligonucleotide includes the 19 most 3' nucleotides of SEQ ID NO: 8 or SEQ ID NO: 45, and wherein said amplification oligonucleotide optionally has a 5' sequence recognized by an RNA polymerase or which enhances initiation or elongation by an RNA polymerase.

60. The amplification oligonucleotide of claim 59, wherein said nucleotide base sequence consists of SEQ ID NO: 8.

61. The amplification oligonucleotide of claim 59, wherein said nucleotide base sequence consists of SEQ ID NO: 45.

62. The oligonucleotide of claim 44 or 59, wherein said amplification oligonucleotide has said 5' sequence.

63. A method for amplifying a Borrelia nucleic acid comprising amplifying a Borrelia nucleic acid with one or more amplification oligonucleotides, wherein each of said amplification oligonucleotides has a nucleotide base sequence selected from:
   a first group of nucleotide base sequences consisting of the sequences of SEQ ID NO: 9 and SEQ ID NO: 11, and
   a second group of nucleotide base sequences substantially corresponding to the sequences of SEQ ID NO: 7, SEQ ID NO: 18, SEQ ID NO: 19, SEQ ID NO: 20, SEQ ID NO: 23, SEQ ID NO: 28, SEQ ID NO: 44, SEQ ID NO: 46, SEQ ID NO: 47, SEQ ID NO: 48, SEQ ID NO: 49 and SEQ ID NO: 50,
   wherein said amplification oligonucleotide optionally has a sequence recognized by an RNA polymerase or which enhances initiation or elongation by an RNA polymerase.

64. The amplification oligonucleotide of claim 63, wherein said nucleotide base sequence consists of SEQ ID NO: 7.

65. The amplification oligonucleotide of claim 63, wherein said nucleotide base sequence consists of SEQ ID NO: 9.

66. The amplification oligonucleotide of claim 63, wherein said nucleotide base sequence consists of SEQ ID NO: 11.

67. The amplification oligonucleotide of claim 63, wherein said nucleotide base sequence consists of SEQ ID NO: 18.

68. The amplification oligonucleotide of claim 63, wherein said nucleotide base sequence consists of SEQ ID NO: 19.

69. The amplification oligonucleotide of claim 63, wherein said nucleotide base sequence consists of SEQ ID NO: 20.

70. The amplification oligonucleotide of claim 63, wherein said nucleotide base sequence consists of SEQ ID NO: 23.

71. The amplification oligonucleotide of claim 64, wherein said nucleotide base sequence consists of SEQ ID NO: 28.

72. The amplification oligonucleotide of claim 65, wherein said nucleotide base sequence consists of SEQ ID NO: 44.

73. The amplification oligonucleotide of claim 66, wherein said nucleotide base sequence consists of SEQ ID NO: 46.

74. The amplification oligonucleotide of claim 67, wherein said nucleotide base sequence consists of SEQ ID NO: 47.

75. The amplification oligonucleotide of claim 68, wherein said nucleotide base sequence consists of SEQ ID NO: 48.

76. The amplification oligonucleotide of claim 63, wherein said nucleotide base sequence consists of SEQ ID NO: 49.

77. The amplification oligonucleotide of claim 63, wherein said nucleotide base sequence consists of SEQ ID NO: 50.

78. A method for amplifying a Borrelia nucleic acid comprising amplifying said nucleic acid with at least two amplification oligonucleotides comprising:
   a first amplification oligonucleotide having a nucleotide base sequence substantially corresponding to the sequence of SEQ ID NO: 7 or SEQ ID NO: 44; and
   a second amplification oligonucleotide having a nucleotide base sequence selected from:
      a first group of nucleotide base sequences consisting of the sequences of SEQ ID NO: 8 and SEQ ID NO: 9, and
      a second group of nucleotide base sequences substantially corresponding to the sequences of SEQ ID NO: 45 and SEQ ID NO: 46,
   wherein one of said amplification oligonucleotides optionally has a sequence recognized by an RNA polymerase or which enhances initiation or elongation by an RNA polymerase.

79. A method for amplifying a Borrelia nucleic acid comprising amplifying said nucleic acid with at least two amplification oligonucleotides comprising:
   a first amplification oligonucleotide having a nucleotide base sequence consisting of the sequence of SEQ ID NO: 11 or a nucleotide base sequence substantially corresponding to the sequence of SEQ ID NO: 7, SEQ ID NO: 44 or SEQ ID NO: 47; and
   a second amplification oligonucleotide having a nucleotide base sequence consisting of the sequence of SEQ ID NO: 8 or a nucleotide base sequence substantially corresponding to the sequence of SEQ ID NO: 45,
   wherein one of said amplification oligonucleotides optionally has a sequence recognized by an RNA polymerase or which enhances initiation or elongation by an RNA polymerase.

80. A method for amplifying a Borrelia nucleic acid comprising amplifying said nucleic acid with at least two amplification oligonucleotides comprising:
   a first amplification oligonucleotide having a nucleotide base sequence substantially corresponding to the sequence of SEQ ID NO: 40 or SEQ ID NO 18; and
   a second amplification oligonucleotide having a nucleotide base sequence substantially corresponding to the sequence of SEQ ID NO: 19, SEQ ID NO: 49, SEQ ID NO: 20 or SEQ ID NO: 50.

81. The method of claim 80, wherein said Borrelia nucleic acid is a Lyme disease-associated Borrelia nucleic acid or a *Borrelia hermsii* nucleic acid.

82. The method of claim 80, further comprising detecting the amplified Borrelia nucleic acid with a hybridization assay probe able to specifically hybridize to said amplified Borrelia nucleic acid under stringent hybridization conditions, said probe having a nucleotide base sequence substantially corresponding to the sequence of SEQ ID NO: 21, SEQ ID NO: 24, SEQ ID NO: 25, SEQ ID NO: 26, SEQ ID NO: 22, SEQ ID NO: 30, SEQ ID NO: 31 or SEQ ID NO: 32.

83. A kit containing an oligonucleotide having a nucleotide base sequence selected from:
   a first group of nucleotide base sequences consisting of the sequences of SEQ ID NO: 1, SEQ ID NO: 2, SEQ ID NO: 12 and SEQ ID NO: 13, and
   a second group of nucleotide base sequences substantially corresponding to the sequence of SEQ ID NO: 21, SEQ ID NO: 24, SEQ ID NO: 25 and SEQ ID NO: 26,
wherein the nucleotide base sequences of said second group will hybridize to a target nucleic acid sequence present in nucleic acid from Lyme disease-associated Borrelia and not to nucleic acid from *Borrelia hermsii* under stringent hybridization conditions.

84. The kit of claim 83 further containing a helper oligonucleotide having a nucleotide base sequence substantially corresponding to the sequence of SEQ ID NO: 3, SEQ ID NO: 5, SEQ ID NO: 14, SEQ ID NO: 16, SEQ ID NO: 4, SEQ ID NO: 6, SEQ ID NO: 15, SEQ ID NO: 17, SEQ ID NO: 23 or SEQ ID NO: 28.

85. A kit containing two different oligonucleotides, wherein each of said oligonucleotides has a nucleotide base sequence selected from:
   a first group of nucleotide base sequences consisting of the sequences of SEQ ID NO: 8, SEQ ID NO: 9 and SEQ ID NO: 11, and
   a second group of nucleotide base sequences substantially corresponding to the sequences of SEQ ID NO: 7, SEQ ID NO: 18, SEQ ID NO: 19 and SEQ ID NO: 20,
   wherein at least one of said oligonucleotides optionally has a 5' sequence recognized by an RNA polymerase or which enhances initiation or elongation by an RNA polymerase.

86. The kit of claim 85 further containing an oligonucleotide probe having a nucleotide base sequence selected from:
   a first group on nucleotide base sequences consisting of the sequences of SEQ ID NO: 1, SEQ ID NO: 2 and SEQ ID NO: 10, and
   a second group of nucleotide base sequences substantially corresponding to the sequences of SEQ ID NO: 21 and SEQ ID NO: 22.

87. A kit containing the following three oligonucleotides:
   a first oligonucleotide having a nucleotide base sequence substantially corresponding to the sequence of SEQ ID NO: 7;
   a second oligonucleotide having a nucleotide base sequence consisting of the sequence of SEQ ID NO: 8; and
   a third oligonucleotide having a nucleotide base sequence consisting of the sequence of SEQ ID NO: 1 or SEQ ID NO: 2.

88. A kit containing the following three oligonucleotides:
   a first oligonucleotide having a nucleotide base sequence substantially corresponding to the sequence of SEQ ID NO: 7;
   a second oligonucleotide having a nucleotide base sequence consisting of the sequence of SEQ ID NO: 9; and
   a third oligonucleotide having a nucleotide base sequence consisting of the sequence of SEQ ID NO: 1 or SEQ ID NO: 2.

89. A kit containing an oligonucleotide having a nucleotide base sequence which has at least 90% base identity with the sequence of SEQ ID NO: 8 or SEQ ID NO: 45, wherein said oligonucleotide includes the 19 most 3' nucleotides of SEQ ID NO: 8 or SEQ ID NO: 45.

90. A kit containing the following three oligonucleotides:
   a first oligonucleotide having a nucleotide base sequence consisting of the sequence of SEQ ID NO: 11;
   a second oligonucleotide having a nucleotide base sequence consisting of the sequence of SEQ ID NO: 8; and
   a third oligonucleotide having a nucleotide base sequence consisting of the sequence of SEQ ID NO: 10 or SEQ ID NO: 33.

91. A kit containing the following three oligonucleotides:
   a first oligonucleotide having a nucleotide base sequence substantially corresponding to the sequence of SEQ ID NO: 18;
   a second oligonucleotide having a nucleotide base sequence substantially corresponding to the sequence of SEQ ID NO: 19; and
   a third oligonucleotide having a nucleotide base sequence substantially corresponding to the sequence of SEQ ID NO: 21, SEQ ID NO: 24, SEQ ID NO: 22 or SEQ ID NO: 31.

92. A kit containing the following three oligonucleotides:
   a first oligonucleotide having a nucleotide base sequence substantially corresponding to the sequence of SEQ ID NO: 18;
   a second oligonucleotide having a nucleotide base sequence substantially corresponding to the sequence of SEQ ID NO: 20; and
   a third oligonucleotide having a nucleotide base sequence substantially corresponding to the sequence of SEQ ID NO: 21, SEQ ID NO: 24, SEQ ID NO: 22 or SEQ ID NO: 31.

93. A hybridization assay probe for detecting the presence of *Borrelia hermsii* in a sample, said probe having a nucleotide base sequence consisting of the sequence of SEQ ID NO: 10, SEQ ID NO: 33, SEQ ID NO: 34 or SEQ ID NO: 35.

94. The probe of claim 93, wherein said nucleotide base sequence consists of SEQ ID NO: 10.

95. The probe of claim 93, wherein said nucleotide base sequence consists of SEQ ID NO: 33.

96. The probe of claim 93, wherein said nucleotide base sequence consists of SEQ ID NO: 34.

97. The probe of claim 93, wherein said nucleotide base sequence consists of SEQ ID NO: 35.

98. A probe mix comprising the probe of claim 93 and at least one helper oligonucleotide which hybridizes to a *Borrelia hermsii* nucleic acid sequence under stringent hybridization conditions.

99. The probe mix of claim 98, wherein:
   said probe has a nucleotide base sequence consisting of the sequence of SEQ ID NO: 10 or SEQ ID NO: 34; and
   said helper oligonucleotide has a nucleotide base sequence substantially corresponding to the sequence of SEQ ID NO: 6 or SEQ ID NO: 17.

100. A hybridization assay probe for detecting the presence of *Borrelia hermsii* in a sample, said probe having a nucleotide base sequence substantially corresponding to the sequence of SEQ ID NO: 22, SEQ ID NO: 30, SEQ ID NO: 31 or SEQ ID NO: 32, wherein said probe will hybridize to a target nucleic acid sequence present in nucleic acid from *Borrelia hermsii* and not to nucleic acid from *Borrelia burgdorferi* under stringent hybridization conditions.

101. The probe of claim 100, wherein said nucleotide base sequence consists of SEQ ID NO: 22.

102. The probe of claim 100, wherein said nucleotide base sequence consists of SEQ ID NO: 30.

103. The probe of claim 100, wherein said nucleotide base sequence consists of SEQ ID NO: 31.

104. The probe of claim 100, wherein said nucleotide base sequence consists of SEQ ID NO: 32.

105. A probe mix comprising the probe of claim 100 and at least one helper oligonucleotide which hybridizes to a *Borrelia hermsii* nucleic acid sequence under stringent hybridization conditions.

106. The probe mix of claim 105, wherein:
said probe has a nucleotide base sequence substantially corresponding to the sequence of SEQ ID NO: 22 or SEQ ID NO: 31; and
said helper oligonucleotide has a nucleotide base sequence substantially corresponding to the sequence of SEQ ID NO: 23 or SEQ ID NO: 28.

107. A method for detecting the presence of *Borrelia hermsii* in a sample, said method comprising:
a) contacting said sample with a hybridization assay probe having a nucleotide base sequence consisting of the sequence of SEQ ID NO: 10, SEQ ID NO: 33, SEQ ID NO: 34 or SEQ ID NO: 35;
b) incubating said sample under conditions such that said probe hybridizes to a target nucleic acid sequence present in nucleic acid from *Borrelia hermsii* and not to nucleic acid from *Borrelia burgdorferi*: and
c) detecting the hybridization of said probe to said target sequence as an indication of the presence of *Borrelia hermsii* in said sample.

108. A method for detecting the presence of *Borrelia hermsii* in a sample comprising:
a) contacting said sample with a hybridization assay probe having a nucleotide base sequence substantially corresponding to the sequence of SEQ ID NO: 22, SEQ ID NO: 30, SEQ ID NO: 31 or SEQ ID NO: 32;
b) incubating said sample under conditions such that said probe hybridizes to a target nucleic acid sequence present in nucleic acid from *Borrelia hermsii* and not to nucleic acid from *Borrelia burgdorferi*: and
c) detecting the hybridization of said probe to said target sequence as an indication of the presence of *Borrelia hermsii* in said sample.

109. A probe mix comprising:
an oligonucleotide probe having a nucleotide base sequence selected from:
a first group of nucleotide base sequences consisting of the sequences of SEQ ID NO: 10, SEQ ID NO: 33, SEQ ID NO: 34 and SEQ ID NO: 35, and
a second group of nucleotide base sequences substantially corresponding to the sequences of SEQ ID NO: 22, SEQ ID NO: 30, SEQ ID NO: 31 and SEQ ID NO: 32;
a helper oligonucleotide having a nucleotide base sequence substantially corresponding to the sequence of SEQ ID NO: 6 or SEQ ID NO: 17; and
a third oligonucleotide having a nucleotide base sequence selected from:
a third group of nucleotide base sequences consisting of the sequences of SEQ ID NO: 8 and SEQ ID NO: 11 and
a fourth group of nucleotide base sequences substantially corresponding to the sequences of SEQ ID NO: 7, SEQ ID NO: 44, SEQ ID NO: 45 and SEQ ID NO: 47.

110. A probe mix comprising:
an oligonucleotide probe having a nucleotide base sequence selected from:
a first group of nucleotide base sequences consisting of the sequences of SEQ ID NO: 10, SEQ ID NO: 33, SEQ ID NO: 34 and SEQ ID NO: 35, and
a second group of nucleotide base sequences substantially corresponding to the sequences of SEQ ID NO: 22, SEQ ID NO: 30, SEQ ID NO: 31 and SEQ ID NO: 32;
a helper oligonucleotide having a nucleotide base sequence substantially corresponding to the sequence of SEQ ID NO: 23 or SEQ ID NO: 28; and
a third oligonucleotide having a nucleotide base sequence substantially corresponding to the sequence of SEQ ID NO: 18, SEQ ID NO: 48, SEQ ID NO: 19, SEQ ID NO: 49, SEQ ID NO: 20 or SEQ ID NO: 50.

111. The method of claim 78 or 79 further comprising detecting the amplified Borrelia nucleic acid with a hybridization assay probe able to specifically hybridize to said amplified Borrelia nucleic acid under stringent hybridization conditions, said probe having a nucleotide base sequence substantially corresponding to the sequence of SEQ ID NO: 1, SEQ ID NO: 2, SEQ ID NO: 12, SEQ ID NO: 13, SEQ ID NO: 10, SEQ ID NO: 33,SEQ ID NO: 34 or SEQ ID NO: 35.

* * * * *